United States Patent [19]

Ōtake et al.

[11] Patent Number: 5,631,238

[45] Date of Patent: *May 20, 1997

[54] SPICAMYCIN DERIVATIVES AND THE USE THEREOF

[75] Inventors: Noboru Ōtake, Toshima-Ku; Hiroyuki Kawai, Takasaki; Tomiko Kawasaki, Takasaki; Atsuo Odagawa, Takasaki; Masaru Kamishohara, Takasaki; Teruyuki Sakai, Takasaki, all of Japan

[73] Assignee: Kirin Beer Kabushiki Kaisha, Tokyo-To, Japan

[*] Notice: The term of this patent shall not extend beyond the expiration date of Pat. No. 5,461,036.

[21] Appl. No.: 429,303

[22] Filed: Apr. 26, 1995

Related U.S. Application Data

[62] Division of Ser. No. 910,640, Jul. 8, 1992, Pat. No. 5,461,036.

[30] Foreign Application Priority Data

| Jul. 12, 1991 | [JP] | Japan | 3-198903 |
| Nov. 15, 1991 | [JP] | Japan | 3-326845 |
| Apr. 3, 1992 | [JP] | Japan | 4-110665 |

[51] Int. Cl.$^6$ .......................... A61K 31/70; C07H 19/16
[52] U.S. Cl. .......................... 514/45; 536/27.21
[58] Field of Search ................. 514/46, 45; 536/27.6, 536/27.21

[56] References Cited

U.S. PATENT DOCUMENTS

| 3,264,195 | 8/1966 | Dutcher . | |
| 4,086,416 | 4/1978 | Acton | 536/29.11 |
| 4,565,781 | 1/1986 | Otake | 536/29.11 |
| 4,975,434 | 12/1990 | Marquez . | |

FOREIGN PATENT DOCUMENTS

| 3407979 | 3/1984 | Germany . |
| 161389 | of 1984 | Japan . |
| 9015811 | 12/1990 | WIPO . |

OTHER PUBLICATIONS

Chemical Abstract 110(13):107444q Mar. 27, 1989.
Chemical Abstract 104(3):14615g Jan. 20, 1986.
Chemical Abstract 99(15):118916a Oct. 10, 1983.
Acton, J. Med. Chem. 20(11) 1362–1371, 1977.
Hayakawa et al. Aeric. Biol. Chem. 49(4):2685–2691 1985.
Hayakawa J. Antibiotics 36:934–937, 1983.
Zee Cheng, et al. Meth and Find Exptl. Clin. Pharmacol. 1988 10(2):67–101.
Berger, D.P. et al. Cancer Chemother Pharmacol. (1990) 26 (suppl.) 57–11.
Winograd, B. in vivo 1:1–14 (1987).
Mattern, J. et al. Lung Xenografts as a Predictive . . . Human Tumour Xenografts in Anticancer Drug.
Development, pp. 47–50, Springer–Verlag 1988 Carmichael et al . . . "Chemotherapy Studies . . . ".
Human Tumour Xenografts in Anticancer Drug Development, pp. 51–55, Springer–Verlag 1988.
Mattern, et al. Cancer and Metastasis Reviews 7:263–284 (1984).
Fieberg, H.H. Comparison of Tumor Response in Nude Mice Human Tumour Xenografts in Anticancer Drug Development Springer–Verlag, Berlin; pp. 25–30 (1988).
Robert, K.-Y. et al. Meth. and Find. ExpH. Clin. Pharmacol. 10, 67–101 (1988).
Berger, D. et al. Cancer Chemotherapy and Pharmacology 26, 57–511 (1990).
Winograd, B. et al. In Vivo, I, 1–14 (1987).
Cancer Res. 35, 2790–2796 (1975).
Cancer, 40. 2640–2650 (1977).
Gann 69, 299–309, 1978.
Fieberg, HH. Human Tumor.
Xenografts Berlin 1988 pp. 25–30.
Mattern, J. et al. Cancer and Metastis Reviews 7, 263–284 (1988).

*Primary Examiner*—Gary L. Kunz
*Attorney, Agent, or Firm*—Ladas & Parry

[57] ABSTRACT

Disclosed is a novel spicamycin derivative represented by the formula (I) or a salt thereof:

wherein R represents an alkenyl having a given number of carbon atoms, a haloalkyl having a given number of carbon atoms, $CH_3(CH_2)_nCH(OH)—$ or $CH_3(CH_2)_{n-1}CH(OH)—CH_2—$ (wherein n denotes an integer of 9–13), an alkyl with a certain group and a given number of carbon atoms, $$CH_3(CH_2)_a\underset{\underset{O}{\|}}{C}O(CH_2)_b—,$$

$$CH_3(CH_2)_{b-1}\underset{\underset{\underset{O}{\|}}{OC(CH_2)_aCH_3}}{CH—}$$

$$CH_3(CH_2)_{b-2}\underset{\underset{\underset{O}{\|}}{OC(CH_2)_aCH_3}}{CHCH_2—},$$

(wherein a denotes 2, and b denotes an integer of 10–15), $$CH_3(CH_2)_cSO_2O(CH_2)_d—,$$

$$CH_3(CH_2)_{d-1}\underset{OSO_2(CH_2)_cCH_3}{CH—},$$

(wherein c denotes an integer of 0–3 and d denotes an integer of 10–15), $(CH_3)_3Si(CH_2)_{10}—,$

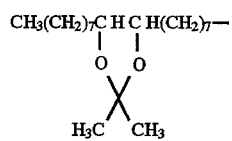
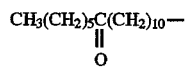
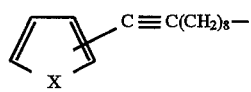
or
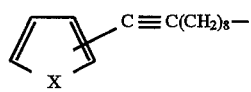
(wherein X represents O or S), and $R_1$ and $R_2$ are different from each other and each represents H or OH, which exhibits an excellent antitumor effect and has a high therapeutic index.
An antitumor agent containing at least one of the above-described compounds in an effective amount is also disclosed.
16 Claims, No Drawings

SPICAMYCIN DERIVATIVES AND THE USE THEREOF

This is a divisional of application Ser. No. 07/910,640 filed on Jul. 8, 1992, now U.S. Pat. No. 5,461,036.

BACKGROUND OF THE INVENTION

1. Field of the Art

The present invention relates to a spicamycin derivative which has an antitumor activity and is useful for medicines and a salt thereof, an antitumor agent containing the compound and a method for inhibiting tumor by using the compound.

2. Related Art

Hitherto, the present inventors have found the spicamycin represented by the formula:

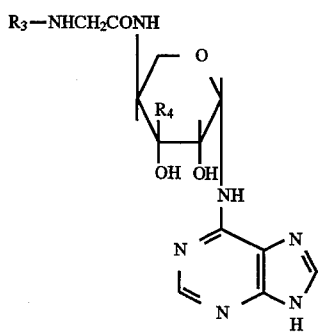

wherein $R_3$ represents $(CH_3)_2CH(CH_2)_nCO-$ (n=8–14) or $CH_3(CH_2)_mCO-$ (m=10–16) and $R_4$ represents $CH_2OHCH(OH)-$ (see Japanese Patent Laid-Open Publication No. 161396/1984).

The present inventors have also found Spicamycin X having 12 carbon atoms at the fatty acid side chain as a spicamycin compound which has a lower toxicity and a higher therapeutic coefficient as well as a unified component so that the compound can be used clinically as an antitumor agent (see Patent Application No. PCT/JP90/00781).

Spicamycin has a structure in which a specific aminoheptose, referred to hereinafter as spicamine, is bonded to the amino group at the 6-position of the purine, glycine is bonded by amide bond to the amino group at the 4-position of the spicamine and a fatty acid is further bonded by amide bond to the amino group of the glycine.

As the compounds having a similar structure to spicamycin, septacidin which is an isomer at the 2'-position of spicamine (see U.S. Pat. Nos. 3,155,647 and 3,264,195) and analogues of septacidin [Antimicrobial Agents and Chemotherapy, 845–849 (1965)] are known. These compounds, however, exhibit no antitumor activity against L1210 mouse leukemia and Walker 256 rat sarcoma [see Journal of Medicinal Chemistry, 20 (11), 1362, (1977); Nucleoside Antibiotics, Wiley-Interscience, New York, N.Y., p. 256 (1970)] and thus have a narrow antitumor spectrum.

The well-known compounds described above have problems to be solved and thus are presently not used clinically.

DISCLOSURE OF THE INVENTION

Outline of the Invention

The object of the present invention is to provide a novel compound which has an excellent antitumor activity as well as a high therapeutic coefficient indicating the width of the range of its effective dose.

The present inventors have conducted earnest researches on spicamycin compounds with laying stress on the animal experiments, especially an experiment of human tumor xenograft model which has been proved to be well consistent with the clinical efficiency of antitumor agents [Cancer Res., 35, 2790–2796 (1975); Cancer, 40, 2640–2650 (1977); Cann, 69, 299–309 (1978)]. As a result, they have found that the specific spicamycin derivatives can comply with the object and thus accomplished the present invention on the basis of the information.

That is, the spicamycin compounds according to the present invention are the spicamycin derivatives represented by the formula (I) or the salts thereof:

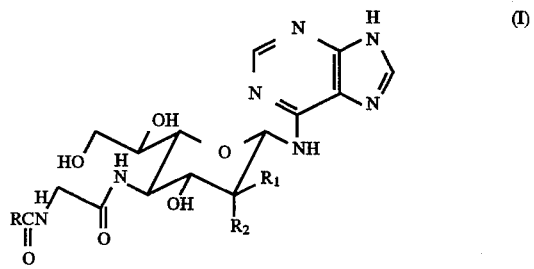

wherein R represents any one of the substituents defined by the following (i)–(xi), and $R_1$ and $R_2$ are different from each other and each represents H or OH:

(i) a linear or branched alkyl having 9–15 carbon atoms or a linear alkenyl having 10–17 carbon atoms, except for a linear alkyl having 11 carbon atoms when $R_1$ represents H and $R_2$ represents OK and for linear or branched alkyl and oleoyl having 11–15 carbon atoms when $R_1$ represents OH and $R_2$ represents H, (ii) a linear haloalkyl having 10–15 carbon atoms, (iii) $CH_3(CH_2)_nCH(OH)-$ or $CH_3(CH_2)_{n-1}CH(OH)-CH_2-$, wherein n denotes an integer of 9–13, (iv) an alkyl with an azide group or a cyano group and having 10–15 carbon atoms, (v) a linear alkyl with a phenoxy group or a halogen-substituted phenoxy group and having 10–13 carbon atoms, (vi)

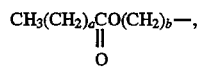

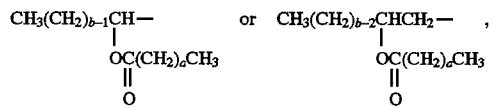

wherein a denotes an integer of 0–2 and b denotes an integer of 10–15, (vii) $CH_3(CH_2)_cSO_2O(CH_2)_d$— or

wherein c denotes an integer of 0–3 and d denotes an integer of 10–15, (viii) $(CH_3)_3Si(CH_2)_{10}$— or
$(CH_3)_3Si$—$C\equiv C$—$(CH_2)_8$—, (ix) 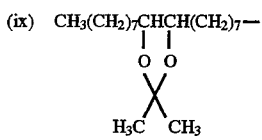

(x) 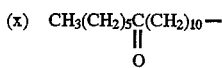

(xi) 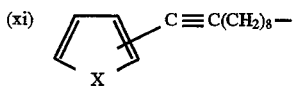

wherein X represents O or S.

The present invention also relates to the use of the compound. That is, the antitumor agent according to the present invention contains an effective amount of at least one of the spicamycin derivatives represented by the formula (I) described above or a salts thereof, or contains an effective amount of at least one of the spicamycin derivatives represented by the formula (I) and a carrier or a diluent.

The present invention also relates to a method for inhibiting tumor characterized in that at least one of the effective amount of the aforementioned compounds is administered to a patient which needs to inhibit tumor.

Effects of the Invention

The spicamycin compounds according to the present invention have the features of an excellent antitumor activity and the high therapeutic coefficient indicating the width of the efficiency range.

Detailed Description of the Invention

Spicamycin Derivatives and the salts thereof

The spicamycin derivatives according to the present invention, as described above, has the chemical structure represented by the formula (I), in which R is defined more specifically by any one of the following (i)–(xi). In this connection, as for the position number of the carbons in the group R, a carbon adjacent to the amide bond is expressed as the 2-position, and carbons adjacent to this carbon are sequentially designated as the 3-position, the 4-position and so on.

(i) R represents a linear or branched alkyl having 9–15 carbon atoms or a linear alkenyl having 10–17 carbon atoms, except for a linear alkyl having 11 carbon atoms in the case that $R_1$ represents H and $R_2$ represents OH and for linear or branched alkyl and oleoyl having 11–15 carbon atoms in the case that $R_1$ represents OH and $R_2$ represents H. When R represents an alkenyl, it has one or two double bonds at the 2-, 4-, 9-, 12-positions and at the terminal position. Particularly, R preferably has the double bonds at the 2- and 4-positions. Furthermore, R is most preferably an alkadienyl having double bonds at the 2- and 4-positions and 11–13 carbon atoms.

(ii) R represents a linear haloalkyl having 10–15 carbon atoms. The halogen can be bonded at the 2-position or the terminal position. The halogen is selected from fluorine, chlorine, bromine or iodine.

(iii) R represents a linear alkyl having an OH group at the 2- or 3-position and 11–15 carbon atoms, that is, $CH_3(CH_2)_nCH(OH)$— or $CH_3(CH_2)_{n-1}CH(OH)CH_2$—, wherein n denotes an integer of 9–13.

(iv) R represents an alkyl with an azide group or a cyano group and having 10–15 carbon atoms. The azide group or the cyano group can be bonded at the 2-position or the terminal position.

(v) R represents a linear alkyl group with a phenoxy group or a halogen-substituted phenoxy group and having 10–13 carbon atoms.

(vi) R is represented by the formulae:

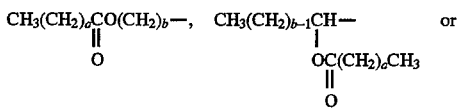

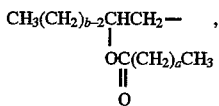

wherein a denotes an integer of 0–2 and b denotes an integer of 10–15, the sum of a and b being preferably 13, 14, 15 or 16.

(vii) R is represented by the formulae:
$CH_3(CH_2)_cSO_2O(CH_2)_d$— or

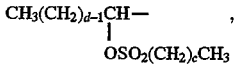

wherein c denotes an integer of 1–3 and d denotes an integer of 10–15, the sum of c and d being preferably 11, 13 or 14.

(viii) R is represented by the formula:
$(CH_3)_3Si(CH_2)_{10}$— or
$(CH_3)_3Si$—$C\equiv C$—$(CH_2)_8$—, (ix) R is represented by the formula:

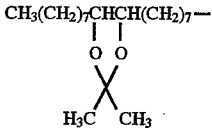

(x) R is represented by the formula:

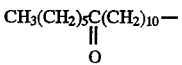

(xi) R is represented by the formula:

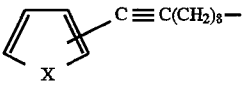

wherein X represents O or S.

The compounds represented by the formula (I) can include an acid adduct salt and a base adduct salt at the basic nitrogen atom and at the 7-position of the purine ring and a OH group, respectively. The spicamycin compounds according to the present invention also include these adduct salts.

The acids which form the acid adduct salts can be, for example, inorganic acids such as hydrochloric acid, sulfuric acid, nitric acid, phosphoric acid and the like, and organic acids such as acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and the like.

The base adduct salts can be ones with, for example, alkaline metal compounds such as sodium hydroxide, potassium hydroxide and the like, salts with alkaline earth metal compounds such as calcium hydroxide, magnesium hydroxide and the like, ammonium salts, and salts with organic bases such as triethylamine, ethanolamine and the like.

It is needless to say that when the acid adduct salt and the base adduct salt are used for medicines, the acid and the base must be pharmaceutically acceptable ones.

The preferred examples of the spicamycin compounds of the present invention are described in the following paragraph of the preparation of the spicamycin derivatives.

Preparation of Spicamycin Derivatives

SUMMARY (1) The compounds represented by the formula (I) wherein $R_1$=H and $R_2$=OH (Compound A)

The spicamycin derivatives of the present invention in this case can be presently prepared by the synthetic chemical modification of a spicamycin aminonucleoside, referred to hereinafter as 6-(spicaminyl-amino)purine, obtained by the hydrolysis of a mixture of spicamycins produced by culturing a microorganism (see Patent Application No. PCT/JP90/00781). Some spicamycin derivatives can be obtained directly from a microbial culture by using an appropriate separation means. Further, the spicamycin derivatives of the present invention may be prepared also by means of an overall synthetic chemical route.

The mixture of the spicamycins are obtained from the culture of the strain Streptomyces alanosinicus 879-MT$_3$ (H79) (FERM BP-449) isolated by the inventors, which strain has been deposited in Fermentation Research Institute Agency of Industrial Science and Technology, Japan, on Jul. 19, 1982. The spicamycin mixture can be produced by the method found by the present inventors (see Japanese Patent Laid-Open Publication No. 161396/1984).

While the spicamycin derivatives according to the present invention can be obtained by a variety of methods as described above, for example, the following method can be used as one of the specific production methods of the compounds.

Preparation of 6-(spicaminyl-amino)purine (i.e. spicamycin aminonucleoside):

6-(spicaminyl-amino)purine represented by the formula (IIa) below is obtained in the form of salts of its crude product with various acids by hydrolyzing the spicamycin mixture with a suitable inorganic acid such as hydrochloric acid or sulfuric acid, or a suitable organic acid such as acetic acid or formic acid. Specifically, the crude product is obtained by dissolving or suspending a spicamycin mixture in an alcoholic or aqueous solution of an acid such as hydrochloric acid and stirring the mixture at 20°–40° C. for 2–5 days. The neutralization and the subsequent concentration of the crude product followed by the purification by the technique such as silica gel column chromatography, partition column chromatography, gel filtration, a purification method with use of the difference of solubilities in a solvent or crystallization from a solvent gives a purified 6-(spicaminyl-amino)purine. The 6-(spicaminyl-amino) purine thus obtained has the chemical structure represented by the formula (IIa) and the following physicochemical properties:

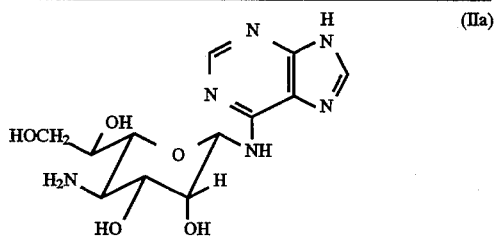
(IIa)

(1) Appearances: white powder,
(2) Melting point: 180–183° C.,
(3) Specific rotation: $[\alpha]_D^{25} = +1.2°$
(c = 0.25, in methanol),
(4) Elementary analysis:

| | Carbon | Hydrogen | Oxygen | Nitrogen |
|---|---|---|---|---|
| Calculated (%): | 44.17, | 5.56, | 24.52, | 25.75, |
| Observed (%): | 44.42, | 5.71, | 24.27, | 25.60. |

(5) Thin layer chromatography (with "Silica Gel 60F$_{254}$", Merck):
Developing solvent — Rf value
Butanol:acetic acid:water = 4:1:1 — 0.15

(6) Ultraviolet absorption spectra (maximum absorption):

In methanol solution: 264 nm ($E_{cm}^{1\%}$ 384),

In acidic methanol solution: 274 nm ($E_{cm}^{1\%}$ 392),

In alkaline methanol solution: 272 nm ($E_{cm}^{1\%}$ 341), (7) Infrared absorption spectrum (KBr disc method): 3400, 1650 cm$^{-1}$.

(8) FD mass spectrum (m/z) 327 (M+1)$^+$.

(9) Proton nuclear magnetic resonance spectrum (500 MHz, in CD$_3$OD+DCl): $\delta_H$: 3.43 (1H, dd, J=10.0, 10.0 Hz, H-4'), 3.62 (2H, m, H-7'), 3.72 (1H, dd, J=10.0, 10.0 Hz, H-5'), 3.80 (1H, m, H-6'), 3.89 (1H, dd, J=10.0, 3.1 Hz, H-3'), 4.07 (1H, dd, J=3.1, <1 Hz, H-2'), 5.72 (1H, brs, H-1'), 8.20 (1H, s, H-8), 8.40 (1H, s, H-2).

(10) Molecular formula: $C_{12}H_{18}O_5N_6$.

(11) Molecular weight: 326.3.

Preparation of the compound A:

For the preparation of the compound A according to the present invention, the compound 6-(4'-N-glycyl-spicaminyl-amino)purine (referred to hereinafter as the compound (IIIa)) represented by the following formula (III), in which glycine is bonded at the 4'-position in sugar of the aforementioned 6-(spicaminyl-amino)purine (referred to hereinafter as the compound (IIa)) can be used.

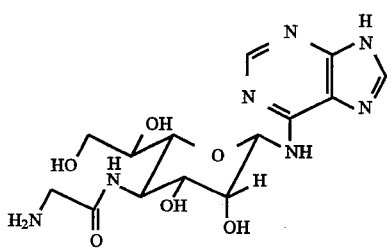
(IIIa)

In the preparation of the compound (IIIa), a compound in which an amino group of glycine is protected, for example, tert-butyloxycarbonyl-glycine is first treated by ordinary method as illustrated below to give an active ester, which is next stirred with 6-(spicaminyl-amino)purine (IIa) in an aprotic solvent such as N,N-dimethylformamide at room temperature, and the residue obtained by removing the solvent by distillation can be then subjected to an appropriate separation method such as column chromatography on an appropriate adsorbent, for example, silica gel, active charcoal or the like, to give 6-[4'-N-(N'-tert-butyloxycarbonyl-glycyl)spicaminyl-amino]purine. The active ester mentioned above can be obtained by a variety of well-known methods, for example, the method in which para-nitrophenol is added to tert-butyloxycarbonyl-glycine and N,N'-dicyclohexylcarbodiimide is further added as a condensation agent (see, for example, Pepuchido Gousei no Kiso To Jikken, p. 92, Maruzen, Japan).

6-[4'-N-(N-tert-butyloxycarbonylglycyl)spicaminyl-amino]purine thus obtained is treated with an acid such as trifluoroacetic acid or a methanolic hydrochloric acid solution to give a crude product of the deprotected compound (IIIa), which is then subjected to purification by the technique such as silica gel column chromatography, partition column chromatography, gel filtration, a purification method with use of the difference of solubilities in a solvent or crystallization from a solvent or the like to give 6-(4'-N-glycyl-spicaminyl-amino)purine [compound (IIIa)] or a salt thereof (the physicochemical properties of which are described hereinafter).

The compound A is obtained by reacting an active ester derivative, which is obtained by activating a variety of carboxylic acids (corresponding to the groups defined in (i)–(xi) for R in the formula (I)) by an ordinary method as described below, with 6-(4'-N-glycyl-septaminyl-amino)purine (compound (IIIb)) or an acid adduct thereof, for example, with an acid such as hydrochloric acid, under stirring in the presence of a base such as triethylamine or the like in an aprotic solvent such as N,N-dimethylformamide or the like (see, for example, Antimicrobial Agents and Chemotherapy, 845, 1965). The aforementioned activation of carboxylic acids can be carried out by converting the various carboxylic acids into corresponding active esters with use of para-nitrophenol, N-hydroxysuccinimide and a condensation agent, for example, N,N'-dicyclohexylcarbodiimide or the like (see, for example, Pepuchido Gousei no Kiso To Jikken, pp. 92–100, Maruzen, Japan). The spicamycin derivatives can be also obtained by reacting one of various carboxylic acids with a compound (IIIa) or a salt thereof by using a coupling agent such as N,N'-dicyclohexylcarbodiimide, diphenylphosphorylazide or the like in the presence of a base such as triethylamine or the like in an aprotic solvent (see, for example, Pepuchido Gousei no Kiso To Jikken, pp. 114–124, Maruzen, Japan).

Furthermore, the compound A can be also prepared as follows; Acylglycine compound is obtained by the method that the amino group of glycine is acylated with any acid halides of various carboxylic acids or by the method that glycine derivative in which the carboxylic acid has been protected is coupled with any carboxylic acids by use of a condensation agent and then the protective group is removed. The acylglycine is converted to the active ester, and it is condensed with the compound (IIa) or an acid adduct thereof.

The spicamycin derivative can be also prepared by condensing the acyl glycine compound and the compound (IIa) or an acid adduct thereof directly in an aprotic solvent or with use of a condensation agent such as N,N'-dicyclohexylcarbodiimide or 1-ethyl-3-(3-dimethylaminopropyl)carbodiimide hydrochloride in the presence of 1-hydroxybenzotriazole, N-hydroxysuccinimide or the like.

Physicochemical properties of 6-(4'-N-glycyl-spicaminyl-amino)purine (IIIa):

| (1) Appearances: | white powder, |
| (2) Melting point: | 195–198° C., |
| (3) Specific rotation: | $[\alpha]_D^{25} = +3.6°$ |
| | (c = 0.1, in methanol-water), |

| (4) Elementary analysis: | | | | |
| --- | --- | --- | --- | --- |
| | Carbon | Hydrogen | Oxygen | Nitrogen |
| Calculated (%): | 43.86, | 5.52, | 25.04, | 25.58, |
| Observed (%): | 43.57, | 5.80, | 24.77, | 25.86. |

| (5) Thin layer chromatography (with "Silica Gel 60F$_{254}$", Merck): | |
| --- | --- |
| Developing solvent | Rf value |
| Butanol:acetic acid:water = 4:1:1 | 0.10 |

(6) Ultraviolet absorption spectra: In methanol: 264 nm ($E_{cm}^{1\%}$ 328).

(7) Infrared absorption spectrum (KBr disc method): 3300, 1660 cm$^{-1}$.

(8) FD mass spectrum (m/z) 384 (M+1)$^+$.

(9) Proton nuclear magnetic resonance spectrum (500 MHz, in CD$_3$OD+DCl):

$\delta_H$: 3.60–3.90 (7H, m), 4.02 (1H, dd, J=3.0, <1 Hz, H-2'), 4.16 (1H, dd, J=10.0, 10.0 Hz, H-4'), 5.66 (1H, s, H-1'), 8.08 (1H, s, H-8), 8.28 (1H, s, H-2).

(2) The compounds represented by the formula (I) wherein R$_1$=OH and R$_2$=H (Compound B)

The spicamycin derivative of the present invention in this case can be presently prepared by the synthetic chemical modification of a septacidin aminonucleoside, referred to hereinafter as 6-(septaminyl-amino)purine, obtained by the hydrolysis of a mixture of septacidins produced by culturing a microorganism (see U.S. Pat. No. 3,155,647). Some septacidin derivatives can be obtained directly from a microbial culture by using an appropriate separation means. Further, the spicamycin derivatives of the present invention may be prepared by means of an overall synthetic chemical route.

The mixture of the septacidin are obtained from the culture of the *Streptomyces fimbrias* (ATCC 15051). The septacidin mixture can be obtained by the same method as spicamycin derivatives.

While the compound B according to the present invention can be obtained, as described above, by a variety of methods, the following method can be used as an example the specific production method of the compound.

Preparation of 6-(septaminyl-amino)purine:

6-(Septaminyl-amino)purine represented by the formula (IIb) below is prepared as crude product in a form of salt with any acid by hydrolyzing the septacidin mixture with suitable acid, for example, an inorganic acid such as hydrochloric acid or sulfuric acid, or an organic acid such as acetic acid or formic acid. Specifically, the crude product is obtained by dissolving or suspending a septacidin mixture in an alcoholic or aqueous solution of an acid such as hydrochloric acid and stirring the mixture at 20°–40° C. for 2–5 days. The neutralization and subsequent concentration of the crude product followed by the purification by the technique such as silica gel column chromatography, partition column chromatography, gel filtration, a purification method with use of the difference of solubilities in a solvent or crystallization from a solvent or the like gives a purified 6-(septaminyl-amino)purine. The 6-(septaminyl-amino) purine thus obtained has the chemical structure represented by the following formula (IIb) and physicochemical properties:

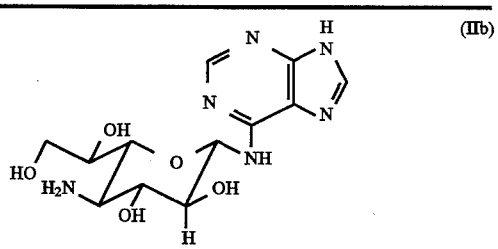

(IIb)

| (1) Appearances: | white powder, |
| (2) Melting point: | 119–120° C., |
| (3) Specific rotation: | $[\alpha]_D^{25} = +31.3°$ |
| | (c = 0.1, in methanol), |
| (4) Elementary analysis: | |

| | Carbon | Hydrogen | Oxygen | Nitrogen |
|---|---|---|---|---|
| Calculated (%): | 44.17, | 5.56, | 24.52, | 25.75, |
| Observed (%): | 44.36, | 5.82, | 24.31, | 25.51. |

(5) Thin layer chromatography (with "Silica Gel 60F$_{254}$", Merck):

| Developing solvent | Rf value |
|---|---|
| Butanol:acetic acid:water = 4:1:1 | 0.15 |

(6) Ultraviolet absorption spectra (maximum absorption): In methanol: 264 nm, (7) Infrared absorption spectrum (KBr disc method): 3400, 1650 cm$^{-1}$.

(8) FD mass spectrum (m/z) 327 (M+1)$^+$.

(9) Proton nuclear magnetic resonance spectrum (500 MHz, CD$_3$OD+DCl): $\delta_H$: 3.21 (1H, dd, J=10.0, 10.0 Hz, H-4'), 3.57 (1H, dd, 10.0, 10.0 Hz, H-2'), 3.63 (2H, brs, H-7'), 3.68 (1H, dd, J=10.0, 10.0 Hz, H-3'), 3.75–3.85 (2H, m, H-5', 6'), 5.58 (1H, s, H-1'), 8.19 (1H, s, H-8), 8.35 (1H, s, H-2).

(10) Molecular formula: $C_{12}H_{18}O_5N_6$.

(11) Molecular weight: 326.3.

Preparation of the compound B:

For the preparation of the compound B, the method used in the preparation of the derivative represented by the formula (I) as mentioned above can be used directly. That is, for the preparation of the compound B according to the present invention, the above 6-(4'-N-glycyl-septaminyl-amino)purine represented by the formula (IIIb) (referred to hereinafter as the compound (IIIb)) in which glycine is bonded at the 4'-position of the sugar in the aforementioned 6-(septaminyl-amino)purine (referred to hereinafter as the compound (IIb)) can be used.

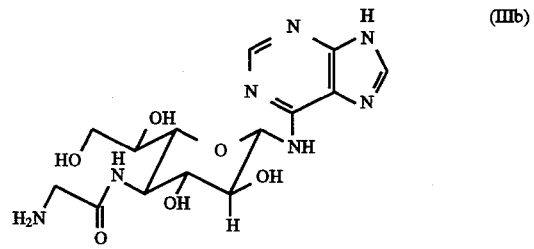

(IIIb)

In the preparation of the compound (IIIa), a compound in which an amino group of glycine is protected, for example, tert-butyloxycarbonyl-glycine is first treated in an ordinary method as illustrated below to give an active ester, which is next stirred with 6-(septaminyl-amino)purine (IIb) in an aprotic solvent such as N,N-dimethylformamide or the like at room temperature. The residue obtained by removing the solvent by distillation can be then subjected to an appropriate separation method such as column chromatography on an appropriate adsorbent, for example, silica gel, active charcoal or the like, to give 6-[4'-N-(N'-tert-butyloxycarbonylglycyl)septaminyl-amino]purine. The aforementioned active ester can be obtained by a variety of well-known methods, for example, a method in which para-nitrophenol is added to tert-butyloxycarbonyl-glycine and N,N'-dicyclohexylcarbodiimide is further added as a condensation agent.

6-[4'-N-(N'-tert-butyloxycarbonylglycyl)septaminyl-amino]purine thus obtained is treated with an acid such as trifluoroacetic acid or a methanolic hydrochloric acid solution and the resultant is deprotected to give a crude product of the compound (IIIb), which is then subjected to purification by the technique such as silica gel column chromatography, partition column chromatography, gel filtration, a purification method with use of the difference of solubilities in a solvent or crystallization from a solvent to give 6-(4'-N-glycyl-septaminyl-amino)purine [compound (IIIb)] or a salt thereof.

The compound B is obtained by reacting an active ester, which is obtained by activating any carboxylic acid (corresponding to the groups defined in (i)–(xi) for R in the formula (I)) by an ordinary method as illustrated below, with 6-(4'-N-glycyl-septaminyl-amino)purine (compound (IIIb)) or an acid adduct thereof (such as an acid adduct with an acid such as hydrochloric acid) under stirring in the presence of a base such as triethylamine or the like in an aprotic solvent such as N,N-dimethylformamide or the like. The aforementioned carboxylic acids can be activated, for example, by converting the various carboxylic acids to active esters with use of para-nitrophenol or N-hydroxysuccinimide and a condensation agent such as N,N'-dicyclohexylcarbodiimide or the like. The spicamycin derivative can be also obtained by reacting any carboxylic acid or a salt thereof with a coupling agent such as N,N'-dicyclohexylcarbodiimide, diphenylphosphorylazide or the like in the presence of a base such as triethylamine or the like in an aprotic solvent.

Furthermore, the compound B can be also prepared as follows; Acylglycine compound is obtained by the method that the amino group of glycine is acylated with any carboxylic halides of various carboxylic acids or by the method that glycine derivative in which the carboxylic acid has been protected is coupled with any carboxylic acids by use of a condensation agent and then the protective group is removed. The acylglycine is converted to the active ester, and it is condensed with the compound (IIb) or an acid adduct thereof.

The spicamycin derivative can be also prepared by condensing the acyl glycine compound and the compound (IIb) or an acid adduct thereof directly in an aprotic solvent or with use of a condensation agent such as N,N'-dicyclohexylcarbodiimide or 1-ethyl-3-(3-dimethylaminopropyl)carbodiimide hydrochloride in the presence of 1-hydroxybenzotriazole or N-hydroxysuccinimide or the like.

Physicochemical properties of 6-(4'-N-glycyl-septaminyl-amino)purine (IIIb):

| (1) Appearances: | white powder, |
| (2) Melting point: | 155–157° C., |
| (3) Specific rotation: | $[\alpha]_D^{25} = +12.4°$ |
| | (c = 0.1, in methanol), |

| (4) Elementary analysis: | | | | |
| --- | --- | --- | --- | --- |
| | Carbon | Hydrogen | Oxygen | Nitrogen |
| Calculated (%): | 43.86, | 5.52, | 25.04, | 25.58, |
| Observed (%): | 44.06, | 5.30, | 24.81, | 25.83. |

| (5) Thin layer chromatography (with "Silica Gel 60F$_{254}$", Merck): | |
| --- | --- |
| Developing solvent | Rf value |
| Butanol:acetic acid:water = 4:1:1 | 0.10 |

(6) Ultraviolet absorption spectra: In methanol: 264 nm.
(7) Infrared absorption spectrum (KBr disc method): 3300, 1660 cm$^{-1}$.
(8) FD mass spectrum (m/z) 384 (M+H)$^+$.
(9) Proton nuclear magnetic resonance spectrum (500 MHz, CD$_3$OD+DCl): $\delta_H$: 3.59 (1H, dd, J=10.0, 10.0 Hz, H-2'), 3.60–3.90 (7H, m), 3.96 (1H, dd, J=10.0, 10.0 Hz, H-4'), 5.40 (1H, brs, H-1'), 8.50 (1H, s, H-8), 8.60 (1H, s, H-2).

The structure of the preferred examples of the spicamycin derivatives according to the present invention can be shown as follows.

These compounds are those represented by the aforementioned formula (I) in which the group R is specifically represented. That is, the compounds have the structures in which the following groups are substituted for the group R of the formula (I).

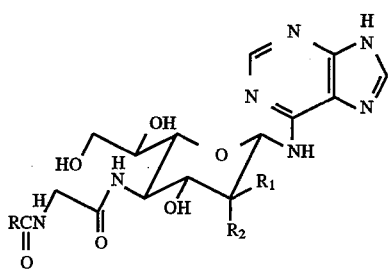
(I)

In this connection, the following (i)–(xi) correspond to the definitions (i)–(xi) mentioned in the description of the group R.

(1) Compound A (the compounds represented by the formula (I) wherein R$_1$=H and R$_2$=OH).

(i) Group R
(1) SPM6: CH$_3$(CH$_2$)$_8$—
   6-[4'-N-(N'-decanoylglycyl)spicaminyl-amino]purine,
(2) SPM9: CH$_3$(CH$_2$)$_{11}$—
   6-[4'-N-(N'-tridecanoylglycyl)spicaminyl-amino]purine,
(3) SPM10: CH$_3$(CH$_2$)$_{12}$—
   6-[4'-N-(N'-tetradecanoylglycyl)spicaminyl-amino]purine,
(4) SPM12: CH$_3$(CH$_2$)$_{14}$—
   6-[4'-N-(N'-hexadecanoylglycyl)spicaminyl-amino]purine,
(5) SPK9: (CH$_3$)$_2$CH(CH$_2$)$_8$—
   6-[4'-N-(N'-10-methylundecanoylglycyl)spicaminyl-amino]purine,
(6) SPK251: (CH$_3$)$_2$CH(CH$_2$)$_9$—
   6-[4'-N-(N'-11-methyldodecanoylglycyl)spicaminyl-amino]purine,
(7) SPK136: (CH$_3$)$_2$CH(CH$_2$)$_{10}$—
   6-[4'-N-(N'-12-methyltridecanoylglycyl)spicaminyl-amino]purine,
(8) SPK176: CH$_2$=CH(CH$_2$)$_8$—
   6-[4'-N-(N'-10-undecenoylglycyl)spicaminyl-amino]purine,
(9) SPK44: CH$_2$=CH(CH$_2$)$_9$—
   6-[4'-N-(N'-11-dodecenoylglycyl)spicaminyl-amino]purine,
(10) SPK142: CH$_2$=CH(CH$_2$)$_{10}$—
   6-[4'-N-(N'-12-tridecenoylglycyl)spicaminyl-amino]purine,
(11) SPK106: CH$_3$(CH$_2$)$_7$CH=CH(CH$_2$)$_7$—

(Z)

(Z: cis type)
   6-[4'-N-(N'-cis-9-octadecenoylglycyl)spicaminyl-amino]purine,
(12) SPK120: CH$_3$(CH$_2$)$_4$CH=CHCH$_2$CH=CH(CH$_2$)$_7$—

(Z) (Z)

6-[4'-N-(N'-cis,cis-9,12-octadecadienoyl-glycyl)spicaminyl-amino]purine,
(13) SPK 231: CH$_3$(CH$_2$)$_3$CH=CH(CH$_2$)$_7$—

(Z)

6-[4'-N-(N'-cis-9-tetradecenoylglycyl)spicaminyl-amino]purine,
(14) SPK148: CH$_3$(CH$_2$)$_5$CH=CH(CH$_2$)$_7$—

(Z)

6-[4'-N-(N'-cis-9-hexadecenoylglycyl)spicaminyl-amino]purine,
(15) SPK86: CH$_3$(CH$_2$)$_8$CH=CH—

(E)

(E: trans type)
   6-[4'-N-(N'-trans-2-dodecenoylglycyl)spicaminyl-amino]purine,
(16) SPK156: CH$_3$(CH$_2$)$_{10}$CH=CH—

(E)

6-[4'-N-(N'-trans-2-tetradecenoylglycyl)spicaminyl-amino]purine,

(17) SPK188: $CH_3(CH_2)_{12}CH=CH-$ (E)

6-[4'-N-(N'-trans-2-hexadecenoylglycyl)spicaminyl-amino]purine,
(18) SPK282: $CH_3(CH_2)_6CH=CHCH=CH-$ (E) (E)

6-[4'-N-(N'-trans,trans-2,4-dodecadienyl-glycyl) spicaminyl-amino]purine,
(19) SPK281: $CH_3(CH_2)_7CH=CHCH=CH-$ (E) (E)

6-[4'-N-(N'-trans,trans-2,4-tridecadienyl-glycyl) spicaminyl-amino]purine,
(20) SPK241: $CH_3(CH_2)_8CH=CHCH=CH-$ (E) (E)

6-[4'-N-(N'-trans,trans-2,4-tetradecadienyl-glycyl) spicaminyl-amino]purine,
(21) SPK285: $CH_3(CH_2)_9CH=CHCH=CH-$ (E) (E)

6-[4'-N-(N'-trans,trans-2,4-pentadecadienyl-glycyl) spicaminyl-amino]purine,
(22) SPK283: $CH_3(CH_2)_{10}CH=CHCH=CH-$ (E) (E)

6-[4'-N-(N'-trans,trans-2,4-hexadecadienyl-glycyl) spicaminyl-amino]purine,
(ii)
(23) SPK64: $Br(CH_2)_{10}-$
  6-[4'-N-(N'-11-bromoundecanoylglycyl)spicaminyl-amino]purine,
(24) SPK152: $Br(CH_2)_{11}-$
  6-[4'-N-(N'-12-bromododecanoylglycyl)spicaminyl-amino]purine,
(25) SPK276: $Br(CH_2)_{12}-$
  6-[4'-N-(N'-13-bromotridecanoylglycyl)spicaminyl-amino]purine,
(26) SPK273: $Br(CH_2)_{13}-$
  6-[4'-N-(N'-14-bromotetradecanoylglycyl)spicaminyl-amino]purine,
(27) SPK275: $Br(CH_2)_{14}-$
  6-[4'-N-(N'-15-bromopentadecanoylglycyl)spicaminyl-amino]purine,
(28) SPK272: $Br(CH_2)_{15}-$
  6-[4'-N-(N'-16-bromohexadecanoylglycyl)spicaminyl-amino]purine,
(29) SPK133: $Cl(CH_2)_{10}-$
  6-[4'-N-(N'-11-chloroundecanoylglycyl)spicaminyl-amino]purine,
(30) SPK132: $Cl(CH_2)_{11}-$
  6-[4'-N-(N'-12-chlorododecanoylglycyl)spicaminyl-amino]purine,
(31) SPK278: $Cl(CH_2)_{12}-$
  6-[4'-N-(N'-13-chlorotridecanoylglycyl)spicaminyl-amino]purine,
(32) SPK280: $Cl(CH_2)_{13}-$
  6-[4'-N-(N'-14-chlorotetradecanoylglycyl)spicaminyl-amino]purine,
(33) SPK277: $Cl(CH_2)_{14}-$
  6-[4'-N-(N'-15-chloropentadecanoylglycyl)spicaminyl-amino]purine,
(34) SPK146: $F(CH_2)_{11}-$
  6-[4'-N-(N'-12-fluorododecanoylglycyl)spicaminyl-amino]purine,
(35) SPK279: $F(CH_2)_{13}-$
  6-[4'-N-(N'-14-fluorotetradecanoylglycyl)spicaminyl-amino]purine,
(36) SPK247: $F(CH_2)_{14}-$
  6-[4'-N-(N'-15-fluoropentadecanoylglycyl)spicaminyl-amino]purine,
(37) SPK157: $F(CH_2)_{15}-$
  6-[4'-N-(N'-16-fluorohexadecanoylglycyl)spicaminyl-amino]purine,
(38) SPK165: $I(CH_2)_{10}-$
  6-[4'-N-(N'-11-iodoundecanoylglycyl)spicaminyl-amino]purine,
(39) SPK258: $CH_3(CH_2)_{11}CHBr-$
  6-[4'-N-(N'-2-bromotetradecanoylglycyl)spicaminyl-amino]purine,
(40) SPK153: $CH_3(CH_2)_{13}CHBr-$
  6-[4'-N-(N'-2-bromohexadecanoylglycyl)spicaminyl-amino]purine,
(41) SPK175: $CH_3(CH_2)_9CHCl-$
  6-[4'-N-(N'-2-chlorododecanoylglycyl)spicaminyl-amino]purine,
(42) SPK259: $CH_3(CH_2)_{11}CHCl-$
  6-[4'-N-(N'-2-chlorotetradecanoylglycyl)spicaminyl-amino]purine,
(43) SPK135: $CH_3(CH_2)_{13}CHCl-$
  6-[4'-N-(N'-2-chlorohexadecanoylglycyl)spicaminyl-amino]purine,
(44) SPK159: $CH_3(CH_2)_9CHF-$
  6-[4'-N-(N'-2-fluorododecanoylglycyl)spicaminyl-amino]purine,
(45) SPK233: $CH_3(CH_2)_{13}CHF-$
  6-[4'-N-(N'-2-fluorohexadecanoylglycyl)spicaminyl-amino]purine,
(iii)
(46) SPK182: $CH_3(CH_2)_{11}CF_2-$
  6-[4'-N-(N'-2,2-difluorotetradecanoylglycyl)-spicaminyl-amino]purine,
(47) SPK193: $CH_3(CH_2)_{13}CF_2-$
  6-[4'-N-(N'-2,2-difluorohexadecanoylglycyl)-spicaminyl-amino]purine,
(48) SPK87: $CH_3(CH_2)_9CH(OH)-$
  6-[4'-N-(N'-2-hydroxydodecanoylglycyl)spicaminyl-amino]purine,
(49) SPK 112: $CH_3(CH_2)_{13}CH(OH)-$
  6-[4'-N-(N'-2-hydroxyhexadecanoylglycyl)spicaminyl-amino]purine, (R)

(50) SPK256: $CH_3(CH_2)_{13}CH(OH)-$
  6-[4'-N-(N'-(R)-2-hydroxyhexadecanoylglycyl)-spicaminyl-amino]purine, (S)

(51) SPK 271: $CH_3(CH_2)_{13}CH(OH)-$
  6-[4'-N-(N'-(S)-2-hydroxyhexadecanoylglycyl)-spicaminyl-amino]purine,
(52) SPK88: $CH_3(CH_2)_8CH(OH)CH_2-$
  6-[4'-N-(N'-3-hydroxydodecanoylglycyl)spicaminyl-amino]purine, (R)

(53) SPK270: $CH_3(CH_2)_{10}CH(OH)CH_2-$
  6-[4'-N-(N'-(R)-3-hydroxytetradecanoylglycyl)-spicaminyl-amino]purine, (S)

(54) SPK274: $CH_3(CH_2)_{10}CH(OH)CH_2$—
6-[4'-N-(N'-(S)-3-hydroxytetradecanoylglycyl)-spicaminyl-amino]purine,

(55) SPK115: $CH_3(CH_2)_{12}CH(OH)CH_2$—
6-[4'-N-(N'-3-hydroxyhexadecanoylglycyl)-spicaminyl-amino]purine, (iv)

(56) SPK126: $N_3(CH_2)_{10}$—
6-[4'-N-(N'-11-azidoundecanoylglycyl)-spicaminyl-amino]purine,

(57) SPK410: $N_3(CH_2)_{11}$—
6-[4'-N-(N'-12-azidododecanoylglycyl)-spicaminyl-amino]purine,

(58) SPK252: $N_3(CH_2)_{14}$—
6-[4'-N-(N'-15-azidopentadecanoylglycyl)-spicaminyl-amino]purine,

(59) SPK226: $N_3(CH_2)_{15}$—
6-[4'-N-(N'-16-azidohexadecanoylglycyl)-spicaminyl-amino]purine,

(60) SPK229: $CH_3(CH_2)_{13}CHN_3$—
6-[4'-N-(N'-2-azidohexadecanoylglycyl)-spicaminyl-amino]purine,

(61) SPK416: $CN(CH_2)_{10}$—
6-[4'-N-(N'-11-cyanoundecanoylglycyl)-spicaminyl-amino]purine,

(62) SPK177: $CN(CH_2)_{15}$—
6-[4'-N-(N'-16-cyanohexadecanoylglycyl)-spicaminyl-amino]purine, (v)

(63) SPK422:

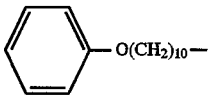

6-[4'-N-(N'-11-phenoxyundecanoylglycyl)-spicaminyl-amino]purine,

(64) SPK249:

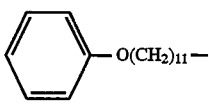

6-[4'-N-(N'-12-phenoxydodecanoylglycyl)-spicaminyl-amino]purine,

(65) SPK242:

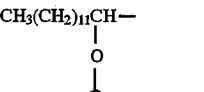

6-[4'-N-(N'-2-phenoxytetradecanoylglycyl)-spicaminyl-amino]purine,

(66) SPK186:

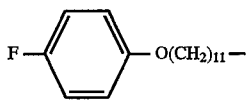

6-[4'-N-(N'-12-para-fluorophenoxydodecanoylglycyl)-spicaminyl-amino]purine, (vi)

(67) SPK228:

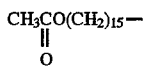

6-[4'-N-(N'-16-acetoxyhexadecanoylglycyl)-spicaminyl-amino]purine,

(68) SPK173:

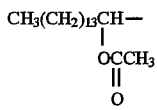

6-[4'-N-(N'-2-acetoxyhexadecanoylglycyl)-spicaminyl-amino]purine,

(69) SPK197:

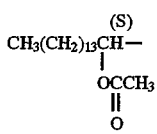

6-[4'-N-(N'-(S)-2-acetoxyhexadecanoylglycyl)-spicaminyl-amino]purine,

(70) SPK198:

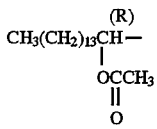

6-[4'-N-(N'-(R)-2-acetoxyhexadecanoylglycyl)-spicaminyl-amino]purine,

(71) SPK189:

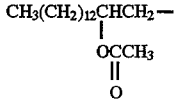

6-[4'-N-(N'-3-acetoxyhexadecanoylglycyl)-spicaminyl-amino]purine,

(72) SPK184:

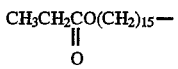

6-[4'-N-(N'-16-propionyloxyhexadecanoylglycyl)-spicaminyl-amino]purine,

(73) SPK145:

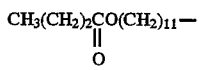

6-[4'-N-(N'-12-butyryloxydodecanoylglycyl)-spicamynyl-amino]purine, (vii)

(74) SPK225: $CH_3SO_2O(CH_2)_{15}$—

6-[4'-N-(N'-16-methanesulfonyloxyhexadecanoyl-glycyl)-spicaminyl-amino]purine,

(75) SPK230: $CH_3(CH_2)_2SO_2O(CH_2)_{11}$—

6-[4'-N-(N'-12-propanesulfonyloxydodecanoylglycyl)-spicaminyl-amino]purine,

(76) SPK232: $CH_3(CH_2)_3SO_2O(CH_2)_{11}$—

6-[4'-N-(N'-12-butanesulfonyloxydodecanoylglycyl)-spicaminyl-amino]purine,

(77) SPK185:

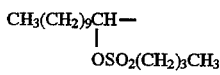

6-[4'-N-(N'-2-butanesulfonyloxydodecanoylglycyl)-spicaminyl-amino]purine, (viii)

(78) SPK429: $(CH_3)_3Si—C\equiv C—(CH_2)_8$—

6-[4'-N-(N'-11-trimethylsilyl-10-undecynoylglycyl)-spicaminyl-amino]purine,

(79) SPK430: $(CH_3)_3Si(CH_2)_{10}$—

6-[4'-N-(N'-11-trimethylsilylundecanoylglycyl)-spicaminyl-amino]purine, (ix)

(80) SPK123:

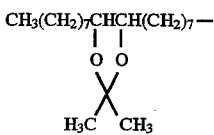

6-[4'-N-(N'-9,10-dioxy-9,10-O-isopropylidene-octadecanoylglycyl)-spicaminyl-amino]purine, (x)

(81) SPK102:

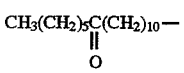

6-[4'-N-(N'-12-oxostearoylglycyl)-spicaminyl-amino]purine, (xi)

(82) SPK262:

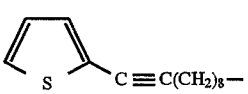

6-{4'-N-[N'-11-(2'-thienyl)-10-undecynoylglycyl]-spicaminyl-amino}purine,

(83) SPK263:

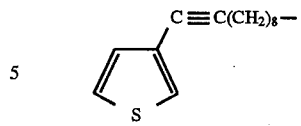

6-{4'-N-[N'-11-(3'-thienyl)-10-undecynoylglycyl]-spicaminyl-amino}purine,

(84) SPK266:

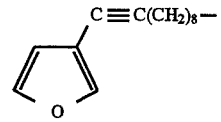

6-{4'-N-[N'-11-(3'-furyl)-10-undecynoylglycyl]-spicaminyl-amino}purine,

The spicamycin derivatives of the present invention containing the aforementioned preferred compounds can be converted into acid adduct salts and base adduct salts as described above by the usual way.

(2) Compound B (compound of the formula (I) wherein $R_1$=OH and $R_2$=H)

(i) Group R (1) SPTM6: $CH_3(CH_2)_8$—

6-[4'-N-(N'-decanoylglycyl)-septaminyl-amino]purine, (2) SPTM9: $CH_3(CH_2)_{11}$—

6-[4'-N-(N'-tridecanoylglycyl)-septaminyl-amino]purine, (3) SPTM10: $CH_3(CH_2)_{12}$—

6-[4'-N-(N'-tetradecanoylglycyl)-septaminyl-amino] purine, (4) SPTM12: $CH_3(CH_2)_{14}$—

6-[4'-N-(N'-hexadecanoylglycyl)-septaminyl-amino] purine, (5) SPT9: $(CH_3)_2CH(CH_2)_8$—

6-[4'-N-(N'-10-methylundecanoylglycyl)-septaminyl-amino]purine, (6) SPT251: $(CH_3)_2CH(CH_2)_9$—

6-[4'-N-(N'-11-methyldodecanoylglycyl)-septaminyl-amino]purine, (7) SPT136: $(CH_3)_2CH(CH_2)_{10}$—

6-[4'-N-(N'-12-methyltridecanoylglycyl)-septaminyl-amino]purine, (8) SPT176: $CH_2=CH(CH_2)_8$—

6-[4'-N-(N'-10-undecenoylglycyl)-septaminyl-amino] purine, (9) SPT44: $CH_2=CH(CH_2)_9$—

6-[4'-N-(N'-11-dodecenoylglycyl)-septaminyl-amino] purine,

(10) SPT142: $CH_2=CH(CH_2)_{10}$—

6-[4'-N-(N'-12-tridecenoylglycyl)-septaminyl-amino] purine,

(11) SPT120: $CH_3(CH_2)_4CH=CHCH_2CH=CH(CH_2)_7$—

(Z) (Z)

6-[4'-N-(N'-cis,cis-9,12-octadecadienoylglycyl)-septaminyl-amino]purine,

(12) SPT231: $CH_3(CH_2)_3CH=CH (CH_2)_7$—

(Z)

6-[4'-N-(N'-cis-9-tetradecenoylglycyl)-septaminyl-amino]purine,

(13) SPT148: $CH_3(CH_2)_5CH=CH(CH_2)_7—$ (z)

6-[4'-N-(N'-cis-9-hexadecenoylglycyl)-septaminyl-aminolpurine,

(14) SPT86: $CH_3(CH_2)_8CH=CH—$ (E)

(E: trans form)
6-[4'-N-(N'-trans-2-dodecenoylglycyl)-septaminyl-aminolpurine,

(15) SPT56: $CH_3(CH_2)_{10}CH=CH—$ (E)

6-[4'-N-(N'-trans-2-tetradecenoylglycyl)-septaminyl-aminolpurine,

(16) SPT188: $CH_3(CH_2)_{12}CH=CH—$ (E)

6-[4'-N-(N'-trans-2-hexadecenoylglycyl)-septaminyl-aminolpurine,

(17) SPT282: $CH_3(CH_2)_6CH=CHCH=CH—$ (E) (E)

6-[4'-N-(N'-trans,trans-2,4-dodecadienylglycyl)-septaminyl-aminolpurine,

(18) SPT281: $CH_3(CH_2)_7CH=CHCH=CH—$ (E) (E)

6-[4'-N-(N'-trans,trans-2,4-tridecadienylglycyl)-septaminyl-aminolpurine,

(19) SPT241: $CH_3(CH_2)_8CH=CHCH=CH—$ (E) (E)

6-[4'-N-(N'-trans,trans-2,4-tetradecadienylglycyl)-septaminyl-aminolpurine,

(20) SPT285: $CH_3(CH_2)_9CH=CHCH=CH—$ (E) (E)

6-[4'-N-(N'-trans,trans-2,4-pentadecadienylglycyl)-septaminyl-aminolpurine,

(21) SPT283: $CH_3(CH_2)10CH=CHCH=CH—$ (E) (E)

6-[4'-N-(N'-trans,trans-2,4-hexadecadienylglycyl)-septaminyl-aminolpurine, (ii)

(22) SPT64: $Br(CH_2)_{10}—$
6-[4'-N-(N'-11-bromoundecadienylglycyl)-septaminyl-aminolpurine,

(23) SPT152: $Br(CH_2)_{11}—$
6-[4'-N-(N'-12-bromododecanonylglycyl)-septaminyl-aminolpurine,

(24) SPT276: $Br(CH_2)_{12}—$
6-[4'-N-(N'-13-bromotridecanonylglycyl)-septaminyl-aminolpurine,

(25) SPT273: $Br(CH_2)_{13}—$
6-[4'-N-(N'-14-bromotetradecanonylglycyl)-septaminyl-aminolpurine,

(26) SPT275: $Br(CH_2)_{14}—$
6-[4'-N-(N'-15-bromopentadecanonylglycyl)-septaminyl-aminolpurine,

(27) SPT272: $Br(CH_2)_{15}—$
6-[4'-N-(N'-16-bromohexadecanonylglycyl)-septaminyl-aminolpurine,

(28) SPT133: $Cl(CH_2)_{10}—$
6-[4'-N-(N'-11-chloroundecanoylglycyl)-septaminyl-aminolpurine,

(29) SPT132: $Cl(CH_2)_{11}—$
6-[4'-N-(N'-12-chlorododecanoylglycyl)-septaminyl-aminolpurine,

(30) SPT278: $Cl(CH_2)_{12}—$
6-[4'-N-(N'-13-chlorotridecanoylglycyl)-septaminyl-aminolpurine,

(31) SPT280: $Cl(CH_2)_{13}—$
6-[4'-N-(N'-14-chlorotetradecanoylglycyl)-septaminyl-aminolpurine,

(32) SPT277: $Cl(CH_2)_{14}—$
6-[4'-N-(N'-15-chloropentadecanoylglycyl)-septaminyl-aminolpurine,

(33) SPT146: $F(CH_2)_{11}—$
6-[4'-N-(N'-12-fluorododecanoylglycyl)-septaminyl-aminolpurine,

(34) SPT279: $F(CH_2)_{13}—$
6-[4'-N-(N'-14-fluorotetradecanoylglycyl)-septaminyl-aminolpurine,

(35) SPT247: $F(CH_2)_{14}—$
6-[4'-N-(N'-15-fluoropentadecanoylglycyl)-septaminyl-aminolpurine,

(36) SPT157: $F(CH_2)_{15}—$
6-[4'-N-(N'-16-fluorohexadecanoylglycyl)-septaminyl-aminolpurine,

(37) SPT165: $I(CH_2)_{10}—$
6-[4'-N-(N'-11-iodoundecanoylglycyl)-septaminyl-aminolpurine,

(38) SPT258: $CH_3(CH_2)_{11}CHBr—$
6-[4'-N-(N'-2-bromotetradecanonylglycyl)-septaminyl-aminolpurine,

(39) SPT153: $CH_3(CH_2)_{13}CHBr—$
6-[4'-N-(N'-2-bromohexadecanonylglycyl)-septaminyl-aminolpurine,

(40) SPT175: $CH_3(CH_2)_9CHCl—$
6-[4'-N-(N'-2-chlorododecanonylglycyl)-septaminyl-aminolpurine,

(41) SPT259: $CH_3(CH_2)_{11}CHCl—$
6-[4'-N-(N'-2-chlorotetradecanonylglycyl)-septaminyl-aminolpurine,

(42) SPT135: $CH_3(CH_2)_{13}CHCl—$
6-[4'-N-(N'-2-chlorohexadecanonylglycyl)-septaminyl-aminolpurine,

(43) SPT159: $CH_3(CH_2)_9CHF—$
6-[4'-N-(N'-2-fluorododecanonylglycyl)-septaminyl-aminolpurine,

(44) SPT233: $CH_3(CH_2)_{13}CHF—$
6-[4'-N-(N'-2-fluorohexadecanonylglycyl)-septaminyl-aminolpurine,

(45) SPT182: $CH_3(CH_2)_{11}CHF_2—$
6-[4'-N-(N'-2,2-difluorotetradecanonylglycyl)-septaminyl-aminolpurine,

(46) SPT193: $CH_3(CH_2)_{13}CHF_2—$
6-[4'-N-(N'-2,2-difluorohexadecanonylglycyl)-septaminyl-aminolpurine, (iii)

(47) SPT87: $CH_3(CH_2)_9CH(OH)—$
6-[4'-N-(N'-2-hydroxydodecanonylglycyl)-septaminyl-aminolpurine,

(48) SPT112: $CH_3(CH_2)_{13}CH(OH)—$
6-[4'-N-(N'-2-hydroxyhexadecanoylglycyl)-septaminyl-aminolpurine,

(49) SPT112: CH$_3$(CH$_2$)$_{13}$CH(OH)— (R)
  6-[4'-N-(N'-(R)-2-hydroxyhexadecanoylglycyl)-septaminyl-amino]purine,

(50) SPT271: CH$_3$(CH$_2$)$_{13}$CH(OH)— (S)
  6-[4'-N-(N'-(S)-2-hydroxyhexadecanoylglycyl)-septaminyl-amino]purine,

(51) SPT88: CH$_3$(CH$_2$)$_8$CH(OH)CH$_2$—
  6-[4'-N-(N'-3-hydroxydodecanoylglycyl)-septaminyl-amino]purine,

(52) SPT270: CH$_3$(CH$_2$)$_{10}$CH(OH)CH$_2$— (R)
  6-[4'-N-(N'-(R)-3-hydroxytetradecanoylglycyl)-septaminyl-amino]purine,

(53) SPT274: CH$_3$(CH$_2$)$_{10}$CH(OH)CH$_2$— (S)
  6-[4'-N-(N'-(S)-3-hydroxytetradecanoylglycyl)-septaminyl-amino]purine,

(54) SPT115: CH$_3$(CH$_2$)$_{12}$CH(OH)CH$_2$—
  6-[4'-N-(N'-3-hydroxyhexadecanoylglycyl)-septaminyl-amino]purine, (iv)
(55) SPT410: N$_3$(CH$_2$)$_{10}$—
  6-[4'-N-(N'-11-azidoundecanoylglycyl)-septaminyl-amino]purine,

(56) SPT126: N$_3$(CH$_2$)$_{11}$—
  6-[4'-N-(N'-12-azidododecanoylglycyl)-septaminyl-amino]purine,

(57) SPT252: N$_3$(CH$_2$)$_{14}$—
  6-[4'-N-(N'-15-azidopentadecanoylglycyl)-septaminyl-amino]purine,

(58) SPT226: N$_3$(CH$_2$)$_{15}$—
  6-[4'-N-(N'-16-azidohexadecanoylglycyl)-septaminyl-amino]purine,

(59) SPT229: CH$_3$(CH$_2$)$_{13}$CHN—
  6-[4'-N-(N'-2-azidohexadecanoylglycyl)-septaminyl-amino]purine,

(60) SPT416: CN(CH$_2$)$_{10}$—
  6-[4'-N-(N'-11-cyanoundecanoylglycyl)-septaminyl-amino]purine,

(61) SPT177: CN(CH$_2$)$_{15}$—
  6-[4'-N-(N'-16-cyanohexadecanoylglycyl)-septaminyl-amino]purine, (v)
(62) SPT422:

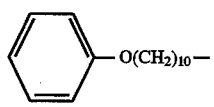

6-[4'-N-(N'-11-phenoxyundecanoylglycyl)-septaminyl-amino]purine,

(63) SPT249:

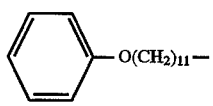

6-[4'-N-(N'-12-phenoxydodecanoylglycyl)-septaminyl-amino]purine,

(64) SPT242:

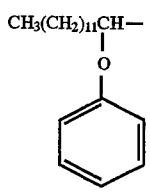

6-[4'-N-(N'-2-phenoxytetradecanoylglycyl)-septaminyl-amino]purine,

(65) SPT186:

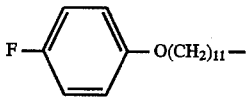

6-[4'-N-(N'-12-para-fluorophenoxydodecanoylglycyl)-septaminyl-amino]purine, (vi)
(66) SPT228:

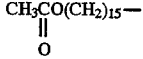

6-[4'-N-(N'-16-acetoxyhexadecanoylglycyl)-septaminyl-amino]purine,

(67) SPT173:

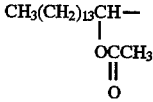

6-[4'-N-(N'-2-acetoxyhexadecanoylglycyl)-septaminyl-amino]purine,

(68) SPT197:

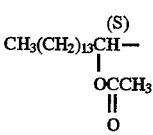

6-[4'-N-(N'-(S)-2-acetoxyhexadecanoylglycyl)-septaminyl-amino]purine,

(69) SPT198:

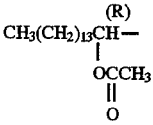

6-[4'-N-(N'-(R)-2-acetoxyhexadecanoylglycyl)-septaminyl-amino]purine,

(70) SPT189:

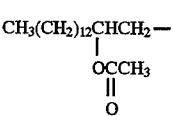

6-[4'-N-(N'-3-acetoxyhexadecanoylglycyl)-septaminyl-amino]purine,

(71) SPT184:

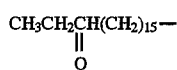

6-[4'-N-(N'-16-propionyloxyhexadecanoylglycyl)-septaminyl-amino]purine,

(72) SPT145:

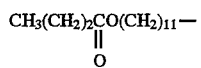

6-[4'-N-(N'-12-butyryloxydodecanoylglycyl)-septaminyl-amino]purine, (vii)

(73) SPT225: $CH_3SO_2O(CH_2)_{15}$—

6-[4'-N-(N'-16-methanesulfonyloxydodecanoylglycyl)-septaminyl-amino]purine,

(74) SPT230: $CH_3(CH_2)_2SO_2O(CH_2)11$—

6-[4'-N-(N'-12-propanesulfonyloxydodecanoylglycyl)-septaminyl-amino]purine,

(75) SPT232: $CH_3(CH_2)_3SO_2O(CH_2)_{11}$—

6-[4'-N-(N'-12-butanesulfonyloxydodecanoylglycyl)-septaminyl-amino]purine,

(76) SPT185:

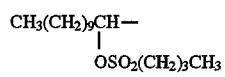

6-[4'-N-(N'-2-butanesulfonyloxydodecanoylglycyl)-septaminyl-amino]purine, (viii)

(77) SPT429: $(CH_3)_3Si-C{\equiv}C-(CH_2)_8$—

6-[4'-N-(N'-11-trimethylsilyl-10-undecynoylglycyl)-septaminyl-amino]purine,

(78) SPT430: $(CH_3)_3Si(CH_2)_{10}$—

6-[4'-N-(N'-11-trimethylsilylundecanoylglycyl)-septaminyl-amino]purine, (ix)

(79) SPT123:

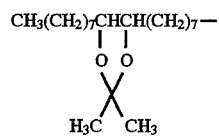

6-[4'-N-(N'-9,10-dioxy-9,10-O-isopropylidene-octadecanoylglycyl)-septaminyl-amino]purine, (x)

(80) SPT102:

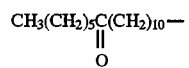

6-[4'-N-(N'-12-oxostearoylglycyl)-septaminyl-amino]purine, (xi)

(81) SPT262:

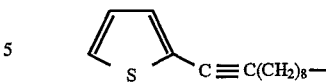

6-{4'-N-[N'-11-(2'-thienyl)-10-undecynoylglycyl]-septaminyl-amino}purine,

(82) SPT263:

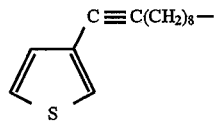

6-{4'-N-[N'-11-(3'-thienyl)-10-undecynoylglycyl]-septaminyl-amino}purine,

(83) SPT266:

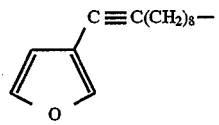

6-{4'-N-[N'-11-(3'-furyl)-10-undecynoylglycyl]-septaminyl-amino}purine,

The spicamycin derivatives of the present invention containing the aforementioned preferred compounds can be converted into acid adduct salts and base adduct salts as described above by the usual way.

Uses of Spicamycin Derivatives

The spicamycin compounds according to the present invention are useful in the point that the exhibit antitumor activity in the human tumor xenograft model which reflect the clinical effect.

Antitumor activity:

(1) Measurement of maximum toleraed dose (MTD) of the spicamycin derivatives in nude mice The spicamycin derivative was dissolved in dimethylsulfoxide (DMSO) and Cremophor EL® at the same volume as DMSO was added. Physiological saline was added so that the concentration of DMSO and Cremophor EL® was finally adjusted to 1%, respectively, and thus injection liquids of spicamycin derivative in a variety of concentrations were prepared. After these liquids were administered intravenously to untreated nude mice (BALB/c nu/nu, female, 6 weeks old) at a dose of 0.01 ml/g of body weight/day for continuous 5 days, and life or death of the animals was observed for 2 weeks. The maximum dose at which no animal was dead was defined as the MTD of the respective derivatives.

(2) Method for measuring the antitumor effect on human colon cancer (COL-1)

COL-1, a human colon cancer, was transplanted subcutaneously into nude mice. When the tumor had grown to a volume of about 100 mm³, the nude mice were divided into groups of 5 animals so that the average tumor volumes of respective groups were equalized. The respective spicamycin derivatives were administered to test groups at their MTDs, while physiological saline (solvent) containing 1% DMSO and 1% Cremophor EL® was administered to the control group. The tumor growth inhibition rate (TGIR) was calculated from the equation: TGIR=(1−Tx/Cx)×100, provided that, the relative tumor volume (RV) of the control group at the day X is designated as Cx and the tumor volume of the group at the day X to which a spicamycin derivative had been administered is designated as Tx. RV is expressed as RV=Vn/Vo where Vn is the tumor volume on day n and Vo is the initial tumor volume at the time treatment was commenced.

The maximum TGIRs obtained during the test period of about 3 weeks are shown in the following table. Also, the minTxs (the relative tumor volume when the tumor volume was reduced to the minimum throughout the test period) for some spicamycin derivatives are shown in the table.

Furthermore, the minimum effective dose (the term "effective" being intended to mean effective when TGIR≧50) was obtained and the therapeutic index was calculated from the equation: therapeutic index=maximum effective dose (MTD)/minimum effective dose for some spicamycin derivatives. The results are also shown in the table.

Table: Maximum tolerated doses, tumor growth inhibition rate, tumor reducing effect and therapeutic index of spicamycin derivatives against to human colon cancer (COL-1)

| Sample | Maximum tolerated dose (mg/kg/day) | TGIR | minTx | Therapeutic index |
| --- | --- | --- | --- | --- |
| SPM8 (Spicamycin X) | 10.4 | 94 | 0.19 | 4 |
| SPM9 | 3.4 | 99 | 0.05 | 6 |
| SPM10 | 2.6 | 98 | 0.10 | 4 |
| SPK9 | 6 | 99 | 0.05 | 4 |
| SPK44 | 4 | 94 | 0.16 | 4 |
| SPK64 | 18 | 95 |  | 4 |
| SPK86 | 18 | 86 |  | 4 |
| SPK112 | 0.85 | 82 |  | 4 |
| SPK115 | 3 | 99 | 0.08 | 4 |
| SPK132 | 12 | 98 | 0.08 | 4 |
| SPK135 | 24 | 93 |  | 4 |
| SPK136 | 2 | 84 |  | 4 |
| SPK142 | 6 | 99 | 0.09 | 4 |
| SPK148 | 3.4 | 94 | 0.21 | 4 |
| SPK152 | 36 | 100 | 0.03 | 8 |
| SPK156 | 3 | 92 |  | 4 |
| SPK157 | 1.6 | 98 | 0.11 | 4 |
| SPK159 | 24 | 96 |  | 4 |
| SPK165 | 24 | 86 |  |  |
| SPK177 | 13.5 | 99 |  | 4 |
| SPK182 | 36 | 90 | 0.24 | 8 |
| SPK188 | 0.6 | 92 |  |  |
| SPK189 | 6 | 98 | 0.09 | 4 |
| SPK198 | 1.5 | 82 |  |  |
| SPK231 | 6 | 96 | 0.12 | 6 |
| SPK232 | 24 | 96 |  | 4 |
| SPK233 | 2.7 | 96 | 0.13 | 4 |
| SPK241 | 6 | 97 | 0.14 | 16 |
| SPK247 | 6 | 96 | 0.16 | 8 |
| SPK249 | 3 | 88 | 0.26 | 4 |
| SPK251 | 6 | 97 |  | 8 |
| SPK262 | 8 | 99 | 0.03 | 4 |
| SPK263 | 12 | 97 | 0.09 | 8 |
| SPK266 | 12 | 97 | 0.18 | 8 |
| SPK270 | 12 | 94 | 0.21 | 4 |
| SPK271 | 2 | 99 | 0.09 | 8 |
| SPK273 | 12 | 98 | 0.11 | 8 |
| SPK274 | 24 | 92 | 0.16 | 4 |
| SPK276 | 12 | 96 | 0.16 | 8 |
| SPK278 | 12 | 92 | 0.21 | 8 |
| SPK278 | 6 | 93 | 0.25 | 8 |
| SPK280 | 9 | 94 | 0.19 | 8 |
| SPK281 | 18 | 99 | 0.06 | 8 |
| SPK282 | 36 | 99 | 0.07 | 16 |
| SPK422 | 3.4 | 95 |  | 4 |
| SPT241 | 3 | 93 | 0.24 | 8 |

As described above, the spicamycin derivatives according to the present invention exhibited excellent antitumor effects on the human colon cancer (COL-1). Acute toxicity ($LD_{50}$):

Various concentrations of SPK241 were administered intravenously into 10 ICR mice (female, 6 weeks old) per group, and the life or death of the animals were observed for 14 days after the administration of the drug. The $LD_{50}$ was obtained from the mortalities at the respective dosage groups by the Litchfield and Wilcoxon's method. As a result, SPK241 showed the $LD_{50}$ of 110 mg/kg.

Antitumor agent:

It has thus been elucidated that the spicamycin derivatives according to the present invention exhibit antitumor effective against the human tumor transplanted into the nude mice.

As described above, the compounds of the present invention has a property of exhibiting an excellent antitumor effective and a high therapeutic index. As for the antitumor activity, the compounds of the present invention may have an advantage of having a wide antitumor spectrum.

Accordingly, the compound of the present invention can be used as an antitumor agent or a tumor treating agent.

The compound of the present invention which is used as an antitumor agent can be administered via any appropriate dosage routes, specifically, in the case of animals intraperitoneally, subcutaneously, intravenously or intraarterially or topically by injection and in the case of humans intravenously, intraarterially, topically by injection, intraperitoneally, intrapleurally, orally, subcutaneously, intramuscularly, sublingually, intraepidermally or rectally.

When the compound of the present invention is administered as a drug, it can be administered in the form of injection, suspension, tablets, granules, powder, capsules, ointment, cream or the like depending on the dosage methods or dosage designs. In the preparation of these pharmaceuticals, a solvent, solubilizing agent, agent for making isotonicity, preservative, antioxidizing agent, excipient, binders, lubricants, stabilizing agent or the like can be added.

The examples of the solvent are water, physiological saline and the like; the examples of the solubilizing agent are ethanol, Polysorbates, Cremophor EL® and the like; the examples of the excipient are lactose, starch, crystalline cellulose, mannitol, maltose, calcium hydrogen phosphate, light silicic acid anhydride, calcium carbonate and the like; the examples of the binder are starch, Polyvinylpyrrolidone, hydroxypropyl cellulose, ethyl cellulose, carboxymethyl cellulose, gum arabic and the like; the examples of the disintegrator are starch, carboxylmethyl cellulose calcium and the like; the examples of the lubricating agent are magnesium stearate, talc, hardened oils and the like; the examples of the stabilizer are lactose, mannitol, maltose, Polysorbates, Macrogols, polyoxyethylene hardened castor oils and the like. If necessary, glycerin, dimethylacetamide, 70% sodium lactate, a surfactant or a basic substance such as sodium hydroxide, ethylenediamine, ethanolamine, sodium carbonate, arginine, meglumine or trisaminomethane is added. Pharmaceutical preparations such as injections, tablets, granules or capsules can be formed with these components.

The dose of the compound of the present invention is determined in consideration of the results of animal experiments and various conditions so that the total dose will not exceed the certain amount at single or repeated administrations. More specific doses obviously vary depending on the administrating methods, the conditions of patients or subject animals such as age, body weight, sex, sensitivity, food (feeding), dosage intervals, medicines administered in combination, the seriousness or degrees of a disease or a patient. The optimal dose and the administration frequency under a certain condition must be determined by the appropriate dosage test of a medical specialist based on the aforementioned guide. More specifically, the dose of the compound is 0.01 mg to about 400 mg, preferably 0.1 mg to about 100 mg.

EXPERIMENTAL EXAMPLES

The present invention is described below with reference to the examples but is not limited thereby.

Percentage means the percentage by weight/volume.

Experimental Example 1-a

Preparation of spicamycin (1) Preparation of the seed culture

The culture medium used is the one in which the following components are dissolved in 1 liter of water and adjusted to a pH of 7.0:

| | |
|---|---|
| glucose | 0.4% |
| malt extract | 1.0% |
| yeast extract | 0.4% |

A 15 ml portion of the aforementioned culture medium was transferred into a 50 ml large test tube and sterilized, and *Streptomyces alanosinicus* 879-MT$_3$ (FERM BP-449) from one loopful of the slant was inoculated in the culture medium and cultured with shaking at 37° C. for 48 hours to give a seed culture.

(2) Culture

The culture medium used was the one in which the following components are dissolved in 1 liter of water and adjusted to a pH of 7.0:

| | |
|---|---|
| glucose | 2.5% |
| soy bean powder | 1.5% |
| dry yeast | 0.2% |
| calcium carbonate | 0.4% |

After the aforementioned culture medium was distributed into 500 ml Erlenmeyer flasks and sterilized, 2 ml of the seed culture was added to each flask, and the mixture was rotary-cultured on a rotary shaker at 37° C. After 4 days the culture was completed, and the cells separated by filtration were extracted twice with n-butanol.

The extract was concentrated to dryness, washed with acetone and water, dissolved into methanol and passed through a "Sephadex LH20" column which had been equilibrated with methanol. The active fraction thus obtained was concentrated to dryness, dissolved in methanol and purified by high performance liquid chromatography on a "Nucleosil 5C$_{18}$" column (8 mm$\phi$×250 mm) at a flow rate of 2 ml/min, in which an active peak having a retention time of 5.9 minutes and an ultraviolet absorption at 264 nm was collected and concentrated to dryness to give a white powder of spicamycin in the yield of 80 mg.

Experimental Example 1-b

Preparation of septacidin (1) Preparation of the seed culture

The culture medium used is the one in which the following components are dissolved in 1 liter of water and adjusted to a pH of 7.0:

| | |
|---|---|
| glucose | 0.4% |
| malt extract | 1.0% |
| yeast extract | 0.4% |

A 15 ml portion of the aforementioned culture medium was transferred into a 50 ml large test tube and sterilized, and *Streptomyces fimbriatus* ATCC 15051 from one loopful of the slant was inoculated into the culture medium and cultured with shaking at 37° C. for 48 hours to give a seed culture.

(2) Culture

The culture medium used was the one in which the following components are dissolved in 1 liter of water and adjusted to a pH of 7.0:

| | |
|---|---|
| glucose | 2.5% |
| soy bean powder | 1.5% |
| dry yeast | 0.2% |
| calcium carbonate | 0.4% |

After the aforementioned culture medium was distributed into 500 ml Erlenmeyer flasks and sterilized, 2 ml of the seed culture was added to each flask, and the mixture was rotary-cultured on a rotary shaker at 37° C. After 4 days the culture was completed, and the cells separated by filtration were extracted twice with n-butanol.

The extract was concentrated to dryness, washed with acetone and water, dissolved into methanol and passed through a "Sephadex LH20" column which had been equilibrated with methanol. The active fraction thus obtained was concentrated to dryness, dissolved in methanol and purified by high performance liquid chromatography on a "Nucleosil 5C$_{18}$" column (8 mm$\phi$×250 mm) at a flow rate of 2 ml/min, in which an active peak having a retention time of 5.6 minutes and an ultraviolet absorption at 264 nm was collected and concentrated to dryness to give a white powder of septacidin in the yield of 100 mg.

Experimental Example 2-a

Preparation of 6-(spicaminyl-amino)purine (IIa)

The spicamycin mixture (1.0 g) was dissolved in 100 ml of 10% hydrochloric acid-methanol and stirred at 30° C. for 100 hours. After the solution obtained was centrifuged, 400 ml of diethyl ether was added to the supernatant and the resulting precipitate was separated by centrifugation. The precipitate was further concentrated to dryness to give 702 mg of the crude product of 6-(spicaminyl-amino)purine (IIa), which was next dissolved in water, distributed between butanol-water (1:1). The aqueous layer was neutralized with silver carbonate, concentrated to dryness after the precipitates thus produced had been removed and purified by silica gel chromatography with an eluent of chloroform-methanol (2:1) to give 6-(spicaminyl-amino)purine (IIa) in the yield of 403 mg. 6-(spicaminyl-amino)purine thus obtained had the physicochemical properties as described above.

Experimental Example 2-b

Preparation of 6-(septaminyl-amino)purine (IIb)

The septacidin mixture (1.0 g) was dissolved in 100 ml of 10% hydrochloric acid-methanol and stirred at 30° C. for 100 hours. After the solution obtained was centrifuged, 400 ml of diethyl ether was added to the supernatant and the resulting precipitate was separated by centrifugation. The precipitate was further concentrated to dryness to give 683 mg of the crude product of 6-(septaminyl-amino)purine (IIb), which was next dissolved in water, distributed between butanol-water (1:1). The aqueous layer was neutralized with silver carbonate, concentrated to dryness after the precipitates thus produced had been removed and purified by silica gel chromatography with an eluent of chloroform-methanol (2:1) to give 6-(septaminyl-amino)purine (IIb) in the yield of 351 mg. 6-(septaminyl-amino)purine thus obtained had the physicochemical properties as described above.

Experimental Example 3-a

Preparation of 6-(4'-N-qlycyl-spicaminyl-amino)purine (IIIa)

t-Butoxycarbonyl glycine (8.0 g) and para-nitrophenol (6.3 g) were dissolved in N,N-dimethylformamide (100 cc). Further, N,N'-dicyclohexylcarbodiimide (9.4 g) was added to the solution, and the mixture was stirred for 12 hours. Precipitates produced by the reaction were removed by filtration, and N,N-dimethylformamide was removed by distillation. The residue was purified by silica gel column chromatography with n-hexane-ethyl acetate (20:1) as an eluent to give an active ester of t-butoxycarbonyl glycine in the yield of 12.5 g.

The active ester (8.0 g) was dissolved in N,N-dimethylformamide (100 ml). 6-(Spicamynyl-amino)purine (IIa, 8.1 g) and triethylamine (20 ml) were added to the solution, and the mixture was stirred for 12 hours. N,N-Dimethylformamide was removed by distillation from the reaction mixture, and the residue was purified by silica gel column chromatography. Elution with chloroform-methanol (from 7:1 to 5:1) gave 6-[4'-N-(N'-t-butyloxycarbonylglycyl)-spicaminyl-amino]purine in the yield of 9.3 g. 10% Hydrochloric acid-methanol (100 ml) was added to the product. After the mixture was stirred at room temperature for 30 minutes, the solvent was distilled under reduced pressure. Methanol (50 ml) was added to the residue, and only the methanol-insoluble fraction was separated by filtration. Repetition of the operation finally afforded 6-(4'-N-glycyl-spicaminyl-amino)purine (IIIa) hydrochloride in the yield of 7.26 g.

The hydrochloride (500 mg) was dissolved in water and passed through an Amberlite IRA410, an anion exchange resin of the OH type, and an unadsorbed fraction was concentrated to give 6-(4'-N-glycyl-spicaminyl-amino)purine (IIIa) in the yield of 230 mg.

Experimental Example 3-b

Preparation of 6-(4'-N-qlycyl-septaminyl-amino)purine (IIIb)

t-Butoxycarbonyl glycine (8.0 g) and para-nitrophenol (6.3 g) were dissolved in N,N-dimethylformamide (100 cc). Further, N,N'-dicyclohexylcarbodiimide (9.4 g) was added to the solution, and the mixture was stirred for 12 hours. Precipitates produced by the reaction were removed by filtration, and N,N-dimethylformamide was removed by distillation. The residue was purified by silica gel column chromatography with n-hexane-ethyl acetate (20:1) as an eluent to give an active ester of t-butoxycarbonyl glycine in the yield of 12.5 g.

The active ester (8.0 g) was dissolved in N,N-dimethylformamide (100 ml). 6-(septaminyl-amino)purine (IIb, 8.1 g) and triethylamine (20 ml) were added to the solution, and the mixture was stirred for 12 hours. N,N-Dimethylformamide was removed by distillation from the reaction mixture, and the residue was purified by silica gel column chromatography. Elution with chloroform-methanol (from 7:1 to 5:1) gave 6-[4'-N-(N'-t-butyloxycarbonylglycyl)-septaminyl-amino]purine in the yield of 8.8 g. 10% Hydrochloric acid-methanol (100 ml) was added to the product. After the mixture was stirred at room temperature for 30 minutes, the solvent was distilled under reduced pressure. Methanol (50 ml) was added to the residue, and only the methanol-insoluble fraction was separated by filtration. Repetition of the operation finally afforded 6-(4'-N-glycyl-septaminyl-amino)purine (IIIb) hydrochloride in the yield of 7.26 g.

The hydrochloride (500 mg) was dissolved in water and passed through an Amberlite IRA410, an anion exchange resin of the OH type, and an unadsorbed fraction was concentrated to give 6-(4'-N-glycyl-septaminyl-amino)purine (IIIb) in the yield of 219 mg.

EXAMPLE 1

Preparation of SPM6

To N,N-dimethylformamide (DMF, 30 ml) were dissolved decanoic acid (1 g) and para-nitrophenol (0.81 g). N,N-Dicyclohexylcarbodiimide (1.20 g) was added to the solution, and the mixture was stirred for 12 hours. The reaction mixture was filtered and concentrated to give an active ester of decanoic acid. To the active ester (500 mg) dissolved in DMF were added 6-(4'-N-glycyl-spicaminyl-amino)purine hydrochloride (653 mg) and triethylamine (2.0 ml), and the mixture was stirred for 12 hours. The solvent was removed by distillation, and the residue was purified by chromatography on a silica gel column with eluent systems of chloroform-methanol (from 7:1 to 5:1) to give SPM6 in the yield of 380 mg.

Physicochemical properties of SPM6

(1) Melting point: 217°–219° C., (2) Specific rotation $[\alpha]_D^{25}=+0°$ (c=0.1, in methanol), (3) Elementary analysis:

|  | C | H | O | N |
| --- | --- | --- | --- | --- |
| Calculated (%) | 53.62, | 7.31, | 20.83, | 18.24, |
| Found (%) | 53.79, | 7.10, | 21.10, | 18.01, |

(4) FD mass spectrum (m/z): 538 $(M+H)^+$, $C_{24}H_{39}O_7N_7$ (5) Infrared spectrum (KBr disc): 3400 $cm^{-1}$, 1630 $cm^{-1}$, (6) Proton nuclear magnetic resonance spectrum (500 MHz, in $CD_3OD$) $\delta_H$: 0.89 (3H, t, J=7.0 Hz), 1.20–1.40 (12H, m), 1.60–1.70 (2H, m), 2.28 (2H, t, J=7.0 Hz), 3.60–3.80 (5H, m), 3.87 (1H, d, J=16.4 Hz), 3.89 (1H, d, J=16.4 Hz), 4.06 (1H, dd, J=<1, 2.1 Hz), 4.14 (1H, dd, J=10.1, 10.1 Hz), 5.58 (1H, brs), 8.01 (1H, brs), 8.31 (1H, s).

EXAMPLE 2

Preparation of SPM9

To N,N-dimethylformamide (DMF, 30 ml) were dissolved tridecanoic acid (400 mg) and para-nitrophenol (359 mg). N,N-Dicyclohexylcarbodiimide (533 mg) was added to the solution, and the mixture was stirred for 12 hours. The reaction mixture was filtered and concentrated to give an active ester of tridecanoic acid. To the active ester (290 mg) dissolved in DMF were added 6-(4'-N-glycyl-spicaminyl-amino)purine hydrochloride (300 mg) and triethylamine (2.0 ml), and the mixture was stirred for 12 hours. The solvent was removed by distillation, and the residue was purified by silica gel column chromatography with eluent systems of chloroform-methanol (from 7:1 to 5:1) to give SPM9 in the yield of 114 mg.

Physicochemical properties of SPM9
(1) Melting point: 168°–169° C.,
(2) Specific rotation $[\alpha]_D^{25}$=+3.7° (c=0.1, in methanol),
(3) Elementary analysis:

|  | C | H | O | N |
|---|---|---|---|---|
| Calculated (%) | 55.94, | 7.82, | 19.32, | 16.91, |
| Found (%) | 55.67, | 8.01, | 19.44, | 16.88, |

(4) FD mass spectrum (m/z): 580 (M+H)$^+$, $C_{27}H_{45}O_7N_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.90 (3H, t, J=7.0 Hz), 1.30–1.70 (20H, m), 2.30 (2H, t, J=7.0 Hz), 3.60–3.80 (5H, m), 3.89 (1H, d, J=16.5 Hz), 3.92 (1H, d, J=16.5 Hz), 4.03 (1H, dd, J=2.5 Hz, <1 Hz), 4.18 (1H, dd, J=10.3, 10.3 Hz), 5.69 (1H, brs), 8.16 (1H, brs), 8.31 (1H, s).

EXAMPLE 3

Preparation of SPM12

To N,N-dimethylformamide (DMF, 30 ml) were dissolved palmitic acid (1 g) and para-nitrophenol (0.54 g). N,N-Dicyclohexylcarbodiimide (0.81 g) was added to the solution, and the mixture was stirred for 12 hours. The reaction mixture was filtered and concentrated to give an active ester of palmitic acid. To the active ester (492 mg) dissolved in DMF were added 6-(4'-N-glycyl-spicaminyl-amino)purine hydrochloride (500 mg) and triethylamine (2.0 ml), and the mixture was stirred for 12 hours. The solvent was removed by distillation, and the residue was purified by chromatography on a silica gel column with eluent systems of chloroform-methanol (from 7:1 to 5:1) to give SPM12 in the yield of 220 mg. Physicochemical properties of SPM12
(1) Melting point: 238°–240° C.,
(2) Specific rotation $[\alpha]_D^{25}$=+6.8° (c=0.1, in methanol),
(3) Elementary analysis:

|  | C | H | O | N |
|---|---|---|---|---|
| Calculated (%) | 57.95, | 8.27, | 18.01, | 15.77, |
| Found (%) | 58.12, | 8.00, | 17.93, | 15.95, |

(4) FD mass spectrum (m/z): 622 (M+H)$^+$, $C_{30}H_{51}O_7N_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.90 (3H, t, J=7.0 Hz), 1.20–1.40 (24H, m), 1.60–1.70 (2H, m), 2.28 (2H, t, J=7.0 Hz), 3.60–3.80 (5H, m), 3.87 (1H, d, J=16.4 Hz), 3.89 (1H, d, J=16.4 Hz), 4.05 (1H, dd, J=<1, 2.1 Hz), 4.14 (1H, dd, J=10.1, 10.1 Hz), 5.58 (1H, brs), 8.10 (1H, brs), 8.31 (1H, s).

EXAMPLE 4

Preparation of SPK86

To N,N-dimethylformamide (DMF, 30 ml) was dissolved trans-2-dodecenoic acid (1.5 g). Para-nitrophenol (1.0 g) and N,N-dicyclohexylcarbodiimide (1.5 g) were added to the solution, and the mixture was stirred for 12 hours. The reaction mixture was filtered and concentrated to give an active ester of trans-2-dodecenoic acid. To the active ester (250 mg) dissolved in DMF were added 6-(4'-N-glycyl-spicaminyl-amino)purine hydrochloride (300 mg) and triethylamine (1.1 ml), and the mixture was stirred for 12 hours. The solvent was removed by distillation, and the residue was purified by chromatography on a silica gel column with eluent systems of chloroform-methanol (from 7:1 to 5:1) to give SPK86 in the yield of 158 mg.
Physicochemical properties of SPK86
(1) Melting point: 180°–182° C.,
(2) Specific rotation $[\alpha]_D^{26}$=+14.4° (c=0.2, in methanol),
(3) Elementary analysis:

|  | C | H | O | N |
|---|---|---|---|---|
| Calculated (%) | 54.63, | 7.15, | 20.38, | 17.84, |
| Found (%) | 54.78, | 7.08, | 20.34, | 17.80, |

(4) FD mass spectrum (m/z): 563 (M+Na+H)$^+$, $C_{25}H_{39}O_7N_7$
(5) Infrared spectrum (KBr disc): 3400 cm$^{-1}$, 1620 cm$^{-1}$,
(6) Proton nuclear magnetic resonance spectrum (500 MHz, in CD$_3$OD) $\delta_H$: 0.90 (3H, t, J=7.1 Hz), 1.20–1.50 (12H, m), 2.22 (2H, m), 3.6–3.8 (5H, m), 3.95 (1H, d, J=16.0 Hz), 3.98 (1H, d, J=16.0 Hz), 4.02 (1H, dd, J=2.1, <1 Hz), 4.17 (1H, dd, J=10.5, 10.5 Hz), 5.68 (1H, brs), 6.00 (1H, d, J=15.2 Hz), 6.85 (1H, dt, J=6.8, 15.2 Hz), 8.12 (1H, brs), 8.32 (1H, s).

EXAMPLE 5

Preparation of SPK156

To N,N-dimethylformamide (DMF, 30 ml) were dissolved trans-2-tetradecenoic acid (1.0 g) and para-nitrophenol (0.62 g). N,N-Dicyclohexylcarbodiimide (0.91 g) were added to the solution, and the mixture was stirred for 12 hours. The reaction mixture was filtered and concentrated to give an active ester of trans-2-tetradecenoic acid. To the active ester (500 mg) dissolved in DMF were added 6-(4'-N-glycyl-spicaminyl-amino)purine hydrochloride (552 mg) and triethylamine (2.0 ml), and the mixture was stirred for 12 hours. The solvent was removed by distillation, and the residue was purified by chromatography on a silica gel column with eluent systems of chloroform-methanol (from 7:1 to 5:1) to give SPK156 in the yield of 180 mg.
Physicochemical properties of SPK156
(1) Melting point: 171°–172° C.,
(2) Specific rotation $[\alpha]_D^{25}$=+5.6° (c=0.1, in methanol),
(3) Elementary analysis:

|  | C | H | O | N |
|---|---|---|---|---|
| Calculated (%) | 56.84, | 7.67, | 18.93, | 16.57, |
| Found (%) | 57.10, | 7.38, | 19.17, | 16.35, |

(4) FD mass spectrum (m/z): 592 (M+H)$^+$, $C_{28}H_{45}O_7N_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.90 (3H, t, J=7.0 Hz), 1.20–1.60 (18H, m), 2.26 (2H, t, J=7.1 Hz), 3.30–3.80 (5H, m), 3.94 (1H, d, J=16.4 Hz), 3.98 (1H, d, J=16.4 Hz), 4.00 (1H, dd, J=2.1, <1 Hz), 4.16 (1H, dd, J=10.1, 10.1 Hz), 5.65 (1H, brs), 6.00 (1H, d, J=15.0 Hz), 6.83 (1H, dt, J=6.4, 15.0 Hz), 8.18 (1H, s), 8.32 (1H, s).

EXAMPLE 6

Preparation of SPK188 and 189

To a solution of 3-hydroxyhexadecanoic acid (2 g) in pyridine was added acetic anhydride at 0° C., and the mixture was stirred for 4 hours. The reaction mixture was distributed into chloroform-water, and the chloroform layer was concentrated. The residue obtained was dissolved in N,N-dimethylformamide (DMF). Para-nitrophenol (1.02 g) and N,N'-dicyclohexylcarbodiimide (1.51 g) were added to the solution, and the mixture was stirred for 12 hours. The reaction mixture was filtered and concentrated, and the residue was subjected to chromatography on a silica gel column with eluent systems of n-hexane-ethyl acetate (from 100:1 to 50:1) to give an active ester of 2-hexadecenoic acid (0.92 g) and an active ester of 3-acetoxyhexadecanoic acid (1.01 g).

To the active ester of 2-hexadecenoic acid (500 mg) dissolved in DMF were added 6-(4'-N-glycyl-spicaminyl-amino)purine hydrochloride (589 mg) and triethylamine (2.0 ml), and the mixture was stirred for 12 hours. The solvent was removed by distillation and the residue was subjected to chromatography on a silica gel column with eluent systems of chloroform-methanol (from 7:1 to 5:1) to give SPK188 in the yield of 149 mg.

Also, to the active ester of 3-acetoxyhexadecanoic acid (500 mg) dissolved in DMF were added 6-(4'-N-glycyl-spicaminyl-amino)purine hydrochloride (440 mg) and triethylamine (2.0 ml), and the mixture was stirred for 12 hours. The solvent was removed by distillation and the residue was subjected to chromatography on a silica gel column with eluent systems of chloroform-methanol (from 7:1 to 5:1) to give SPK189 in the yield of 126 mg.

Physicochemical properties of SPK188

(1) Melting point: 178°–179° C.,
(2) Specific rotation $[\alpha]_D^{25}$=+1.2° (c=0.1, in methanol),
(3) Elementary analysis:

|  | C | H | O | N |
|---|---|---|---|---|
| Calculated (%) | 58.14, | 7.97, | 18.07, | 15.82, |
| Found (%) | 58.36, | 7.72, | 17.91, | 16.01, |

(4) FD mass spectrum (m/z): 620 (M+H)$^+$, $C_{30}H_{49}O_7N_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.89 (3H, t, J=7.1 Hz), 1.20–1.60 (22H, m), 2.20 (2H, t, J=7.1, 7.1 Hz), 3.60–3.80 (5H, m), 3.90 (1H, d, J=16.4 Hz), 3.97 (1H, d, J=16.4 Hz), 4.00 (1H, dd, J=2.1, <1 Hz), 4.15 (1H, dd, J=10.4, 10.4 Hz), 5.68 (1H, brs), 6.00 (1H, d, J=15.7 Hz), 6.82 (1H, dt, J=15.7, 7.1 Hz), 8.15 (1H, s), 8.28 (1H, s).

Physicochemical properties of SPK189

(1) Melting point: 182°–183° C.,
(2) Elementary analysis:

|  | C | H | O | N |
|---|---|---|---|---|
| Calculated (%) | 56.54, | 7.86, | 21.18, | 14.42, |
| Found (%) | 56.71, | 7.73, | 20.95, | 14.61, |

(3) FD mass spectrum (m/z): 680 (M+H)$^+$, $C_{32}H_{53}O_7N_9$
(4) Infrared spectrum (KBr disc): 3400 cm$^{-1}$, 1720 cm$^{-1}$, 1630 cm$^{-1}$,
(5) Proton nuclear magnetic resonance spectrum (500 MHz, in CD$_3$OD) $\delta_H$: 0.90 (3H, t, J=7.1 Hz), 1.20–1.70 (24H, m), 2.05 (3H, s), 2.52 (2H, d, J=5.7 Hz), 3.6–3.9 (7H, m), 4.01 (1H, dd, J=2.1, <1 Hz), 4.14 (1H, dd, J=10.4, 10.4 Hz), 5.21 (1H, m), 5.62 (1H, brs), 8.15 (1H, brs), 8.30 (1H, s).

EXAMPLE 7

Preparation of SPK44

To N,N-dimethylformamide (DMF, 30 ml) was dissolved 11-dodecenoic acid (500 mg) and para-nitrophenol (351 mg). N,N'-Dicyclohexylcarbodiimide (520 mg) were added to the solution, and the mixture was stirred for 12 hours. The reaction mixture was filtered and concentrated to give an active ester of 11-dodecenoic acid. To the active ester (500 mg) dissolved in DMF were added 6-(4'-N-glycyl-spicaminyl-amino)purine hydrochloride (443 mg) and triethylamine (1.6 ml), and the mixture was stirred for 12 hours. The solvent was removed by distillation, and the residue was subjected to chromatography on a silica gel column with eluent systems of chloroform-methanol (from 7:1 to 5:1) to give SPK44 in the yield of 196 mg.

Physicochemical properties of SPK44

(1) Melting point: 222°–224° C.,
(2) Specific rotation $[\alpha]_D^{24}$=+21.5° (c=0.1, in methanol),
(3) Elementary analysis:

|  | C | H | O | N |
|---|---|---|---|---|
| Calculated (%) | 55.40, | 7.33, | 19.87, | 17.39, |
| Found (%) | 55.70, | 7.26, | 19.94, | 17.10, |

(4) FD mass spectrum (m/z): 564 (M+H)$^+$, $C_{26}H_{41}N_7O_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.2–1.7 (14H, m), 2.03 (2H, m), 2.28 (2H, t, J=7.6 Hz), 3.65–3.85 (5H, m), 3.88 (1H, d, J=16.0 Hz), 3.91 (1H, d, J=16.0 Hz), 4.02 (1H, dd, J=2.1, <1 Hz), 4.17 (1H, dd, J=10.3, 10.3 Hz), 4.92 (1H, d, J=10.9 Hz), 4.98 (1H, d, J=17.0 Hz), 5.67 (1H, brs), 5.79 (1H, m), 8.12 (1H, s), 8.26 (1H, s).

EXAMPLE 8

Preparation of SPK142

To a solution of 12-tridecenoic acid (370 mg) in N,N-dimethylformamide (DMF) were dissolved para-nitrophenol (243 mg) and N,N'-dicyclohexylcarbodiimide (360 mg), and the mixture was stirred for 12 hours. The reaction mixture was filtered and concentrated to give an active ester of 12-tridecenoic acid. To the active ester (580 mg) were added 6-(4'-N-glycyl-spicaminylamino)purine hydrochloride (350 mg) and triethylamine (1.3 ml), and the mixture was stirred for 12 hours. The solvent was removed by distillation, and the residue was subjected to chromatography on a silica gel column with eluent systems of chloroform-methanol (from 7:1 to 5:1) to give SPK142 in the yield of 80 mg.

Physicochemical properties of SPK142

(1) Melting point: 182°–184° C.,
(2) Specific rotation $[\alpha]_D^{25}$+13.3° (c=0.1, in methanol),
(3) Elementary analysis:

|  | C | H | O | N |
|---|---|---|---|---|
| Calculated (%) | 56.24, | 7.34, | 19.42, | 17.00, |
| Found (%) | 56.40, | 7.42, | 19.45, | 16.73, |

(4) FD mass spectrum (m/z): 577 (M+H)$^+$, $C_{27}H_{42}N_7O_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.70 (16H, m), 2.03 (2H, m), 2.28 (2H, t, J=7.2 Hz), 3.60–3.80 (5H, m), 3.86 (1H, d, J=15.0 Hz), 3.89 (1H, d, J=15.0 Hz), 4.00 (1H, d, J=2.0 Hz), 4.14 (1H, dd, J=10.0, 10.0 Hz), 4.92 (1H, d, J=10.9 Hz), 4.98 (1H, d, J=17.0 Hz), 5.67 (1H, brs), 5.81 (1H, m), 8.15 (1H, s), 8.32 (1H, s).

EXAMPLE 9

Preparation of SPK106

To oleic acid (1 g) and para-nitrophenol (492 mg) dissolved in N,N-dimethylformamide (DMF, 30 ml) was added N,N'-dicyclohexylcarbodiimide (730 mg), and the mixture was stirred for 12 hours. The reaction mixture was filtered and concentrated to give an active ester of oleic acid. To the active ester (745 mg) dissolved in DMF were added 6-(4'-N-glycyl-spicaminyl-amino)purine hydrochloride (400 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK106 in the yield of 150 mg.

Physicochemical properties of SPK106

(1) Melting point: 224°–225° C.,
(2) Specific rotation $[\alpha]_D^{25}=+20°$ (c=0.1, in methanol),
(3) Elementary analysis:

|  | C | H | O | N |
|---|---|---|---|---|
| Calculated (%) | 59.33, | 8.25, | 17.29, | 15.13, |
| Found (%) | 59.12, | 8.43, | 17.37, | 15.08, |

(4) FD mass spectrum (m/z): 648 (M+H)$^+$, $C_{32}H_{53}N_7O_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.89 (3H, t, J=7.1 Hz), 1.2–1.7 (24H, m), 2.02 (4H, m), 2.28 (2H, t, J=7.0 Hz), 3.7–3.9 (5H, m), 3.85 (1H, d, J=16.0 Hz), 3.88 (1H, d, J=16.0 Hz), 3.98 (1H, dd, J=3.0 Hz, <1 Hz), 4.12 (1H, dd, J=10.8, 10.8 Hz), 5.35 (2H, m), 5.66 (1H, brs), 8.15 (1H, s), 8.32 (1H, s).

EXAMPLE 10

Preparation of SPK120

To linoleic acid (1 g) and para-nitrophenol (496 mg) dissolved in N,N-dimethylformamide (DMF, 30 ml) was added N,N'-dicyclohexylcarbodiimide (736 mg), and the mixture was stirred for 12 hours. The reaction mixture was filtered and concentrated to give an active ester of linoleic acid. To the active ester (500 mg) dissolved in DMF were added 6-(4'-N-glycyl-spicaminyl-amino)purine hydrochloride (478 mg) and triethylamine (1.7 ml), and the mixture was stirred for 12 hours. The solvent was removed by distillation, and the residue was subjected to chromatography on a silica gel column with eluent systems of chloroform-methanol (from 7:1 to 5:1) to give SPK120 in the yield of 154 mg.

Physicochemical properties of SPK120

(1) Melting point: 228°–229° C.,
(2) Specific rotation $[\alpha]_D^{25}=+5°$ (c=0 1, in methanol),
(3) Elementary analysis:

|  | C | H | O | N |
|---|---|---|---|---|
| Calculated (%) | 59.52, | 7.96, | 17.34, | 15.18, |
| Found (%) | 59.41, | 8.07, | 17.46, | 15.06, |

(4) FD mass spectrum (m/z): 646 (M+H)$^+$, $C_{32}H_{51}N_7O_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 0.91 (3H, t, J=7.1 Hz), 1.25–1.7 (16H, m), 2.08 (4H, m), 2.28 (2H, t, J=7.0 Hz), 2.87 (2H, t, J=7.0 Hz), 3.60–3.80 (5H, m), 3.86 (1H, d, J=15.0 Hz), 3.89 (1H, d, J=15.0 Hz), 4.00 (1H, dd, J=2.8 Hz, H-2'), 4.14 (1H, dd, J=10.0, 10.0 Hz, H-4'), 5.30–5.40 (4H, m), 5.68 (1H, brs, H-1'), 8.15 (1H, s, H-8), 8.30 (1H, s, H-2).

EXAMPLE 11

Preparation of SPK231

To cis-9-tetradecenoic acid (197 mg) and N-hydroxysuccinimide (101 mg) dissolved in N,N-dimethylformamide (DMF, 30 ml) was added N,N'-dicyclohexylcarbodiimide (198 mg), and the mixture was stirred for 12 hours. The reaction mixture was filtered and concentrated to give an active ester of cis-9-tetradecenoic acid. To the active ester (280 mg) dissolved in DMF were added 6-(4'-N-glycyl-spicaminyl-amino)purine hydrochloride (334 mg) and triethylamine (0.97 ml), and the mixture was stirred for 12 hours. The solvent was removed by distillation, and the residue was subjected to chromatography on a silica gel column with eluent systems of chloroform-methanol (from 7:1 to 5:1) to give SPK231 in the yield of 520 mg.

Physicochemical properties of SPK231

(1) Melting point: 163°–164° C.,
(2) Specific rotation $[\alpha]_D^{25}=+9.2°$ (c=0.1, in methanol),
(3) Elementary analysis:

|  | C | H | O | N |
|---|---|---|---|---|
| Calculated (%) | 56.84, | 7.67, | 18.93, | 16.57, |
| Found (%) | 56.51, | 7.82, | 19.12, | 16.55, |

(4) FD mass spectrum (m/z): 592 (M+H)$^+$, $C_{28}H_{45}N_7O_7$
(5) Infrared spectrum (KBr disc): 3400 cm$^{-1}$, 1630 cm$^{-1}$,
(6) Proton nuclear magnetic resonance spectrum (500 MHz, in CDCl$_3$—CD$_3$OD) $\delta_H$: 0.91 (3H, t, J=7.0 Hz), 1.27–1.40 (14H, m), 1.65 (2H, m), 2.02 (4H, m), 2.28 (2H, t, J=7.0 Hz), 3.65–3.80 (5H, m), 3.87 (1H, d, J=15.0 Hz), 3.89 (1H, d, J=15.0 Hz), 4.06 (1H, d, J=2.1 Hz, H-2'), 4.17 (1H, dd, J=10.3, 10.3 Hz), 5.34 (2H, m), 5.62 (1H, brs), 8.08 (1H, s), 8.30 (1H, s).

EXAMPLE 12

Preparation of SPK9

To 10-methylundecanoic acid (240 mg) and para-nitrophenol (167 mg) dissolved in N,N-dimethylformamide (DMF, 30 ml) was added N,N'-dicyclohexylcarbodiimide (247 mg), and the mixture was stirred for 12 hours. The reaction mixture was filtered and concentrated to give an active ester of 10-methylundecanoic acid. To the active ester (380 mg) dissolved in DMF were added 6-(4'-N-glycyl-spicaminyl-amino)purine hydrochloride (460 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK9 in the yield of 121 mg.

Physicochemical properties of SPK9
(1) Melting point: 192°–195° C.,
(2) Specific rotation $[\alpha]_D^{25}$=+6.2° (c=0.1, in methanol),
(3) Elementary analysis:

|  | C | H | O | N |
|---|---|---|---|---|
| Calculated (%) | 55.21, | 7.66, | 19.80, | 17.33, |
| Found (%) | 55.50, | 7.39, | 19.72, | 17.39, |

(4) FD mass spectrum (m/z): 589 (M+Na+H)$^+$, $C_{26}H_{43}N_7O_7$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.87 (6H, d, J=6.4 Hz), 1.1–1.7 (15H, m), 2.28 (2H, t, J=7.0 Hz), 3.6–3.9 (5H, m), 3.85 (1H, d, J=15.6 Hz), 3.89 (1H, d, J=15.6 Hz), 4.02 (1H, dd, J=2.1, <1 Hz), 4.15 (1H, dd, J=10.3, 10.3 Hz), 5.68 (1H, brs), 8.12 (1H, brs), 8.27 (1H, s).

EXAMPLE 13

Preparation of SPK136

To 12-methyltridecanoic acid (200 mg) and para-nitrophenol (122 mg) dissolved in N,N-dimethylformamide (DMF, 30 ml) was added N,N'-dicyclohexylcarbodiimide (183 mg), and the mixture was stirred for 12 hours. The reaction mixture was filtered and concentrated to give an active ester of 12-methyltridecanoic acid. To the active ester (303 mg) dissolved in DMF were added 6-(4'-N-glycyl-spicaminyl-amino)purine hydrochloride (336 mg) and triethylamine (1.3 ml), and the mixture was stirred for 12 hours. The solvent was removed by distillation, and the residue was subjected to chromatography on a silica gel column with eluent systems of chloroform-methanol (from 7:1 to 5:1) to give SPK136 in the yield of 136 mg.

Physicochemical properties of SPK136
(1) Melting point: 225°–226° C.,
(2) Specific rotation $[\alpha]_D^{25}$=+9.1° (c=0.1, in methanol),
(3) Elementary analysis:

|  | C | H | O | N |
|---|---|---|---|---|
| Calculated (%) | 56.64, | 7.98, | 18.86, | 16.51, |
| Found (%) | 56.43, | 8.14, | 19.15, | 16.28, |

(4) FD mass spectrum (m/z): 616 (M+Na)$^+$, $C_{28}H_{47}N_7O_7$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.87 (6H, d, J=6.6 Hz), 1.10–1.70 (19H, m), 2.29 (2H, t, J=7.0 Hz), 3.60–3.80 (5H, m), 3.85 (1H, d, J=15.0 Hz), 3.89 (1H, d, J=15.0 Hz), 4.00 (1H, d, J=2.1 Hz), 4.13 (1H, dd, J=10.3, 10.3 Hz), 5.65 (1H, brs), 8.15 (1H, brs), 8.30 (1H, s).

EXAMPLE 14

Preparation of SPK64

To 11-bromoundecanoic acid (1 g) and para-nitrophenol (0.56 g) dissolved in N,N-dimethylformamide (DMF, 30 ml) was added N,N'-dicyclohexylcarbodiimide (0.83 g), and the mixture was stirred for 12 hours. The reaction mixture was filtered and concentrated to give an active ester of 11-bromoundecanoic acid. To the active ester (500 mg) dissolved in DMF were added 6-(4'-N-glycyl-spicaminyl-amino)purine hydrobromide (496 mg) and triethylamine (2.5 ml), and the mixture was stirred for 12 hours. The solvent was removed by distillation, and the residue was subjected to chromatography on a silica gel column with eluent systems of chloroform-methanol (from 7:1 to 5:1) to give SPK64 in the yield of 210 mg.

Physicochemical properties of SPK64
(1) Melting point: 175°–178° C.,
(2) Specific rotation $[\alpha]_D^{24}$=+17.3° (c=0 1, in methanol),
(3) Elementary analysis:

|  | C | H | O | N |
|---|---|---|---|---|
| Calculated (%) | 47.62, | 6.39, | 17.76, | 15.55, |
| Found (%) | 47.90, | 6.10, | 17.52, | 15.68, |

(4) FD mass spectrum (m/z): 630, 632 (M+H)$^+$, $C_{25}H_{40}N_7O_7Br$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 1.30–1.90 (16H, m), 2.29 (2H, t, J=7.0 Hz), 3.44 (2H, t, J=7.2 Hz), 3.60–3.80 (5H, m), 3.86 (1H, d, J=17.0 Hz), 3.90 (1H, d, J=17.0 Hz), 4.01 (1H, dd, J=2.1, <1 Hz), 4.15 (1H, dd, J=10.9, 10.9 Hz), 5.67 (1H, brs), 8.15 (1H, s), 8.30 (1H, s).

EXAMPLE 15

Preparation of SPK152

To 12-bromododecanoic acid (1 g) and para-nitrophenol (490 mg) dissolved in N,N-dimethylformamide (DMF, 30 ml) was added N,N'-dicyclohexylcarbodiimide (740 mg), and the mixture was stirred for 12 hours. The reaction mixture was filtered and concentrated to give an active ester of 12-bromododecanoic acid. To the active ester (560 mg) dissolved in DMF were added 6-(4'-N-glycyl-spicaminyl-amino)purine hydrobromide (530 mg) and triethylamine (1.4 ml), and the mixture was stirred for 12 hours. The solvent was removed by distillation, and the residue was subjected to chromatography on a silica gel column with eluent systems of chloroform-methanol (from 7:1 to 5:1) to give SPK152 in the yield of 177 mg.

Physicochemical properties of SPK152
(1) Melting point: 164°–165° C.,
(2) Specific rotation $[\alpha]_D^{25}$=0° (c=0.1, in methanol),
(3) Elementary analysis:

|  | C | H | O | N |
|---|---|---|---|---|
| Calculated (%) | 52.04, | 7.05, | 18.66, | 16.34, |
| Found (%) | 52.32, | 7.24, | 18.52, | 16.01, |

(4) FD mass spectrum (m/z): 644, 646 (M+H)$^+$, $C_{26}H_{42}N_7O_7Br$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 1.20–1.70 (18H, m), 1.82 (2H, m), 2.28 (2H, t, J=7.0 Hz), 3.43 (2H, t, J=7.1 Hz), 3.60–3.80 (5H, m), 3.86 (1H, d, J=15.1 Hz), 3.89 (1H, d, J=15.1 Hz), 4.00 (1H, dd, J=2.1, <1 Hz), 4.14 (1H, dd, J=10.1, 10.1 Hz), 5.68 (1H, brs), 8.15 (1H, brs), 8.30 (1H, s).

EXAMPLE 16

Preparation of SPK132

To 12-bromododecanoic acid (1 g) dissolved in acetonitrile (50 ml) was added calcium chloride (2 g) and tetra-n-butylammonium chloride (1.2 g), and the mixture was heated under reflux for 4 hours. The reaction mixture was filtered, concentrated and distributed into ethyl acetate-water, and the ethyl acetate layer was dried over anhydrous sodium sulfate to give 12-chlorododecanoic acid. After a 280 mg portion of 12-chlorododecanoic acid thus obtained, para-nitrophenol (167 mg) and N,N'-dicyclohexylcarbodiimide (245 mg) in N,N-dimethylformamide (DMF) was stirred for 12 hours, precipitates were removed by filtration and DMF was removed by distillation to give an active ester. To the active ester of 12-chlorododecanoic acid dissolved in DMF were added 6- (4'-N-glycyl-spicaminyl-amino)purine hydrochloride (456 mg) and triethylamine (1.2 ml), and the mixture was stirred for 12 hours. The reaction mixture was concentrated and subjected to chromatography on a silica gel column with eluent systems of chloroform-methanol (from 7:1 to 5:1) to give SPK132 in the yield of 287 mg.

Physicochemical properties of SPK132

(1) Melting point: 216°–220° C., (2) Specific rotation $[\alpha]_D^{24}$=+34.3° (c=0.1, in methanol), (3) Elementary analysis:

|  | C | H | O | N |
|---|---|---|---|---|
| Calculated (%) | 52.04, | 7.05, | 18.66, | 16.34, |
| Found (%) | 52.00, | 7.30, | 18.79, | 16.50, |

(4) FD mass spectrum (m/z): 622, 624 $(M+Na)^+$, $C_{26}H_{42}N_7O_7Cl$ (5) Infrared spectrum (KBr disc): 3400 $cm^{-1}$, 1630 $cm^{-1}$, (6) Proton nuclear magnetic resonance spectrum (500 MHz, in $CD_3OD$) $\delta_H$: 1.20–1.80 (20H, m), 3.55 (2H, t, J=7.2 Hz), 3.60–3.80 (5H, m), 3.87 (1H, d, J=15.4 Hz), 3.91 (1H, d, J=15.4 Hz), 4.01 (1H, dd, J=2.1, <1 Hz), 4.14 (1H, dd, J=10.3, 10.3 Hz), 5.68 (1H, brs), 8.13 (1H, s), 8.28 (1H, s).

EXAMPLE 17

Preparation of SPK133

To 11-bromoundecanoic acid (1 g) dissolved in acetonitrile (50 ml) were added calcium chloride (2 g) and tetra-n-butylammonium chloride (1.2 g), and the mixture was heated under reflux for 4 hours. The reaction mixture was filtered, concentrated and then distributed into ethyl acetate-water, and the ethyl acetate layer was dried over anhydrous sodium sulfate to give 11-chloroundecanoic acid (0.85 g). After a 230 mg portion of 11-bromoundecanoic acid thus obtained, para-nitrophenol (145 mg) and N,N'-dicyclohexylcarbodiimide (215 mg) in N,N-dimethylformamide (DMF) was stirred for 12 hours, precipitates were removed by filtration and DMF was removed by distillation to give an active ester. To the active ester of 11-chloroundecanoic acid dissolved in DMF (20 ml) were added 6-(4'-N-glycyl-spicaminyl-amino)purine hydrochloride (400 mg) and triethylamine (1.2 ml), and the mixture was stirred for 12 hours. The reaction mixture was concentrated and subjected to chromatography on a silica gel column with eluent systems of chloroform-methanol (from 7:1 to 5:1) to give SPK133 in the yield of 103 mg.

Physicochemical properties of SPK133

(1) Melting point: 214°–218° C., (2) Specific rotation $[\alpha]_D^{24}$=+20° (c=0.1, in methanol), (3) Elementary analysis:

|  | C | H | O | N |
|---|---|---|---|---|
| Calculated (%) | 51.23, | 6.88, | 19.11, | 16.73, |
| Found (%) | 51.03, | 6.78, | 19.02, | 16.58, |

(4) FD mass spectrum (m/z): 586, 588 $(M+H)^+$, $C_{25}H_{40}N_7O_7Cl$ (5) Infrared spectrum (KBr disc): 3400 $cm^{-1}$, 1630 $cm^{-1}$, (6) Proton nuclear magnetic resonance spectrum (500 MHz, in $CD_3OD$) $\delta_H$: 1.30–1.80 (18H, m), 2.30 (2H, t, J=7.0 Hz), 3.54 (2H, t, J=7.2 Hz), 3.60–3.80 (5H, m), 3.88 (1H, d, J=15.0 Hz), 3.91 (1H, d, J=15.0 Hz), 4.02 (1H, dd, J=2.0, <1 Hz), 4.15 (1H, dd, J=10.3, 10.3 Hz), 5.66 (1H, brs), 8.12 (1H, brs), 8.30 (1H, s).

EXAMPLE 18

Preparation of SPK146

12-Hydroxydodecanoic acid (1 g) dissolved in 10% hydrochloric acid-methanol solution (20 ml) was stirred at room temperature for 1 hour. The reaction mixture was concentrated and distributed into chloroform-water. The chloroform layer was further washed with a 1% aqueous sodium bicarbonate solution and water, dried over anhydrous sodium sulfate and concentrated to give the methyl ester of 12-hydroxydodecanoic acid (1.03 g). To the methyl ester of 12-hydroxydodecanoic acid (1 g) dissolved in pyridine (20 ml) was added paratoluenesulfonyl chloride (0.85 g), and the mixture was stirred for 8 hours. After the pyridine was removed by distillation, the residue was distributed into chloroform-water and the chloroform layer was dried over anhydrous sodium sulfate, concentrated and then subjected to chromatography on a silica gel column with an eluent system of n-hexane-ethyl acetate (50:1) to give the methyl ester of 12-paratoluenesulfonyloxydodecanoic acid (1.21 g). After the total product was dissolved in acetonitrile (50 ml) and 5 ml of 1M solution of tetra-n-butylammonium fluoride in tetrahydrofuran was added, the mixture was stirred for 48 hours. The reaction mixture was concentrated, and the residue was subjected to chromatography on a silica gel column with an eluent system of n-hexane-ethyl acetate (100:1) to give the methyl ester of 12-fluorododecanoic acid (680 mg). The product was dissolved in a mixed solvent of ethanol-water (1:1). Potassium hydroxide (0.7 g) was added to the solution, and the mixture was stirred at 80° C. for 30 minutes. After the reaction mixture was concentrated and adjusted to a weak acidic range of pH by adding water and an excessive amount of citric acid, it was extracted with ethyl acetate. The ethyl acetate layer was dried over anhydrous sodium sulfate and concentrated to give 12-fluorododecanoic acid (610 mg).

After 12-fluorododecanoic acid thus obtained (610 mg) and para-nitrophenol (390 mg) were dissolved in N,N-dimethylformamide (DMF, 30 ml), N,N'-dicyclohexylcarbodiimide (576 mg) was added, and the mixture was stirred for 12 hours. The reaction mixture was filtered and concentrated to give the active ester of 12-fluorododecanoic acid. To the active ester (500 mg), which was dissolved in DMF, were added 6-(4'-N-glycyl-spicaminyl-amino)purine trifluoroacetate (565 mg) and triethylamine (2.0 ml), and the mixture was stirred for 12 hours. After the solvent was removed by distillation, the residue was subjected to chromatography on a silica gel column with eluent systems of chloroform-methanol (from 7:1 to 5:1) to give SPK146 in the yield of 183 mg.

Physicochemical properties of SPK146
(1) Melting point: 182°–183° C.,
(2) Specific rotation $[\alpha]_D^{25}$=0° (c=0.1, in methanol),
(3) Elementary analysis:

|  | C | H | O | N |
| --- | --- | --- | --- | --- |
| Calculated (%) | 53.50, | 7.25, | 19.19, | 16.80, |
| Found (%) | 53.82, | 7.03, | 18.95, | 17.09, |

(4) FD mass spectrum (m/z): 584 (M+H)$^+$, $C_{26}H_{42}N_7O_7F$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.80 (18H, m), 2.29 (2H', t, J=7.0 Hz), 3.60–3.90 (5H, m), 3.86 (1H, d, J=16.4 Hz), 3.90 (1H, d, J=16.4 Hz), 4.00 (1H, dd, J=2.1, <1 Hz), 4.15 (1H, dd, J=10.4, 10.4 Hz), 4.40 (2H, dt, J=6.4, 47.1 Hz), 5.69 (1H, brs), 8.16 (1H, s), 8.31 (1H, s).

EXAMPLE 19

Preparation of SPK157

16-Hydroxyhexadecanoic acid (1 g) dissolved in 10% hydrochloric acid-methanol solution (20 ml) was stirred at room temperature for 1 hour. The reaction mixture was concentrated and distributed into chloroform-water. The chloroform layer was further washed with a 1% aqueous sodium bicarbonate solution and water, dried over anhydrous sodium sulfate and concentrated to give the methyl ester of 16-hydroxyhexadecanoic acid (1.03 g). To the methyl ester of 16-hydroxyhexadecanoic acid, which was dissolved in pyridine (20 ml), was added paratoluenesulfonyl chloride (0.69 g), and the mixture was stirred for 8 hours. After the pyridine was removed by distillation, the residue was distributed into chloroform-water and the chloroform layer was dried over anhydrous sodium sulfate, concentrated and then subjected to chromatography on a silica gel column with an eluent system of n-hexane-ethyl acetate (50:1) to give the methyl ester of 16-paratoluenesulfonyloxyhexadecanoic acid (1.21 g). After the total product was dissolved in acetonitrile (30 ml) and 5 ml of 1M solution of tetra-n-butylammonium fluoride in tetrahydrofuran was added, the mixture was stirred for 48 hours. The reaction mixture was concentrated, and the residue was subjected to chromatography on a silica gel column with an eluent system of n-hexane-ethyl acetate (100:1) to give the methyl ester of 16-fluorohexadecanoic acid (0.53 g). The product was dissolved in a mixed solvent of ethanol-water (1:1). Potassium hydroxide (0.6 g) was added to the solution, and the mixture was stirred at 80° C. for 30 minutes. After the reaction mixture was concentrated and adjusted to a weak acidic range of pH by adding water and an excessive amount of citric acid, it was extracted with ethyl acetate. The ethyl acetate layer was dried over anhydrous sodium sulfate and concentrated to give 16-fluorohexadecanoic acid (440 mg).

After 16-fluorohexadecanoic acid thus obtained (438 mg) and para-nitrophenol (222 mg) were dissolved in N,N-dimethylformamide (DMF, 30 ml), N,N'-dicyclohexylcarbodiimide (330 mg) was added, and the mixture was stirred for 12 hours. The reaction mixture was filtered and concentrated to give the active ester of 16-fluorohexadecanoic acid. To the active ester, which was dissolved in DMF, were added 6-(4'-N-glycyl-spicaminyl-amino)purine trifluoroacetate (612 mg) and triethylamine (2.0 ml), and the mixture was stirred for 12 hours. After the solvent was removed by distillation, the residue was subjected to chromatography on a silica gel column with eluent systems of chloroform-methanol (from 7:1 to 5:1) to give SPK157 in the yield of 228 mg. Physicochemical properties of SPK157
(1) Melting point: 175°–176° C.,
(2) Specific rotation $[\alpha]_D^{25}$=+6.4° (c=0.1, in methanol),
(3) Elementary analysis:

|  | C | H | O | N |
| --- | --- | --- | --- | --- |
| Calculated (%) | 55.49, | 8.03, | 17.84, | 15.62, |
| Found (%) | 56.71, | 7.80, | 17.66, | 15.83, |

(4) FD mass spectrum (m/z): 628 (M+H)$^+$, $C_{29}H_{50}N_7O_7F$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.50 (26H, m), 2.28 (2H, t, J=7.1 Hz), 3.60–3.80 (5H, m), 3.85 (1H, d, J=16.4 Hz), 3.90 (1H, d, J=16.4 Hz), 4.01 (1H, dd, J=2.1, <1 Hz), 4.15 (1H, dd, J=10.4, 10.4 Hz), 4.40 (1H, dt, J=7.1, 42 Hz), 5.65 (1H, brs), 8.13 (1H, s), 8.32 (1H, s).

EXAMPLE 20

Preparation of SPK165

To 11-bromoundecanoic acid dissolved in acetonitrile (50 ml) were added sodium iodide (2 g) and tetra-n-butylammonium iodide (1 g), and the mixture was heated under reflux for 4 hours. The reaction mixture was filtered, concentrated and distributed into ethyl acetate and water, and the ethyl acetate layer was dried over anhydrous sodium sulfate and concentrated to give 11-iodoundecanoic acid (0.89 g).

To a solution of 11-iodoundecanoic acid thus obtained and para-nitrophenol (0.36 g) in N,N-dimethylformamide (DMF, 30 ml) was added N,N'-dicyclohexylcarbodiimide (0.53 g), and the mixture was stirred for 12 hours. The reaction mixture was filtered and concentrated to give the active ester of 11-iodoundecanoic acid. To the active ester (0.6 g), after having been dissolved in DMF, were added again 6-(4'-N-glycyl-spicaminyl-amino)purine hydroiodide (0.53 g) and triethylamine (2.0 ml), and the mixture was stirred for 12 hours. After the solvent was removed by distillation, the residue was subjected to chromatography on a silica gel column with eluent systems of chloroform-methanol (from 7:1 to 5:1) to give SPK165 in the yield of 0.18 g.

Physicochemical properties of SPK165
(1) Melting point: 174°–175° C.,
(2) Specific rotation $[\alpha]_D^{25}$=+11.6° (c=0.1, in methanol),
(3) Elementary analysis:

|  | C | H | O | N |
| --- | --- | --- | --- | --- |
| Calculated (%) | 44.32, | 5.95, | 16.53, | 14.47, |
| Found (%) | 44.60, | 5.72, | 16.31, | 14.69, |

(4) FD mass spectrum (m/z): 678 (M+H)$^+$, $C_{25}H_{40}N_7O_7I$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.90 (16H, m), 2.28 (2H, t, J=7.1 Hz), 3.22 (2H, t, J=7.1 Hz), 3.60–3.80 (5H, m), 3.87 (1H, d, J=16.4 Hz), 3.90 (1H, d, J=16.4 Hz), 4.01 (1H, dd, J=2.1, <1 Hz), 4.12 (1H, dd, J=10.4, 10.4 Hz), 5.64 (1H, brs), 8.15 (1H, brs), 8.31 (1H, s).

EXAMPLE 21

Preparation of SPK153

To 2-bromohexadecanoic acid (1 g) and para-nitrophenol (0.42 g) dissolved in N,N-dimethylformamide (DMF, 30 ml) was added N,N'-dicyclohexylcarbodiimide (0.62 g), and the mixture was stirred for 12 hours. The reaction mixture was filtered and concentrated to give an active ester of 2-bromohexadecanoic acid. To the active ester (0.5 g), which was dissolved in DMF, were added 6-(4'-N-glycyl-spicaminyl-amino)purine hydrobromide (0.43 g) and triethylamine (2.0 ml), and the mixture was stirred for 12 hours. The solvent was removed by distillation, and the residue was subjected to chromatography on a silica gel column with eluent systems of chloroform-methanol ( from 7:1 to 5:1) to give SPK153 in the yield of 0.15 g.

Physicochemical properties of SPK153

(1) Melting point: 167°–169° C.,
(2) Elementary analysis:

|  | C | H | O | N |
|---|---|---|---|---|
| Calculated (%) | 51.43, | 7.19, | 15.98, | 13.99, |
| Found (%) | 51.70, | 6.98, | 15.89, | 14.20, |

(3) FD mass spectrum (m/z): 700, 702 (M+H)$^+$, $C_{30}H_{50}N_7O_7Br$ (4) Infrared spectrum (KBr disc): 3400 cm$^{-1}$, 1630 cm$^{-1}$, (5) Proton nuclear magnetic resonance spectrum (500 MHz, in CD$_3$OD) $\delta_H$: 0.90 (3H, t, J=7.1 Hz), 1.20–1.60 (24H, m), 1.90–2.10 (2H, m), 3.60–3.80 (5H, m), 3.80–4.05 (3H, m), 4.15 (1H, dd, J=10.4, 10.4 Hz), 4.40 (1H, m), 5.63 (1H, brs), 8.15 (1H, brs), 8.31 (1H, s).

EXAMPLE 22

Preparation of SPK175

To 2-bromododecanoic acid (1 g), after having been dissolved in acetonitrile (50 ml), were added calcium chloride (2 g) and tetraethylammonium chloride (1 g), and the mixture was heated under reflux for 4 hours. The reaction mixture was filtered, concentrated and distributed into ethyl acetate and water, and the ethyl acetate layer was dried over anhydrous sodium sulfate and concentrated to give 2-chlorododecanoic acid.

To 2-chlorododecanoic acid (0.8 g) and para-nitrophenol (0.48 g), which were dissolved in N,N-dimethylformamide (DMF, 30 ml), was added N,N'-dicyclohexylcarbodiimide (0.71 g), and the mixture was stirred for 12 hours. The reaction mixture was filtered and concentrated to give the active ester of 2-chlorododecanoic acid. To the active ester of 2-chlorododecanoic acid dissolved in DMF were added again 6-(4'-N-glycyl-spicaminyl-amino)purine hydrochloride (0.53 g) and triethylamine (2.0 ml), and the mixture was stirred for 12 hours. The solvent was removed by distillation and the residue was subjected to chromatography on a silica gel column with eluent systems of chloroform-methanol (from 7:1 to 5:1) to give SPK175 in the yield of 0.15 g.

Physicochemical properties of SPK175

(1) Melting point: 175°–176° C.,
(2) Elementary analysis:

|  | C | H | O | N |
|---|---|---|---|---|
| Calculated (%) | 52.04, | 7.05, | 18.66, | 16.34, |
| Found (%) | 52.20, | 6.81, | 18.46, | 16.52, |

(3) FD mass spectrum (m/z): 601, 603 (M+H)$^+$, $C_{26}H_{42}N_7O_7Cl$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.91 (3H, t, J=7.1 Hz), 1.25–1.60 (16H, m), 1.90–2.10 (2H, m), 3.60–3.80 (5H, m), 3.85–4.13 (3H, m), 4.15 (1H, dd, J=10.4, 10.4 Hz), 4.41 (1H, m), 5.68 (1H, brs), 8.17 (1H, brs), 8.32 (1H, s).

EXAMPLE 23

Preparation of SPK135

To 2-bromohexadecanoic acid (1 g), after having been dissolved in acetonitrile (50 ml), were added calcium chloride (5 g) and tetramethylammonium chloride (1 g), and the mixture was heated under reflux for 6 hours. The reaction mixture was filtered, concentrated and distributed into chloroform and water, and the chloroform layer was dried over anhydrous sodium sulfate and concentrated to give 2-chlorohexadecanoic acid (0.80 g). 2-Chlorohexadecanoic acid (893 mg), para-nitrophenol (428 mg) and N,N'-dicyclohexylcarbodiimide (634 mg) were dissolved in N,N-dimethylformamide (DMF), and the mixture was stirred for 12 hours. Precipitates were removed by filtration, and DMF was removed by distillation to give the active ester of 2-chlorohexadecanoic acid. To the active ester, which was dissolved in DMF (500 mg), were added again 6-(4'-N-glycyl-spicaminyl-amino)purine hydrochloride (465 mg) and triethylamine (1.2 ml), and the mixture was stirred for 12 hours. The reaction mixture was concentrated, and the residue was subjected to chromatography on a silica gel column with eluent systems of chloroform-methanol (from 7:1 to 5:1) to give SPK135 in the yield of 262 mg.

Physicochemical properties of SPK135

(1) Melting point: 166°–168° C.,
(2) Elementary analysis:

|  | C | H | O | N |
|---|---|---|---|---|
| Calculated (%) | 54.91, | 7.68, | 17.07, | 14.94, |
| Found (%) | 55.20, | 7.51, | 16.93, | 14.86, |

(3) FD mass spectrum (m/z): 678, 680 (M+Na)$^+$, $C_{30}H_{50}N_7O_7Cl$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.89 (3H, t, J=7.1 Hz), 1.20–1.60 (24H, m), 1.80–2.10 (2H, m), 3.60–4.00 (8H, m), 4.14 (1H, dd, J=10.3 Hz), 4.38 (1H, dd, J=5.7, 8.0 Hz), 5.63 (1H, brs), 8.12 (1H, brs), 8.31 (1H, s).

EXAMPLE 24

Preparation of SPK159

2-Hydroxydodecanoic acid (1 g) dissolved in 10% hydrochloric acid-methanol solution (20 ml) was stirred at room temperature for 1 hour. the reaction mixture was concentrated and distributed into chloroform and water. The chloroform layer was further washed with a 1% aqueous sodium bicarbonate solution and water, dried over anhydrous sodium sulfate and concentrated to give the methyl ester of 2-hydroxydodecanoic acid (1.02 g). To the methyl ester of 2-hydroxydodecanoic acid, after having been dissolved in pyridine (20 ml), was added paratoluenesulfonyl chloride (0.9 g), and the mixture was stirred for 8 hours. After the pyridine was removed by distillation, the residue was distributed into chloroform and water and the chloroform layer was dried with anhydrous sodium sulfate, concentrated and then subjected to chromatography on a silica gel column with an eluent system of n-hexane-ethyl (50:1) to give the methyl ester of 2-paratoluenesulfonyloxydodecanoic acid (1.43 g). After the total product was dissolved in acetonitrile (50 ml) and 5 ml of 1M solution of tetra-n-butylammonium fluoride in tetrahydrofuran was added, the mixture was stirred for 48 hours. The reaction mixture was then concentrated, and the residue was subjected to chromatography on a silica gel column with an eluent system of n-hexane-ethyl acetate (100:1) to give the methyl ester of 2-fluorododecanoic acid (480 mg). The product was dissolved in a mixed solvent of ethanol-water (1:1). Potassium hydroxide (0.6 g) was added to the solution, and the mixture was stirred at 80° C. for 30 minutes. After the reaction mixture was concentrated and adjusted to a weak acidic range of pH by adding water and an excessive amount of citric acid, it was extracted with ethyl acetate. The ethyl acetate layer was dried over anhydrous sodium sulfate and concentrated to give 2-fluorododecanoic acid (420 mg).

After 2-fluorododecanoic acid thus obtained (420 mg) and para-nitrophenol (267 mg) were dissolved in N,N-dimethylformamide (DMF, 30 ml), N,N'-dicyclohexylcarbodiimide (395 mg) was added, and the mixture was stirred for 12 hours. The reaction mixture was filtered and concentrated to give the active ester of 2-fluorododecanoic acid. To the active ester (326 mg), after having been dissolved in DMF, were added 6-(4'-N-glycyl-spicaminyl-amino)purine trifluoroacetate (565 mg) and triethylamine (1.0 ml), and the mixture was stirred for 12 hours. After the solvent was removed by distillation, the residue was subjected to chromatography on a silica gel column with eluent systems of chloroform-methanol (from 7:1 to 5:1) to give SPK159 in the yield of 153 mg.

Physicochemical properties of SPK159
(1) Melting point: 187°–189° C.,
(2) Elementary analysis:

|  | C | H | O | N |
|---|---|---|---|---|
| Calculated (%) | 53.50, | 7.25, | 19.19, | 16.80, |
| Found (%) | 53.23, | 7.40, | 19.29, | 16.62, |

(3) FD mass spectrum (m/z): 607 (M+Na+H)$^+$, $C_{26}H_{42}N_7O_7F$ (4) Infrared spectrum (KBr disc): 3400 cm$^{-1}$, 1620 cm$^{-1}$, (5) Proton nuclear magnetic resonance spectrum (500 MHz, in CD$_3$OD) $\delta_H$: 0.89 (3H, t, J=7.0 Hz), 1.20–1.53 (16H, m), 1.80–2.00 (2H, m), 3.60–4.05 (8H, m), 4.15 (1H, t, J=10.2 Hz) 4.95 (1H, dm, J=50 Hz), 5.65 (1H, brs), 8.15 (1H, s), 8.31 (1H, s).

EXAMPLE 25

Preparation of SPK233

2-Hydroxyhexadecanoic acid (1 g) dissolved in 10% hydrochloric acid-methanol solution (20 ml) was stirred at room temperature for 1 hour. The reaction mixture was concentrated and distributed into chloroform and water. The chloroform layer was further washed with a 1% aqueous sodium bicarbonate solution and water, dried with anhydrous sodium sulfate and concentrated to give the methyl ester of 2-hydroxyhexadecanoic acid (1.01 g). To the methyl ester of 2-hydroxyhexadecanoic acid (1.01 g), after having been dissolved in pyridine (20 ml), was added paratoluenesulfonyl chloride (0.67 g), and the mixture was stirred for 8 hours. After the pyridine had been removed by distillation, the residue was distributed into chloroform and water and the chloroform layer was dried with anhydrous sodium sulfate, concentrated and then subjected to chromatography on a silica gel column with an eluent system of n-hexane-ethyl acetate (50:1) to give the methyl ester of 2-paratoluenesulfonyloxy-hexadecanoic acid (1.43 g). After the total product was dissolved in acetonitrile (30 ml) and 5 ml of 1M solution of tetra-n-butylammonium fluoride in tetrahydrofuran was added, the mixture was stirred for 48 hours. The reaction mixture was then concentrated, and the residue was subjected to chromatography on a silica gel column with an eluent system of n-hexane-ethyl acetate (100:1) to give the methyl ester of 2-fluorohexadecanoic acid (480 mg). The product was dissolved in a mixed solvent of ethanol-water (1:1). Potassium hydroxide (0.6 g) was added to the solution, and the mixture was stirred at 80° C. for 30 minutes. After the reaction mixture was concentrated and adjusted to a weak acidic range of pH by adding water and an excessive amount of citric acid, it was extracted with ethyl acetate. The ethyl acetate layer was dried over anhydrous sodium sulfate and concentrated to give 2-fluorohexadecanoic acid (390 mg).

After 2-fluorohexadecanoic acid thus obtained (390 mg) and para-nitrophenol (200 mg) were dissolved in N,N-dimethylformamide (DMF, 30 ml), N,N'-dicyclohexylcarbodiimide (300 mg) was added, and the mixture was stirred for 12 hours. The reaction mixture was filtered and concentrated to give the active ester of 2-fluorohexadecanoic acid (510 mg). To the active ester (510 mg), after having been dissolved in DMF, were added 6-(4'-N-glycyl-spicaminyl-amino)purine trifluoroacetate (495 mg) and triethylamine (1.0 ml), and the mixture was stirred for 12 hours. After the solvent was removed by distillation, the residue was subjected to chromatography on a silica gel column with eluent systems of chloroform-methanol (from 7:1 to 5:1) to give SPK233 in the yield of 118 mg.

Physicochemical properties of SPK233
(1) Melting point: 174°–175° C.,
(2) Elementary analysis:

|  | C | H | O | N |
|---|---|---|---|---|
| Calculated (%) | 56.32, | 7.88, | 17.51, | 15.33, |
| Found (%) | 56.60, | 7.66, | 17.43, | 15.59, |

(3) FD mass spectrum (m/z): 640 (M+H)$^+$, $C_{30}H_{50}N_7O_7F$ (4) Infrared spectrum (KBr disc): 3400 cm$^{-1}$, 1630 cm$^{-1}$, (5) Proton nuclear magnetic resonance spectrum (500 MHz, in CD$_3$OD) $\delta_H$: 0.90 (3H, t, J=7.1 Hz), 1.20–2.10 (26H, m), 3.60–3.80 (5H, m), 3.85–4.05 (3H, m), 4.15 (1H, dd, J=10.4, 10.4 Hz), 4.95 (1H, dm, J=50 Hz), 5.68 (1H, brs), 8.15 (1H, s), 8.32 (1H, s).

EXAMPLE 26

Preparation of SPK87

To 2-hydroxydodecanoic acid (1.0 g) and N-hydroxysuccinimide (540 mg) dissolved in N,N-dimethylformamide (DMF, 30 ml) was added N,N'-dicyclohexylcarbodiimide (960 mg), and the mixture was stirred for 12 hours. The reaction mixture was filtered and concentrated to give an active ester of 2-hydroxydodecanoic acid. To the active ester (500 mg), after dissolved in DMF, were added 6-(4'-N-glycyl-spicaminyl-amino)purine hydrochloride (612 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK87 in the yield of 238 mg.

47

Physicochemical properties of SPK87
(1) Melting point: 190°–192° C.,
(2) Elementary analysis:

|  | C | H | O | N |
|---|---|---|---|---|
| Calculated (%) | 53.69, | 7.45, | 22.00, | 16.86, |
| Found (%) | 53.90, | 7.19, | 21.74, | 17.17, |

(3) FD mass spectrum (m/z): 582 (M+H)$^+$, $C_{26}H_{43}N_7O_7$
(4) Infrared spectrum (KBr disc): 3400 cm$^{-1}$, 1630 cm$^{-1}$,
(5) Proton nuclear magnetic resonance spectrum (500 MHz, in CD$_3$OD) $\delta_H$: 0.88 (3H, t, J=7.1 Hz), 1.20–1.80 (18H, m), 3.60–3.80 (5H, m), 3.80–4.10 (4H, m), 4.15 (1H, dd, J=10.4, 10.4 Hz), 5.62 (1H, brs), 8.10 (1H, s), 8.25 (1H, s).

EXAMPLE 27

Preparation of SPK112

To 2-hydroxyhexadecanoic acid (500 mg) dissolved in N,N-dimethylformamide (DMF, 40 ml) were added N-hydroxysuccinimide (211 mg) and N,N'-dicyclohexylcarbodiimide (379 mg), and the mixture was stirred for 12 hours. The reaction mixture was filtered and DMF was removed by distillation to give the active ester of 2-hydroxyhexadecanoic acid. To the active ester (250 mg), after having been dissolved in DMF (250 mg), were added 6- (4'-N-spicaminyl-amino)purine hydrochloride (259 mg) and triethylamine (2.0 ml), and the mixture was stirred for 12 hours. The DMF was removed by distillation, and the residue was subjected to chromatography on a silica gel column with eluent systems of chloroform-methanol (from 7:1 to 5:1) to give SPK112 in the yield of 137 mg.

Physicochemical properties of SPK112
(1) Melting point: 238°–240° C.,
(2) Elementary analysis:

|  | C | H | O | N |
|---|---|---|---|---|
| Calculated (%) | 56.50, | 8.06, | 20.07, | 15.37, |
| Found (%) | 56.77, | 8.00, | 19.98, | 15.25, |

(3) FD mass spectrum (m/z): 660 (M+Na)$^+$, $C_{30}H_{51}N_7O_8$
(4) Infrared spectrum (KBr disc): 3400 cm$^{-1}$, 1630 cm$^{-1}$,
(5) Proton nuclear magnetic resonance spectrum (500 MHz, in CDCl$_3$-CD$_3$OD) $\delta_H$: 0.89 (3H, t, J=7.1 Hz), 1.20–1.85 (26H, m), 3.60–4.05 (8H, m), 4.08 (1H, m), 4.17 (1H, dd, J=10.3 Hz), 5.65 (1H, brs), 8.09 (1H, brs), 8.30 (1H, s).

EXAMPLE 28

Preparation of SPK88

To 3-hydroxydodecanoic acid (1.0 g) and N-hydroxysuccinimide (540 mg) dissolved in N,N-dimethylformamide (DMF, 30 ml) was added N,N'-dicyclohexylcarbodiimide (960 mg), and the mixture was stirred for 12 hours. The reaction mixture was filtered and concentrated to give the active ester of 3-hydroxydodecanoic acid. To the active ester (500 mg), after dissolved in DMF, were added 6-(4'-N-glycyl-spicaminyl-amino)purine hydrochloride (620 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK88 in the yield of 223 mg.

48

Physicochemical properties of SPK88
(1) Melting point: 233°–236° C.,
(2) Elementary analysis:

|  | C | H | O | N |
|---|---|---|---|---|
| Calculated (%) | 53.69, | 7.45, | 22.00, | 16.86, |
| Found (%) | 53.82, | 7.20, | 21.86, | 17.12, |

(3) FD mass spectrum (m/z): 582 (M+H)$^+$, $C_{26}H_{43}N_7O_8$
(4) Infrared spectrum (KBr disc): 3400 cm$^{-1}$, 1630 cm$^{-1}$,
(5) Proton nuclear magnetic resonance spectrum (500 MHz, in CD$_3$OD) $\delta_H$: 0.90 (3H, t, J=7.1 Hz), 1.20–1.60 (16H, m), 2.28–2.50 (2H, m), 3.60–4.05 (9H, m), 4.15 (1H, dd, J=10.4, 10.4 Hz), 5.67 (1H, brs), 8.12 (1H, s), 8.31 (1H, s).

EXAMPLE 29

Preparation of SPK115

To 3-hydroxyhexadecanoic acid (1.0 g) and N-hydroxysuccinimide (423 mg) dissolved in N,N-dimethylformamide (DMF, 30 ml) was added N,N'-dicyclohexylcarbodiimide (757 mg), and the mixture was stirred for 12 hours. The reaction mixture was filtered and concentrated to give the active ester of 3-hydroxyhexadecanoic acid. To the active ester (500 mg), after having been dissolved in DMF, were added 6-(4'-N-glycyl-spicaminyl-amino)purine hydrochloride (519 mg) and triethylamine (2 ml), and the mixture was stirred for 12 hours. The solvent was removed by distillation, and the residue was subjected to chromatography on a silica gel column with eluent systems of chloroform-methanol (from 7:1 to 5:1) to give SPK115 in the yield of 205 mg.

Physicochemical properties of SPK115
(1) Melting point: 215°–217° C.,
(2) Elementary analysis:

|  | C | H | O | N |
|---|---|---|---|---|
| Calculated (%) | 56.50, | 8.06, | 20.07, | 15.37, |
| Found (%) | 56.80, | 8.15, | 19.97, | 15.08, |

(3) FD mass spectrum (m/z): 642 (M+Na-H$_2$O)$^+$, $C_{30}H_{51}N_7O_8$
(4) Infrared spectrum (KBr disc): 3400 cm$^{-1}$, 1630 cm$^{-1}$,
(5) Proton nuclear magnetic resonance spectrum (500 MHz, in CD$_3$OD) $\delta_H$: 0.90 (3H, t, J=7.1 Hz), 1.20–1.60 (24H, m), 2.30–2.50 (2H, m), 3.60–4.10 (9H, m), 4.14 (1H, t, J=10.3 Hz), 5.69 (1H, brs), 8.15 (1H, brs), 8.31 (1H, s).

EXAMPLE 30

Preparation of SPK410

To 11-bromoundecanoic acid (1.73 g) dissolved in N,N-dimethylformamide (DMF) was added sodium azide (1.5 g), and the mixture was heated to a temperature of 80° C. and stirred for 5 hours. The reaction mixture was then diluted with cooling water and extracted with ethyl acetate to give 11-azidoundecanoic acid. To the mixed solution of 11-azidoundecanoic acid (1 g) and para-nitrophenol (612 mg) in DMF was added N,N'-dicyclohexylcarbodiimide (920 mg), and the mixture was stirred for 12 hours. The reaction mixture was filtered and concentrated to give the active ester of 11-azidoundecanoic acid. To the active ester (284 mg) dissolved in DMF were further added 6-(4'-N-glycyl-spicaminyl-amino)purine hydrochloride (300 mg) and triethylamine (1.1 ml), and the mixture was stirred for 12 hours. The solvent was removed by distillation, and the residue was subjected to chromatography on a silica gel column with eluent systems of chloroform-methanol (from 7:1 to 5:1) to give SPK410 in the yield of 171 mg.

Physicochemical properties of SPK410
 (1) Melting point: 182°–183° C.,
 (2) Specific rotation $[\alpha]_D^{25}$=+6.0° (c=0.1, in methanol),
 (3) Elementary analysis:

|  | C | H | O | N |
|---|---|---|---|---|
| Calculated (%) | 50.67, | 6.80, | 18.90, | 23.63, |
| Found (%) | 50.38, | 6.99, | 19.10, | 23.53, |

(4) FD mass spectrum (m/z): 593 (M+H)$^+$, $C_{25}H_{40}N_{10}O_7$
 (5) Infrared spectrum (KBr disc): 3400 cm$^{-1}$, 2110 cm$^{-1}$, 1630 cm$^{-1}$,
 (6) Proton nuclear magnetic resonance spectrum (500 MHz, in CD$_3$OD) $\delta_H$: 1.25–1.50 (12H, m), 1.55–1.70 (4H, m), 2.30 (2H, t, J=7.0 Hz), 3.30 (2H, t, J=7.0 Hz), 3.60–3.80 (5H, m), 3.86 (1H, d, J=16.6 Hz), 3.89 (1H, d, J=16.6 Hz), 4.00 (1H, dd, J=2.1, <1 Hz), 4.14 (1H, dd, J=10.4, 10.4 Hz), 5.64 (1H, brs), 8.16 (1H, s), 8.32 (1H, s).

EXAMPLE 31

Preparation of SPK126

To 12-bromodecanoic acid (1 g) dissolved in N,N-dimethylformamide (DMF) was added sodium azide (2.0 g), and the mixture was heated to 80° C. and refluxed for 5 hours. The reaction mixture was then cooled by adding water and extracted with ethyl acetate to give 12-azidododecanoic acid (0.81 g).

To the mixed solution of 12-azidododecanoic acid (0.81 g) and para-nitrophenol (0.47 g) in DMF was added N,N'-dicyclohexylcarbodiimide (0.69 g), and the mixture was stirred for 12 hours. The reaction mixture was filtered and concentrated to give the active ester of 12-azidododecanoic acid. To the active ester (472 mg) dissolved in DMF were further added 6-(4'-N-glycyl-spicaminyl-amino)purine hydrochloride (500 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK126 in the yield of 189 mg.

Physicochemical properties of SPK126
 (1) Melting point: 202°–203° C.,
 (2) Specific rotation $[\alpha]_D^{24}$=+24° (c=0.1, in methanol),
 (3) Elementary analysis:

|  | C | H | O | N |
|---|---|---|---|---|
| Calculated (%) | 51.47, | 6.98, | 18.46, | 23.09, |
| Found (%) | 51.57, | 6.81, | 18.30, | 23.32, |

(4) FD mass spectrum (m/z): 607 (M+H)$^+$, $C_{26}H_{42}N_{10}O_7$
 (5) Infrared spectrum (KBr disc): 3400 cm$^{-1}$, 2080 cm$^{-1}$, 1630 cm$^{-1}$,
 (6) Proton nuclear magnetic resonance spectrum (500 MHz, in CD$_3$OD) $\delta_H$: 1.20–1.70 (18H, m), 2.27 (2H, t, J=7.1 Hz), 3.26 (2H, t, J=7.1 Hz), 3.65–3.80 (5H, m), 3.85 (1H, d, J=16.4 Hz), 3.90 (1H, d, J=16.4 Hz), 4.05 (1H, dd, J=2.1, <1 Hz), 4.15 (1H, dd, J=10.4, 10.4 Hz), 5.60 (1H, brs), 8.02 (1H, s), 8.22 (1H, s).

EXAMPLE 32

Preparation of SPK226

To the suspension of 16-hydroxyhexadecanoic acid (0.7 g) in dichloromethane. (20 ml) was added triethylamine (1.80 ml). Methanesulfonyl chloride (0.8 ml) was added dropwise to the reaction mixture while it was ice-cooled and stirred. Stirring was continued directly at 0° C. for 1 hour. The reaction mixture was extracted with chloroform, and the chloroform layer was washed with 1% aqueous sodium hydrogen carbonate and then with water, dried with anhydrous sodium sulfate and concentrated. The residue was subjected to chromatography on a silica gel column with an eluent system of chloroform-methanol (3:1) to give 16-methanesulfonyloxyhexadecanoic acid (0.74 g). To 16-methanesulfonyloxyhexadecanoic acid (325 mg) dissolved in N,N-dimethylformamide (DMF, 15 ml) was added sodium azide (268 mg), and the mixture was stirred at 80° C. for 12 hours. The reaction mixture, after having been cooled, was then distributed into ethyl acetate and water, and the ethyl acetate layer was dried over anhydrous sodium sulfate to give 16-azidohexadecanoic acid (235 mg). To the solution of 16-azidohexadecanoic acid (226 mg) in DMF were added N-hydroxysuccinimide (90 mg) and N,N'-dicyclohexylcarbodiimide (160 mg), and the mixture was stirred for 48 hours. The reaction mixture was filtered and concentrated to give the active ester of 16-azidohexadecanoic acid. To the active ester dissolved in DMF were further added 6-(4'-N-glycyl-spicaminyl-amino)purine hydrochloride (310 mg) and triethylamine (1 ml), and the mixture was stirred for 24 hours. The solvent was removed by distillation, and the residue was subjected to chromatography on a silica gel column with an eluent system of chloroform-methanol (6:1) to give SPK226 in the yield of 92 mg.

Physicochemical properties of SPK226
 (1) Melting point: 182°–183° C.,
 (2) Specific rotation $[\alpha]_D$=25 0° (c=0.1, in methanol),
 (3) Elementary analysis:

|  | C | H | O | N |
|---|---|---|---|---|
| Calculated (%) | 54.37, | 7.60, | 16.89, | 21.13, |
| Found (%) | 54.15, | 7.89, | 16.92, | 21.04, |

(4) FD mass spectrum (m/z): 663 (M+H)$^+$, $C_{30}H_{50}N_{10}O_7$
 (5) Infrared spectrum (KBr disc): 3400 cm$^{-1}$, 2110 cm$^{-1}$, 1630 cm$^{-1}$,
 (6) Proton nuclear magnetic resonance spectrum (500 MHz, in CD$_3$OD) $\delta_H$: 1.20–1.70 (26H, m), 2.29 (2H, t, J=7.0 Hz), 3.28 (2H, t, J=6.5 Hz), 3.60–3.80 (5H, m), 3.87 (1H, d, J=15.0 Hz), 3.90 (1H, d, J=15.0 Hz), 4.03 (1H, dd, J=2.5, <1 Hz), 4.16 (1H, dd, J=10.3, 10.3 Hz), 5.65 (1H, brs), 8.12 (1H, brs), 8.32 (1H, s).

EXAMPLE 33

Preparation of SPK229

To the solution of 2-bromohexadecanoic acid (1.00 g) in N,N-dimethylformamide (DMF, 15 ml) was added sodium azide (0.86 g), and the mixture was stirred at 80° C. for 12 hours. To the reaction mixture, after having been cooled to room temperature, was then added water. The mixture was extracted with ethyl acetate, and the ethyl acetate layer was separated, washed twice with brine, dried over anhydrous sodium sulfate. The solvent was removed by distillation to give 2-azidohexadecanoic acid (0.73 g). To the solution of 2-azidohexadecanoic acid in DMF were added N-hydroxysuccinimide (74 mg) and N,N'-dicyclohexylcarbodiimide (146 mg), and the mixture was stirred for 12 hours. Precipitates produced was removed by filtration, and the filtrate was concentrated to give the active ester of 2-azidohexadecanoic acid. To the active ester in DMF were further added 6-(4'-N-glycyl-spicaminyl-amino)purine hydrochloride (246 mg) and triethylamine (0.72 ml), and the mixture was stirred for 12 hours. The solvent was removed by distillation, and the residue was subjected to chromatography on a silica gel column with an eluent system of chloroform-methanol (6:1) to give SPK229 in the yield of 185 mg.

Physicochemical properties of SPK229

(1) Melting point: 184°–185° C.,
(2) Elementary analysis:

|  | C | H | O | N |
|---|---|---|---|---|
| Calculated (%) | 54.37, | 7.60, | 16.90, | 21.13, |
| Found (%) | 54.11, | 7.88, | 17.12, | 20.89, |

(3) FD mass spectrum (m/z): 663 (M+H)$^+$, $C_{30}H_{50}N_{10}O_7$ (4) Infrared spectrum (KBr disc): 3400 cm$^{-1}$, 2120 cm$^{-1}$, 1630 cm$^{-1}$, (5) Proton nuclear magnetic resonance spectrum (500 MHz, in CDCl$_3$-CD$_3$OD) $\delta_H$: 0.89 (3H, t, J=7.0 Hz), 1.20–1.52 (24H, m), 1.78–1.95 (2H, m), 3.60–3.80 (5H, m), 3.86–4.02 (3H, m), 4.05 (1H, dd, J=2.0, <1 Hz), 4.18 (1H, dd, J=10.3, 10.3 Hz), 5.65 (1H, brs), 8.09 (1H, brs), 8.30 (1H, s).

EXAMPLE 34

Preparation of SPK416

To the solution of 11-cyanoundecanoic acid (1.00 g) and para-nitrophenol (660 mg) in N,N-dimethylformamide (DMF, 30 ml) was added N,N'-dicyclohexylcarbodiimide (980 mg), and the mixture was stirred for 12 hours. The reaction mixture was filtered and concentrated to give the active ester of 11-cyanoundecanoic acid. To the active ester (433 mg) dissolved in DMF were further added 6-(4'-N-glycyl-spicaminyl-amino)purine hydrochloride (500 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK416 in the yield of 173 mg.

Physicochemical properties of SPK416

(1) Melting point: 175°–176° C.,
(2) Specific rotation [α]$_D^{25}$=+0° (c=0.1, in methanol),
(3) Elementary analysis:

|  | C | H | O | N |
|---|---|---|---|---|
| Calculated (%) | 54.16, | 6.99, | 19.42, | 19.43, |
| Found (%) | 53.95, | 7.16, | 19.20, | 19.69, |

(4) FD mass spectrum (m/z): 577 (M+H)$^+$, $C_{26}H_{40}N_8O_7$ (5) Infrared spectrum (KBr disc): 3400 cm$^{-1}$, 2250 cm$^{-1}$, 1630 cm$^{-1}$, (6) Proton nuclear magnetic resonance spectrum (500 MHz, in CD$_3$OD) $\delta_H$: 1.20–1.70 (16H, m), 2.27 (2H, t, J=7.1 Hz), 2.42 (2H, t, J=7.1 Hz), 3.60–3.80 (5H, m), 3.85 (1H, d, J=16.4 Hz), 3.90 (1H, d, J=16.4 Hz), 4.00 (1H, dd, J=2.1, <1 Hz), 4.15 (1H, dd, J=10.4, 10.4 Hz), 5.69 (1H, brs), 8.15 (1H, brs), 8.30 (1H, s).

EXAMPLE 35

Preparation of SPK177

16-Hydroxyhexadecanoic acid (1 g) dissolved in a mixed solution of 10% methanolic hydrochloric acid-methylene chloride (5:1) was stirred for 1 hour. The reaction mixture was then concentrated and distributed into chloroform and water. The chloroform layer was washed with a 1% aqueous sodium bicarbonate solution and water, dried with anhydrous sodium sulfate and concentrated to give the methyl ester of 16-hydroxyhexadecanoic acid (1.04 g).

To the methyl ester of 16-hydroxyhexadecanoic acid (1.04 g) dissolved in methylene chloride (20 ml) was added pyridine (1 ml), and the mixture was stirred under ice-cooling. Paratoluenesulfonyl chloride (0.73 g) was added to the mixture, and the stirring was continued for 3 hours. The reaction mixture was distributed into chloroform and water, and the chloroform layer was dried with anhydrous sodium sulfate and concentrated. The residue thus obtained was subjected to chromatography on a silica gel column with an eluent system of n-hexane-ethyl acetate (100:1) to give the methyl ester of 16-paratoluenesulfonyloxyhexadecanoic acid (1.58 g).

The methyl ester of 16-paratoluenesulfonyloxy-hexadecanoic acid (600 mg) was dissolved in dimethylsulfoxide (DMSO). Sodium cyanide (250 mg) was added to the solution, and the mixture was stirred at 80° C. for 5 hours. After the reaction mixture was cooled, it was distributed into diethyl ether and water. The diethyl ether layer is dried over anhydrous sodium sulfate and concentrated to give the methyl ester of 16-cyanohexadecanoic acid (370 mg). The product was dissolved in a mixed solvent of ethanol-water (1:1), and lithium hydroxide (180 mg) was added to the solution. The mixture was stirred at 80° C. for 30 minutes. The reaction mixture was cooled and ethanol was removed by distillation and extracted with ethyl acetate which had been adjusted to a weak acidic range of pH by adding citric acid. The ethyl acetate layer was dried and concentrated to give 16-cyanohexadecanoic acid (316 mg).

After 16-cyanohexadecanoic acid thus obtained (225 mg) and para-nitrophenol (111 mg) were dissolved in N,N-dimethylformamide (DMF, 30 ml), N,N'-dicyclohexylcarbodiimide (167 mg) was added, and the mixture was stirred for 12 hours. The reaction mixture was filtered and concentrated to give the active ester of 16-cyanohexadecanoic acid. To the active ester (323 mg), after having been dissolved in DMF, were added 6-(4'-N-glycyl-spicaminyl-amino)purine hydrochloride (317 mg) and triethylamine (1.0 ml), and the mixture was stirred for 12 hours. After the solvent was removed by distillation, the residue was subjected to chromatography on a silica gel column with eluent systems of chloroform-methanol (from 7:1 to 5:1) to give SPK177 in the yield of 95.8 mg.

Physicochemical properties of SPK177

(1) Melting point: 162°–163° C.,
(2) Specific rotation [α]$_D^{25}$=−1.6° (c=0.1, in methanol),
(3) Elementary analysis:

|  | C | H | O | N |
|---|---|---|---|---|
| Calculated (%) | 57.57, | 7.79, | 17.32, | 17.32, |
| Found (%) | 57.28, | 8.01, | 17.57, | 17.14, |

(4) FD mass spectrum (m/z): 669 (M+Na)$^+$, $C_{31}H_{50}N_8O_7$ (5) Infrared spectrum (KBr disc): 3400 cm$^{-1}$, 2250 cm$^{-1}$, 1630 cm$^{-1}$, (6) Proton nuclear magnetic resonance spectrum (500 MHz, in CD$_3$OD) $\delta_H$: 1.20–1.70 (26H, m), 2.26 (2H, t, J=7.3

Hz), 2.40 (2H, t, J=7.3 Hz), 3.65–3.80 (5H, m), 3.86 (1H, d, J=16.0 Hz), 3.89 (1H, d, J=16.0 Hz), 4.02 (1H, dd, J=2.3, <1 Hz), 4.15 (1H, dd, J=10.3, 10.3 Hz), 5.62 (1H, brs), 8.05 (1H, brs), 8.22 (1H, s).

EXAMPLE 36

Preparation of SPK422

To a solution of 11-phenoxyundecanoic acid (1 g) and para-nitrophenol (499 mg) in N,N-dimethylformamide (DMF, 30 ml) was added N,N'-dicyclohexylcarbodiimide (741 mg), and the mixture was stirred for 12 hours. The reaction mixture was filtered and concentrated to give the active ester of 11-phenoxyundecanoic acid. To the active ester (532 mg) dissolved in DMF were further added 6-(4'-N-glycyl-spicaminyl-amino)purine hydrochloride (400 mg) and triethylamine (5.0 ml), and the mixture was stirred for 12 hours. The solvent was removed by distillation, and the residue was subjected to chromatography on a silica gel column with eluent systems of chloroform-methanol (from 7:1 to 5:1) to give SPK422 in the yield of 245 mg.

Physicochemical properties of SPK422

(1) Melting point: 187°–188° C., (2) Specific rotation $[\alpha]_D^{25}$=+10.0° (c=0.1, in methanol), (3) Elementary analysis:

|  | C | H | O | N |
|---|---|---|---|---|
| Calculated (%) | 57.84, | 7.05, | 19.88, | 15.23, |
| Found (%) | 57.60, | 7.30, | 20.09, | 15.01, |

(4) FD mass spectrum (m/z): 644 (M+H)$^+$, $C_{31}H_{45}N_7O_8$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 1.30–1.80 (16H, m), 2.30 (2H, t, J=7.0 Hz), 3.60–3.80 (5H, m), 3.87 (1H, d, J=16.0 Hz), 3.90 (1H, d, J=16.0 Hz), 3.95 (1H, t, J=7.0), 4.00 (1H, dd, J=2.0, <1 Hz), 4.15 (1H, dd, J=10.3, 10.3 Hz), 5.68 (1H, brs), 6.90 (3H, m), 7.22 (2H, t, J=7.3 Hz), 8.15 (1H, brs), 8.31 (1H, s).

EXAMPLE 37

Preparation of SPK186

12-Bromododecanoic acid (1 g) was stirred in 10% hydrochloric acid-methanol for 4 hours. The mixture was then concentrated and distributed into chloroform and water, and the chloroform layer was dried with anhydrous sodium sulfate to give the methyl ester of 12-bromoundecanoic acid (1.01 g). To para-fluorophenol (0.38 g) dissolved in dimethylformamide (DMF) was added 60% NaH (0.40 g), and the mixture was stirred. To this mixture was added 12-bromododecanoic acid (1 g), and the mixture was stirred for 12 hours. The reaction mixture, after having been concentrated and adjusted to a weak acidic range of pH by adding citric acid, was extracted with ethyl acetate. The ethyl acetate layer was dried and concentrated to give 12-para-fluorophenoxydodecanoic acid (1.12 g). The product was dissolved in a mixed solvent of ethanol-water (1:1), and potassium hydroxide (0.6 g) was added to the solution. The mixture was stirred at 80° C. for 30 minutes. The reaction mixture was diluted with water (80 ml), adjusted to acidic range of pH by adding citric acid, and extracted with ethyl acetate. The ethyl acetate layer was dried over anhydrous sodium sulfate and concentrated to give 12-para-fluorophenoxydodecanoic acid (1.03 g).

After para-fluorophenoxydodecanoic acid thus obtained (1 g) and para-nitrophenol (0.36 g) were dissolved in N,N-dimethylformamide (DMF, 30 ml), N,N'-dicyclohexylcarbodiimide (167 mg) was added, and the mixture was stirred for 12 hours. The reaction mixture was filtered and concentrated to give the active ester of 12-para-fluorophenoxydodecanoic acid. To the active ester (644 mg), after having been dissolved in DMF, were added 6-(4'-N-glycyl-spicaminyl-amino)purine hydrochloride (500 mg) and triethylamine (2.0 ml), and the mixture was stirred for 12 hours. After the solvent was removed by distillation, the residue was subjected to chromatography on a silica gel column with eluent systems of chloroform-methanol (from 7:1 to 5:1) to give SPK186 in the yield of 215 mg.

Physicochemical properties of SPK186

(1) Melting point: 218°–219° C., (2) Specific rotation $[\alpha]_D^{25}$=+6.4° (c=0.1, in methanol), (3) Elementary analysis:

|  | C | H | O | N |
|---|---|---|---|---|
| Calculated (%) | 56.88, | 6.86, | 18.94, | 14.51, |
| Found (%) | 56.97, | 6.70, | 18.83, | 14.70, |

(4) FD mass spectrum (m/z): 676 (M+H)$^+$, $C_{32}H_{46}N_7O_8F$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.89 (3H, t, J=7.1 Hz), 1.20–1.80 (18H, m), 2.30 (2H, t, J=7.1 Hz), 3.60–3.80 (5H, m), 3.86 (1H; d, J=16.4 Hz), 3.90 (1H, d, J=16.4 Hz), 3.92 (1H, t, J=7.1 Hz), 4.00 (1H, dd, J=2.1, <1 Hz), 4.15 (1H, dd, J=10.4 Hz), 5.60 (1H, brs), 6.82 (2H, dd, J=4.6, 9.1 Hz), 6.96 (2H, dd, J=9.1, 9.1 Hz), 8.12 (1H, brs), 8.30 (1H, s).

EXAMPLE 38

Preparation of SPK228

16-Hydroxyhexadecanoic acid (0.5 g) was suspended in methylene chloride (15 ml), and triethylamine (1.03 ml) was added to the suspension. To the mixture, while ice-cooled and stirred, was added dropwise acetyl chloride (0.39 ml). After 8 hours ice was added, and extracted with chloroform. The chloroform layer was washed with a saturated sodium hydrogen carbonate solution and then twice with water and dried with anhydrous sodium sulfate. The chloroform layer was concentrated and the residue thus obtained was subjected to chromatography on a silica gel column with an eluent system of chloroform-hexane (2:1) to give 16-acetoxyhexadecanoic acid (0.58 g).

16-Acetoxyhexadecanoic acid (236 mg) was dissolved in N,N-dimethylformamide (DMF, 3.5 ml). N-Hydroxysuccinimide (87 mg) and N,N'-dicyclohexylcarbodiimide (170 mg) were added, and the mixture was stirred for 12 hours. The reaction mixture was filtered, and 6-(4'-N-glycyl-spicaminyl-amino)purine hydrochloride (288 mg) and triethylamine (0.84 ml) were added to the filtrate, and the mixture was stirred for 12 hours. The reaction mixture was concentrated, and the residue was subjected to chromatography on a silica gel column with an eluent system of chloroform-methanol (6:1) to give SPK228 in the yield of 167 mg.

Physicochemical properties of SPK228

(1) Melting point: 170°–172° C., (2) Specific rotation $[\alpha]_D^{25}$=+3.2° (c=0.1, in methanol), (3) Elementary analysis:

|               | C      | H     | O      | N      |
|---------------|--------|-------|--------|--------|
| Calculated (%) | 56.54, | 7.86, | 21.18, | 14.42, |
| Found (%)      | 56.26, | 7.99, | 21.30, | 14.45, |

(4) FD mass spectrum (m/z): 680 (M+H)$^+$, $C_{32}H_{53}N_7O_9$ (5) Infrared spectrum (KBr disc): 3400 cm$^{-1}$, 1740 cm$^{-1}$, 1630 cm$^{-1}$, (6) Proton nuclear magnetic resonance spectrum (500 MHz, in CD$_3$OD) $\delta_H$: 1.20–1.70 (26H, m), 2.03 (3H, s), 2.30 (2H, t, J=7.0 Hz), 3.6–3.8 (5H, m), 3.87 (1H, d, J=15.0 Hz), 3.89 (1H, d, J=15.0 Hz), 4.03 (1H, dd, J=2.1, <1 Hz), 4.06 (2H, t, J=7.0 Hz), 4.15 (1H, dd, J=10.3, 10.3 Hz), 5.65 (1H, brs), 8.12 (1H, brs), 8.32 (1H, s).

EXAMPLE 39

Preparation of SPK173

2-Hydroxyhexadecanoic acid (1 g) was dissolved in pyridine, and acetic anhydride (0.62 g) was added to the solution in an ice bath. After 12 hours, the reaction mixture was distributed into chloroform and water, and the chloroform layer was concentrated to give 2-acetoxyhexadecanoic acid (1.10 g). To 2-acetoxyhexadecanoic acid (0.50 g) dissolved in N,N-dimethylformamide (DMF) were added para-nitrophenol (0.22 g) and N,N'-dicyclohexylcarbodiimide (0.33 g), and the mixture was stirred for 8 hours. The reaction mixture was filtered, and 6-(4'-N-glycyl-spicaminyl-amino)purine hydrochloride (0.61 g) and triethylamine (2.0 ml) were added to the filtrate. The mixture was stirred for 12 hours.

The solvent was removed by distillation, and the residue was subjected to chromatography on a silica gel column with an eluent systems of chloroform-methanol (from 7:1 to 5:1) to give SPK173 in the yield of 223 mg.

Physicochemical properties of SPK173

(1) Melting point: 165°–167° C., (2) Elementary analysis:

|               | C      | H     | O      | N      |
|---------------|--------|-------|--------|--------|
| Calculated (%) | 56.54, | 7.86, | 21.18, | 14.42, |
| Found (%)      | 56.78, | 7.59, | 20.85, | 14.78, |

(3) FD mass spectrum (m/z): 703 (M+Na+H)$^+$, $C_{32}H_{53}N_7O_9$ (4) Infrared spectrum (KBr disc): 3400 cm$^{-1}$, 1720 cm$^{-1}$, 1630 cm$^{-1}$, (5) Proton nuclear magnetic resonance spectrum (500 MHz, in CD$_3$OD) $\delta_H$: 0.91 (3H, t, J=7.1 Hz), 1.20–1.90 (26H, m), 2.20 (3H, s), 3.60–3.80 (5H, m), 3.80–4.00 (2H, m), 4.01 (1H, dd, J=2.1, <1 Hz), 4.15 (1H, dd, J=10.4, 10.4 Hz), 4.98 (1H, m), 4.70 (1H, s), 8.20 (1H, s), 8.30 (1H, s).

EXAMPLE 40

Preparation of SPK184

16-Hydroxydodecanoic acid (1 g) was dissolved in pyridine, and propionyl chloride (0.40 g) was added to the solution in an ice bath. After 4 hours of stirring, the reaction mixture was distributed into chloroform and water, and the chloroform layer was dried with anhydrous sodium sulfate and concentrated to give 16-propionyloxydodecanoic acid (1.10 g). To 16-propionyloxydodecanoic acid (0.50 g) dissolved in N,N-dimethylformamide (DMF) were added para-nitrophenol (0.22 g) and N,N'-dicyclohexylcarbodiimide (0.32 g), and the mixture was stirred for 12 hours. The reaction mixture was filtered, and 6-(4'-N-glycyl-spicaminyl-amino)purine hydrochloride (0.58 g) and triethylamine (2.0 ml) were added to the filtrate. The mixture was stirred for 12 hours. The solvent was removed by distillation, and the residue was subjected to chromatography on a silica gel column with an eluent systems of chloroform-methanol (from 7:1 to 5:1) to give SPK184 in the yield of 219 mg.

Physicochemical properties of SPK184

(1) Melting point: 165°–166° C., (2) Specific rotation $[\alpha]_D^{25}$=+4.7° (c=0.1, in methanol), (3) Elementary analysis:

|               | C      | H     | O      | N      |
|---------------|--------|-------|--------|--------|
| Calculated (%) | 57.13, | 7.99, | 20.75, | 14.13, |
| Found (%)      | 56.96, | 8.12, | 20.43, | 14.49, |

(4) FD mass spectrum (m/z): 694 (M+H)$^+$, $C_{33}H_{55}N_7O_9$ (5) Infrared spectrum (KBr disc): 3400 cm$^{-1}$, 1730 cm$^{-1}$, 1630 cm$^{-1}$, (6) Proton nuclear magnetic resonance spectrum (500 MHz, in CD$_3$OD) $\delta_H$: 1.13 (3H, t, J=7.1 Hz), 1.20–1.70 (26H, m), 2.30 (2H, t, J=7.1 Hz), 2.33 (2H, q, J=7.1 Hz), 3.60–3.80 (5H, m), 3.86 (1H, d, J=16.4 Hz), 3.90 (1H, d, J=16.4 Hz), 4.03 (1H, d, J=2.1, <1 Hz), 4.05 (2H, t, J=7.1 Hz), 4.15 (1H, t, J=10.4, 10.4 Hz), 5.65 (1H, brs), 8.10 (1H, brs), 8.31 (1H, s).

EXAMPLE 41

Preparation of SPK145

12-Hydroxydodecanoic acid (1 g) was dissolved in pyridine, and butyroyl chloride (0.59 g) was added to the solution in an ice bath. After 4 hours of stirring, the reaction mixture was distributed into chloroform and water, and the chloroform layer was concentrated to give 12-butyryloxydodecanoic acid (1.28 g).

To 12-butyryloxydodecanoic acid (0.30 g) dissolved in N,N-dimethylformamide (DMF) were added para-nitrophenol (0.15 g) and N,N'-dicyclohexylcarbodiimide (0.22 g), and the mixture was stirred for 8 hours. The reaction mixture was filtered, and 6-(4'-N-glycyl-spicaminyl-amino)purine hydrochloride (0.40 g) and triethylamine (2.0 ml) were added to the filtrate. The mixture was stirred for 12 hours. The solvent was removed by distillation, and the residue was subjected to chromatography on a silica gel column with an eluent systems of chloroform-methanol (from 7:1 to 5:1) to give SPK145 in the yield of 129 mg.

Physicochemical properties of SPK145

(1) Melting point: 173°–174° C., (2) Specific rotation $[\alpha]_D^{24}$=+4.3° (c=0.1, in methanol), (3) Elementary analysis:

|               | C      | H     | O      | N      |
|---------------|--------|-------|--------|--------|
| Calculated (%) | 55.29, | 7.58, | 22.09, | 15.04, |
| Found (%)      | 55.51, | 7.39, | 21.81, | 15.29, |

(4) FD mass spectrum (m/z): 652 (M+H)$^+$, $C_{30}H_{49}N_7O_9$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.92 (3H, t, J=7.1 Hz), 1.20–1.80 (20H, m), 2.28 (4H, m), 3.60–3.80 (5H, m), 3.85 (1H, d, J=16.4 Hz), 3.89 (1H, d, J=16.4 Hz), 4.00 (1H, dd, J=2.1, <1 Hz), 4.05 (2H, t, J=7.4 Hz), 4.14 (1H, dd, J=10.4, 10.4 Hz), 5.62 (1H, brs), 8.12 (1H, s), 8.29 (1H, s).

EXAMPLE 42

Preparation of SPK225

16-Hydroxyhexadecanoic acid (1 g) dissolved in a 10% hydrochloric acid-methanol solution was stirred at room temperature for 1 hour. The mixture was then concentrated and distributed into chloroform and water, and the chloroform layer was washed with a 1% aqueous sodium hydrogen carbonate solution and water, dried with anhydrous sodium sulfate and concentrated to give the methyl ester of 16-hydroxyhexadecanoic acid (1.02 g). To the methyl ester of 16-hydroxyhexadecanoic acid dissolved in pyridine (20 ml) was added methanesulfonyl chloride (0.50 g), and the mixture was stirred for 8 hours. Then, the pyridine was removed by distillation, and the residue was distributed into chloroform and water. The chloroform layer was dried with anhydrous sodium sulfate, concentrated and subjected to chromatography on a silica gel column with an eluent system of n-hexane-ethyl acetate (50:1) to give the methyl ester of 16-methanesulfonyloxy hexadecanoic acid (1.02 g).

To the methyl ester, which was dissolved in a mixed solution of ethanol-water (1:1), was added potassium hydroxide (0.6 g), and the mixture was stirred at 80° C. for 30 minutes. The reaction mixture was concentrated, adjusted to acidic range of pH by adding water and an excessive amount of citric acid, and extracted with ethyl acetate. The ethyl acetate layer was dried over anhydrous sodium sulfate and concentrated to give 16-methanesulfonyloxyhexadecanoic acid (0.960 mg).

After the methanesulfonyloxyhexadecanoic acid thus obtained (0.50 g) and para-nitrophenol (200 mg) were dissolved in N,N-dimethylformamide (DMF, 30 ml), N,N'-dicyclohexylcarbodiimide (295 mg) was added, and the mixture was stirred for 12 hours. The reaction mixture was filtered, and 6-(4'-N-glycyl-spicaminyl-amino)purine hydrochloride (0.55 g) and triethylamine (2.0 ml) were added to the filtrate. The mixture was stirred for 12 hours. After the solvent was removed by distillation, the residue was subjected to chromatography on a silica gel column with eluent systems of chloroform-methanol (from 7:1 to 5:1) to give SPK225 in the yield of 189 mg.

Physicochemical properties of SPK225
(1) Melting point: 161°–162° C.,
(2) Specific rotation $[\alpha]_D^{25}=+10.4°$ (c=0.1, in methanol),
(3) Elementary analysis:

|  | C | H | O | N |
|---|---|---|---|---|
| Calculated (%) | 53.20, | 7.63, | 20.57, | 14.01, |
| Found (%) | 52.96, | 7.38, | 20.46, | 14.30, |

(4) FD mass spectrum (m/z): 700 (M+H)$^+$, $C_{31}H_{53}N_7O_9S$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.80 (26H, m), 2.29 (2H, t, J=7.1 Hz), 3.05 (3H, s), 3.60–3.80 (5H, m), 3.86 (1H, d, J=16.4 Hz), 3.90 (1H, d, J=16.4 Hz), 4.00 (1H, dd, J=2.1, <1 Hz), 4.25 (1H, dd, J=10.4, 10.4 Hz), 4.22 (1H, t, J=7.1 Hz), 5.65 (1H, brs), 8.10 (1H, brs), 8.30 (1H, s).

EXAMPLE 43

Preparation of SPK230

12-Hydroxydodecanoic acid (1 g) was dissolved in methylene chloride (25 ml), and triethylamine (2 ml) was added to the solution. To the mixture, while it was ice-cooled and stirred, was added dropwise 1-propanesulfonyl chloride (1.03 ml). After 1.5 hours of stirring, the reaction mixture was distributed into chloroform and water, and the chloroform layer was dried with anhydrous sodium sulfate and concentrated. The residue thus obtained was subjected to chromatography on a silica gel column with an eluent system of chloroform-hexane (2:1) to give 12-propanesulfonyloxydodecanoic acid (1.49 g). The product (210 mg) was dissolved in N,N-dimethylformamide (DMF). N-Hydroxysuccinimide (75 mg) and N,N'-dicyclohexylcarbodiimide (148 mg) were added, and the mixture was stirred for 12 hours. The precipitates obtained were removed by filtration and the filtrate was concentrated to give the active ester of 12-propanesulfonyloxydodecanoic acid. The active ester was dissolved in DMF, and 6-(4'-N-glycyl-spicaminyl-amino)purine hydrochloride (250 mg) and triethylamine (0.73 ml) were added. The mixture was stirred for 12 hours. The reaction mixture was concentrated, and the residue was subjected to chromatography on a silica gel column with an eluent system of chloroform-methanol (6:1) to give SPK230 in the yield of 480 mg.

Physicochemical properties of SPK230
(1) Melting point: 163°–164° C.,
(2) Specific rotation $[\alpha]_D^{25}=+5.6°$ (c=0.1, in methanol),
(3) Elementary analysis:

|  | C | H | O | N |
|---|---|---|---|---|
| Calculated (%) | 50.64, | 7.18, | 23.26, | 14.26, |
| Found (%) | 50.40, | 7.08, | 23.54, | 14.38, |

(4) FD mass spectrum (m/z): 710 (M+Na)$^+$, $C_{29}H_{49}N_7O_{10}S$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.10 (3H, t, 7.6 Hz), 1.25–1.43 (14H, m), 1.60–1.80 (4H, m), 1.85 (2H, m), 2.30 (2H, t, J=7.1 Hz), 3.17 (2H, t, J=8.3 Hz), 3.65–3.80 (5H, m), 3.87 (1H, d, J=15.0 Hz), 3.90 (1H, d, J=15.0 Hz), 4.01 (1H, d, J=2.0 Hz), 4.14 (1H, dd, J=10.0 Hz), 4.20 (2H, t, J=7.0 Hz), 5.68 (1H, brs), 8.15 (1H, s), 8.29 (1H, s).

EXAMPLE 44

Preparation of SPK232

12-Hydroxydodecanoic acid (1 g) was dissolved in methylene chloride (25 ml), and triethylamine (2 ml) was added to the solution. To the mixture, while it was ice-cooled and stirred, was added dropwise 1-butanesulfonyl chloride (0.72 ml). After 1.5 hours of stirring, the reaction mixture was distributed into chloroform and water, and the chloroform layer was dried with anhydrous sodium sulfate and concentrated. The residue thus obtained was subjected to chromatography on a silica gel column with an eluent system of chloroform-hexane (2:1) to give 12-butanesulfonyloxydodecanoic acid (0.99 g). The product (220 mg) was dissolved in N,N-dimethylformamide (DMF). N-Hydroxysuccinimide (76 mg) and N,N'-dicyclohexylcarbodiimide (149 mg) were added, and the mixture was stirred for 12 hours. The precipitates obtained were removed by filtration and the filtrate was concentrated to give the active ester of 12-butanesulfonyloxydodecanoic acid. The active ester was dissolved in DMF, and 6-(4'-N-glycyl-spicaminyl-amino)purine hydrochloride (251 mg) and triethylamine (0.73 ml) were added. The mixture was stirred for 12 hours. The reaction mixture was concentrated, and the residue was subjected to chromatography on a silica gel column with an eluent system of chloroform-methanol (6:1) to give SPK232 in the yield of 134 mg.

Physicochemical properties of SPK232

(1) Melting point: 161°–162° C., (2) Specific rotation $[\alpha]_D^{25}=+1.2°$ (c=0.1, in methanol), (3) Elementary analysis:

|  | C | H | O | N |
|---|---|---|---|---|
| Calculated (%) | 51.64, | 6.79, | 22.93, | 14.05, |
| Found (%) | 51.50, | 6.88, | 23.15, | 13.80, |

(4) FD mass spectrum (m/z): 698 (M+H)$^+$, $C_{30}H_{47}N_7O_{10}S$ (5) Infrared spectrum (KBr disc): 3400 cm$^{-1}$, 1630 cm$^{-1}$, (6) Proton nuclear magnetic resonance spectrum (500 MHz, in CD$_3$OD) $\delta_H$: 0.97 (1H, t, J=7.3 Hz), 1.20–1.90 (22H, m), 2.28 (2H, t, J=7.3 Hz), 3.20 (2H, t, J=8.0 Hz), 3.60–3.80 (5H, m), 3.85 (1H, d, J=16.4 Hz), 3.89 (1H, d, J=16.4 Hz), 4.00 (1H, dd, J=<1, 2.4 Hz), 4.14 (1H, dd, J=10.7, 10.7 Hz), 4.20 (2H, t, J=6.7 Hz), 5.66 (1H, brs), 8.13 (1H, brs), 8.28 (1H, s).

EXAMPLE 45

Preparation of SPK185

2-Hydroxydodecanoic acid (1 g) dissolved in a 10% methanolic hydrochloric acid solution was stirred at room temperature for 1 hour. The mixture was then concentrated and distributed into chloroform and water, and the chloroform layer was washed with a 1% aqueous sodium hydrogen carbonate solution and water, dried with anhydrous sodium sulfate and concentrated to give the methyl ester of 2-hydroxydodecanoic acid (1.02 g). To the methyl ester of 2-hydroxydodecanoic acid dissolved in pyridine (20 ml) was added butanesulfonyl chloride (0.80 g), and the mixture was stirred for 8 hours. Then, the pyridine was removed by distillation, and the residue was distributed into chloroform and water. The chloroform layer was dried with anhydrous sodium sulfate, concentrated and subjected-to chromatography on a silica gel column with an eluent system of n-hexane-ethyl acetate (50:1) to give the methyl ester of 2-butanesulfonyloxydodecanoic acid (1.21 g).

To the methyl ester, which was dissolved in a mixed solution of ethanol-water (1:1), was added potassium hydroxide (0.6 g), and the mixture was stirred at 80° C. for 30 minutes. The reaction mixture was concentrated, adjusted to acidic range of pH by adding water and an excessive amount of citric acid, and extracted with ethyl acetate. The ethyl acetate layer was dried over anhydrous sodium sulfate and concentrated to give 2-butanesulfonyloxydodecanoic acid (1.16 g).

After the 2-butanesulfonyloxyhexadecanoic acid thus obtained (500 mg) and N-hydroxysuccinimide (171 mg) were dissolved in N,N-dimethylformamide (DMF, 30 ml), N,N'-dicyclohexylcarbodiimide (253 mg) was added, and the mixture was stirred for 12 hours. The reaction mixture was filtered, and 6-(4'-N-glycyl-spicaminyl-amino)purine hydrochloride (569 mg) and triethylamine (1.0 ml) were added to the filtrate. The mixture was stirred for 12 hours. After the solvent was removed by distillation, the residue was subjected to chromatography on a silica gel column with eluent systems of chloroform-methanol (from 7:1 to 5:1) to give SPK185 in the yield of 242 mg.

Physicochemical properties of SPK185

(1) Melting point: 158°–159° C., (2) Elementary analysis:

|  | C | H | O | N |
|---|---|---|---|---|
| Calculated (%) | 52.54, | 7.49, | 21.00, | 14.30, |
| Found (%) | 52.38, | 7.26, | 20.79, | 14.58, |

(3) FD mass spectrum (m/z): 586 (M+H)$^+$, $C_{30}H_{51}N_7O_9S$ (4) Infrared spectrum (KBr disc): 3400 cm$^{-1}$, 1630 cm$^{-1}$, (5) Proton nuclear magnetic resonance spectrum (500 MHz, in CD$_3$OD) $\delta_H$: 0.90 (3H, t, J=7.1 Hz), 0.98 (3H, t, J=7.1 Hz), 1.20–2.00 (22H, m), 3.40 (2H, m), 3.60–4.10 (8H, m), 4.14 (1H, dd, J=10.4, 10.4 Hz), 4.95 (1H, t, J=6.7 Hz), 5.65 (1H, brs), 8.13 (1H, brs), 8.30 (1H, s).

EXAMPLE 46

Preparation of SPK429 and 430

10-Undecynoic acid (0.5 g) was dissolved in tetrahydrofuran (20 ml), and the air within the reactor was purged with argon. After the solution was cooled to −78° C. in a dry ice-acetone bath, a 2.4M solution of n-butyl lithium in hexane (2.7 ml) was added dropwise to the aforementioned solution over a period of 5 minutes. After the mixture was stirred at the same temperature for 15 minutes, trimethylsilyl chloride (0.6 g) was added to the mixture. After 15 minutes, dilute hydrochloric acid was added to the mixture, and the resulting mixture was extracted with ethyl acetate. The organic layer was washed with a brine and dried over anhydrous magnesium sulfate. The mixture was filtered, and the filtrate was concentrated to give a crude product, which was then subjected to chromatography on a silica gel column with eluent systems of n-hexane-ethyl acetate (30:1, 20:1, 10:1, and 5:1) to give 11-trimethylsilyl-10-undecynoic acid (0.44 g).

After the mixture of 11-trimethylsilyl-10-undecynoic acid (0.21 g) and para-nitrophenol (0.11 g) in N,N-dimethylformamide (DMF, 3 ml) was cooled to 0° C., N,N'-dicyclohexylcarbodiimide (0.18 g) was added and the mixture was stirred for 12 hours. The reaction mixture was filtered and concentrated to give the active ester of 11-trimethylsilyl-10-undecynoic acid.

To the solution of 6-(4'-N-glycyl-spicaminyl-amino)purine hydrochloride (400 mg) and triethylamine (1.0 ml) in DMF (15 ml) was added the active ester of 11-trimethylsilyl-10-undecynoic acid (300 mg), and the mixture was stirred for 12 hours. The reaction mixture was concentrated, and the crude product was subjected to chromatography on a silica gel column with eluent systems of chloroform-methanol (5:1 to 4:1) to give SPK429 in the yield of 37 mg.

Physicochemical properties of SPK429

(1) Melting point: 170°–172° C., (2) Specific rotation $[\alpha]_D^{25}=+5.6°$ (c=0.1, in methanol), (3) Elementary analysis:

|  | C | H | O | N |
|---|---|---|---|---|
| Calculated (%) | 54.26, | 7.32, | 18.07, | 15.82, |
| Found (%) | 54.49, | 7.12, | 17.90, | 16.10, |

(4) FD mass spectrum (m/z): 620 (M+H)$^+$, $C_{28}H_{45}N_7O_7Si$ (5) Infrared spectrum (KBr disc): 3300 cm$^{-1}$, 2100 cm$^{-1}$, 1630 cm$^{-1}$, (6) Proton nuclear magnetic resonance spectrum (500 MHz, in CDCl$_3$-CD$_3$OD) $\delta_H$: 0.11 (9H, s), 1.30–1.70 (12H, m), 2.20 (2H, t, J=7.1 Hz), 2.30 (2H, t, J=7.1 Hz), 3.60–3.80 (5H, m), 3.86 (1H, d, J=16.4 Hz), 3.90 (1H, d, J=16.4 Hz), 4.02 (1H, dd, J=2.1, <1 Hz), 4.16 (1H, dd, J=10.1, 10.1 Hz), 5.62 (1H, brs), 8.10 (1H, brs), 8.30 (1H, s).

At the same time, 11-trimethylsilyl-10-undecynoic acid (0.23 g) was dissolved in ethyl acetate (5 ml), and 10% palladium-carbon (10 mg) was added to the solution. After the air within the reactor was purged with hydrogen, the mixture was stirred at room temperature for 12 hours. Then, the mixture was filtered, and the filtrate was concentrated to give 11-trimethylsilylundecanoic acid (0.21 g).

After the mixture of 11-trimethylsilylundecanoic acid (0.21 g) and para-nitrophenol (0.12 g) in N,N-dimethylformamide (DMF, 3 ml) was cooled to 0° C., N,N'-dicyclohexylcarbodiimide (0.18 g) was added, and the mixture was stirred for 12 hours. The reaction mixture was filtered and concentrated to give the active ester of 11-trimethylsilylundecanoic acid.

To the solution of 6-(4'-N-glycyl-spicaminyl-amino) purine hydrochloride (150 mg) and triethylamine (0.5 ml) in DMF (15 ml) was added the active ester of 11-trimethylsilylundecanoic acid (148 mg), and the mixture was stirred for 12 hours. The reaction mixture was concentrated, and the crude product was subjected to chromatography on a silica gel column with eluent systems of chloroform-methanol (5:1 to 4:1) to give SPK430 in the yield of 40 mg.

Physicochemical properties of SPK430
(1) Melting point: 176°–177° C.,
(2) Specific rotation $[\alpha]_D^{25}$=+17.2° (c=0.1, in methanol),
(3) Elementary analysis:

|  | C | H | O | N |
| --- | --- | --- | --- | --- |
| Calculated (%) | 53.91, | 7.92, | 17.95, | 15.72, |
| Found (%) | 53.80, | 8.12, | 18.22, | 15.44, |

(4) FD mass spectrum (m/z): 624 (M+H)$^+$, $C_{28}H_{49}N_7O_7Si$
(5) Infrared spectrum (KBr disc): 3400 cm$^{-1}$, 1630 cm$^{-1}$,
(6) Proton nuclear magnetic resonance spectrum (500 MHz, in CDCl$_3$-CD$_3$OD) $\delta_H$: −0.04 (9H, s), 0.48 (2H, brt), 1.24–1.35 (14H, m), 1.62 (2H, t, J=7.3 Hz), 2.26 (2H, t, J=7.3 Hz), 3.65–3.80 (5H, m), 3.86 (1H, d, J=16.0 Hz), 3.89 (1H, d, J=16.0 Hz), 4.00 (1H, dd, J=2.0, <1 Hz), 4.13 (1H, dd, J=10.3, 10.3 Hz), 5.64 (1H, m), 8.11 (1H, s), 8.28 (1H, s).

EXAMPLE 47

Preparation of SPK123

To a solution of NaOH (5.03 g) in water (200 ml) was suspended oleic acid (4.96 g), and the mixture to which ice had been added, was stirred at 5° C. A solution of potassium permanganate (4 g) in water (500 ml) was added, and the mixture was stirred for 5 minutes. Then, aqueous sulfurous acid was added until the mixture turned white, and the resulting precipitates were collected by filtration. The precipitates were washed with water and eluted with a mixture of chloroform-methanol (1:1), and the eluate was concentrated to give 9,10-dihydroxyoctadecanoic acid (4.69 g). To the suspension of 9,10-dihydroxyoctadecanoic acid in acetone was added conc. sulfuric acid (0.1 ml), and the mixture was stirred for 8 hours. After acetone was removed by distillation and water was added, the mixture was extracted with ethyl acetate. The ethyl acetate layer was dried over anhydrous sodium sulfate to give an acetonide (4.70 g). To the acetonide (3.70 g) were added para-nitrophenol (1.44 g) and N,N'-dicyclohexylcarbodiimide (3.21 g), and the mixture was stirred in N,N-dimethylformamide (DMF) for 12 hours. After precipitates produced were removed by filtration and the solvent (DMF) was removed by distillation, the residue was subjected to chromatography on a silica gel column with an eluent system of n-hexane-ethyl acetate (50:1) to give the active ester of 9,10-dihydroxyoctadecanoic acid 9,10-acetonide (3.05 g). The active ester was dissolved in DMF together with 6-(4'-N-glycyl-spicaminyl-amino)purine hydrochloride (400 mg), and after triethylamine (2.0 ml) was added, the mixture was stirred for 12 hours. The reaction mixture was concentrated, and the residue was subjected to chromatography on a silica gel column with eluent systems of chloroform-methanol (7:1 to 5:1) to give SPK123 in the yield of 113.9 mg.

Physicochemical properties of SPK123
(1) Melting point: 226°–227° C.,
(2) Elementary analysis:

|  | C | H | O | N |
| --- | --- | --- | --- | --- |
| Calculated (%) | 58.23, | 8.24, | 19.95, | 13.58, |
| Found (%) | 58.40, | 8.41, | 19.79, | 13.40, |

(3) FD mass spectrum (m/z): 722 (M+H)$^+$, $C_{35}H_{59}N_7O_9$
(4) Infrared spectrum (KBr disc): 3400 cm$^{-1}$, 1630 cm$^{-1}$,
(5) Proton nuclear magnetic resonance spectrum (500 MHz, in CD$_3$OD) $\delta_H$: 0.90 (3H, t, J=7.1 Hz), 1.20–1.70 (26H, m), 1.38 (6H, s), 2.28 (2H, t, J=7.0 Hz), 3.60–3.80 (5H, m), 3.86 (1H, d, J=15.0 Hz), 3.90 (1H, d, J=15.0 Hz), 4.00 (1H, dd, J=2.1, <1 Hz), 4.04 (2H, m), 4.14 (1H, dd, J=10.3, 10.3 Hz), 5.69 (1H, brs), 8.16 (1H, s), 8.31 (1H, s).

EXAMPLE 48

Preparation of SPK102

12-Hydroxystearic acid (2 g) dissolved in a 10% methanolic hydrochloric acid solution was stirred at room temperature for 2 hours. The mixture was then concentrated and distributed into chloroform and water, and the chloroform layer was washed with a 1% aqueous sodium hydrogen carbonate solution and water, dried with anhydrous sodium sulfate and concentrated to give the methyl ester of 12-hydroxystearic acid (2.0 g). To the methyl ester of 2-hydroxystearic acid (2.0 g) dissolved in methylene chloride (50 ml) were added Celite (4 g) and pyridinium chlorochromate (6 g), and the mixture was stirred at room temperature for 24 hours. Precipitates produced were removed by filtration. The filtrate mixed with silica gel (10 g) was concentrated and eluted with n-hexane-ethyl acetate (5:1) to give the methyl ester of 12-oxo-stearic acid (1.8 g). Then, the methyl ester of 12-oxo-stearic acid (1.8 g) was suspended into the mixed solvent of ethanol-water (1:1), and the potassium hydroxide (1.7 g) was dissolved in the suspension. The reaction mixture was heated to a temperature of 70° C. and stirred for 30 minutes. The reaction mixture was then cooled, adjusted to acidic range of pH by adding water and an excessive amount of citric acid and extracted with ethyl acetate. The ethyl acetate layer was dried over anhydrous sodium sulfate and concentrated to give 12-oxostearic acid (1.6 g). After the 12-oxostearic acid (500 mg) was dissolved in N,N-dimethylformamide (DMF), para-nitrophenol (231 mg) and N,N'-dicyclohexylcarbodiimide (343 mg) were added, and the mixture was stirred for 12 hours. The reaction mixture was filtered, and the solvent was removed by distillation to give the active ester of 12-oxostearic acid. The active ester (438 mg) was dissolved in DMF, 6-(4'-N-glycyl-spicaminyl-amino)purine hydrochloride (400 mg) and triethylamine (2.0 ml) were added to the solution. The mixture was stirred for 12 hours. After the solvent was removed by distillation, the residue was subjected to chromatography on a silica gel column with eluent systems of chloroform-methanol (from 7:1 to 5:1) to give SPK102 in the yield of 143 mg.

Physicochemical properties of SPK102

(1) Melting point: 225°–227° C.,
(2) Specific rotation $[\alpha]_D^{26}$=+13.3° (c=0.1, in methanol),
(3) Elementary analysis:

|  | C | H | O | N |
|---|---|---|---|---|
| Calculated (%) | 57.90, | 8.05, | 19.28, | 14.77, |
| Found (%) | 57.74, | 8.12, | 19.46, | 14.68, |

(4) FD mass spectrum (m/z): 686 (M+Na)$^+$, $C_{32}H_{53}N_7O_8$
(5) Infrared spectrum (KBr disc): 3400 cm$^{-1}$, 1710 cm$^{-1}$, 1630 cm$^{-1}$,
(6) Proton nuclear magnetic resonance spectrum (500 MHz, in CDCl$_3$-CD$_3$OD) $\delta_H$: 0.90 (3H, t, J=7.1 Hz), 1.20–1.70 (24H, m), 2.28 (2H, t, J=7.0 Hz), 2.44 (4H, t, J=7.0 Hz), 3.60–3.80 (5H, m), 3.87 (1H, d, J=15.6 Hz), 3.90 (1H, d, J=15.6 Hz), 4.00 (1H, dd, J=2.1, <1 Hz), 4.14 (1H, dd, J=10.3, 10.3 Hz), 5.67 (1H, brs), 8.16 (1H, brs), 8.32 (1H, s).

EXAMPLE 49

Preparation of SPK251

To 11-methyldodecanoic acid (400 mg) and para-nitrophenol (260 mg) dissolved in N,N-dimethylformamide (DMF, 30 ml) was added N,N'-dicyclohexylcarbodiimide (385 mg), and the mixture was stirred for 12 hours. The reaction mixture was filtered and concentrated to give the active ester of 10-methylundecanoic acid. To the active ester (620 mg), after having been dissolved in DMF, were added 6-(4'-N-glycyl-spicaminyl-amino)purine hydrochloride (710 mg) and triethylamine (2.0 ml), and the mixture was stirred for 12 hours. The solvent was removed by distillation, and the residue was subjected to chromatography on a silica gel column with eluent systems of chloroform-methanol (from 7:1 to 5:1) to give SPK251 in the yield of 236 mg.

Physicochemical properties of SPK251

(1) Melting point: 170°–171° C.,
(2) Specific rotation $[\alpha]_D^{25}$=+2.8° (c=0.1, in methanol),
(3) Elementary analysis:

|  | C | H | O | N |
|---|---|---|---|---|
| Calculated (%) | 55.94, | 7.82, | 19.32, | 16.91, |
| Found (%) | 56.18, | 8.09, | 19.05, | 16.68, |

(4) FD mass spectrum (m/z): 580 (M+H)$^+$, $C_{27}H_{45}N_7O_7$
(5) Infrared spectrum (KBr disc): 3300 cm$^{-1}$, 1620 cm$^{-1}$,
(6) Proton nuclear magnetic resonance spectrum (500 MHz, in CDCl$_3$-CD$_3$OD) $\delta_H$: 0.89 (6H, d, J=6.4 Hz), 1.10–1.70 (17H, m), 2.28 (2H, t, J=7.0 Hz), 3.65–3.80 (5H, m), 3.85 (1H, d, J=15.6 Hz), 4.02 (1H, d, J=15.6 Hz), 4.01 (1H, dd, J=2.1, <1 Hz), 4.15 (1H, dd, J=10.3, 10.3 Hz), 5.68 (1H, brs), 8.32 (1H, s), 8.10 (1H, s).

EXAMPLE 50

Preparation of SPK282

To trans-2-decenal (5.0 g) dissolved in methylene chloride (80 ml) was added (carbomethoxymethylene)-triphenylphosphorane (11.99 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-dodecadienoic acid (6.1 g). Potassium hydroxide (8.1 g) was dissolved in a mixed solvent of ethanol-water (1:1) (100 ml). The methyl ester of trans, trans-2,4-dodecadienoic acid (6.1 g) was added to the mixture, and the resulting mixture was stirred at 60° C. for 40 minutes. After the reaction mixture was cooled, it was adjusted to the weak acidic range of pH with citric acid and extracted with ethyl acetate. The ethyl acetate layer was dried over anhydrous sodium sulfate and concentrated to give trans,trans-2,4-dodecadienoic acid (5.4 g). To trans, trans-2,4-dodecadienoic acid dissolved in N,N-dimethylformamide (DMF, 50 ml) were added para-nitrophenol (3.8 g) and N,N'-dicyclohexylcarbodiimide (5.8 g), and the mixture was stirred for 12 hours. After precipitates obtained were removed by filtration and the solvent (DMF) was removed by distillation, the residue was subjected to chromatography on a silica gel column with eluent systems of n-hexane-ethyl acetate (from 200:1 to 50:1) to give the active ester of trans,trans-2,4-dodecadienoic acid (3.4 g). To the active ester (800 mg) dissolved in DMF (30 ml) were added 6-(4'-N-glycyl-spicaminyl-amino)purine hydrochloride (800 mg) and triethylamine (2.0 ml). The mixture was stirred for 12 hours. After the solvent was removed by distillation, the residue was subjected to chromatography on a silica gel column with eluent systems of chloroform-methanol (from 7:1 to 5:1) to give SPK282 in the yield of 310 mg.

Physicochemical properties of SPK282

(1) Melting point: 168°–169° C.,
(2) Specific rotation $[\alpha]_D^{25}$=+7.6° (c=0.1, in methanol),
(3) Elementary analysis:

|  | C | H | O | N |
|---|---|---|---|---|
| Calculated (%) | 55.60, | 7.00, | 19.94, | 17.46, |
| Found (%) | 55.81, | 6.83, | 19.65, | 17.71, |

(4) FD mass spectrum (m/z): 562 (M+H)$^+$, $C_{26}H_{39}N_7O_7$
(5) Infrared spectrum (KBr disc): 3250 cm$^{-1}$, 1650 cm$^{-1}$, 1620 cm$^{-1}$,
(6) Proton nuclear magnetic resonance spectrum (500 MHz, in CD$_3$OD) $\delta_H$: 0.90 (3H, t, J=7.3 Hz), 1.20–1.50 (10H, m), 2.18 (2H, dt, J=7.3, 7.3 Hz), 3.60–3.80 (5H, m), 3.95 (1H, d, J=16.3 Hz), 3.98 (1H, d, J=16.3 Hz), 4.00 (1H, dd, J=<1, 2.9 Hz), 4.15 (1H, dd, J=10.8, 10.8 Hz), 5.68 (1H, brs), 6.00 (1H, d, J=15.7 Hz), 6.13 (1H, d, J=7.3, 15.7 Hz), 6.22 (1H, dd, J=10.0, 15.7 Hz), 7.17 (1H, dd, J=10.0, 15.7 Hz), 8.15 (1H, s), 8.30 (1H, s).

EXAMPLE 51

Preparation of SPK281

To trans-2-undecenal (5.0 g) dissolved in methylene chloride (80 ml) was added (carbomethoxymethylene)-triphenylphosphorane (9.9 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-tridecadienoic acid (5.2 g). Potassium hydroxide (6.5 g) was dissolved in a mixed solvent of ethanol-water (1:1) (100 ml). The methyl ester of trans, trans-2,4-tridecadienoic acid (5.2 g) was added to the mixture, and the resulting mixture was stirred at 60° C. for 40 minutes. After the reaction mixture was cooled, it was adjusted to the weak acidic range of pH with citric acid and extracted with ethyl acetate. The ethyl acetate layer was dried over anhydrous sodium sulfate and concentrated to give trans,trans-2,4-tridecadienoic acid (4.4 g). To trans, trans-2,4-tridecadienoic acid dissolved in N,N-dimethylformamide (DMF, 50 ml) were added para-nitrophenol (3.0 g) and N,N'-dicyclohexylcarbodiimide (4.4 g), and the mixture was stirred for 12 hours. After precipitates obtained were removed by filtration and the solvent (DMF) was removed by distillation, the residue was subjected to chromatography on a silica gel column with eluent systems of n-hexane-ethyl acetate (from 200:1 to 50:1) to give the active ester of trans,trans-2,4-tridecadienoic acid (2.4 g). To the active ester (880 mg) dissolved in DMF (30 ml) were added 6-(4'-N-glycyl-spicaminyl-amino)purine hydrochloride (800 mg) and triethylamine (2.0 ml). The mixture was stirred for 12 hours. After the solvent was removed by distillation, the residue was subjected to chromatography on a silica gel column with eluent systems of chloroform-methanol (from 7:1 to 5:1) to give SPK281 in the yield of 380 mg.

Physicochemical properties of SPK281

(1) Melting point: 177°–179° C.,
(2) Specific rotation $[\alpha]_D^{25}=+6.8°$ (c=0.1, in methanol),
(3) Elementary analysis:

|  | C | H | O | N |
|---|---|---|---|---|
| Calculated (%) | 56.33, | 7.18, | 19.46, | 17.03, |
| Found (%) | 56.60, | 6.91, | 19.22, | 17.27, |

(4) FD mass spectrum (m/z): 598 (M+Na)$^+$, $C_{27}H_{41}N_7O_7$
(5) Infrared spectrum (KBr disc): 3250 cm$^{-1}$, 1650 cm$^{-1}$, 1620 cm$^{-1}$,
(6) Proton nuclear magnetic resonance spectrum (500 MHz, in CD$_3$OD) $\delta_H$: 0.90 (3H, t, J=7.3 Hz), 1.20–1.50 (12H, m), 2.18 (2H, dt, J=7.3, 7.3 Hz), 3.60–3.80 (5H, m), 3.95 (1H, d, J=16.3 Hz), 3.98 (1H, d, J=16.3 Hz), 4.00 (1H, dd, J=<1, 2.9 Hz), 4.15 (1H, dd, J=10.8, 10.8 Hz), 5.68 (1H, brs), 6.00 (1H, d, J=15.7 Hz), 6.13 (1H, d, J=7.3, 15.7 Hz), 6.22 (1H, dd, J=10.0, 15.7 Hz), 7.17 (1H, dd, J=10.0, 15.7 Hz), 8.15 (1H, s), 8.30 (1H, s).

EXAMPLE 52

Preparation of SPK241

To trans-2-dodecenal (4.5 g) dissolved in methylene chloride (80 ml) was added (carbomethoxymethylene)-triphenylphosphorane (8.3 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-tetradecadienoic acid (5.4 g). Potassium hydroxide (6.5 g) was dissolved in a mixed solvent of ethanol-water (1:1) (100 ml). The methyl ester of trans,trans-2,4-tetradecadienoic acid (5.4 g) was added to the mixture, and the resulting mixture was stirred at 60° C. for 40 minutes. After the reaction mixture was cooled, it was adjusted to the weak acidic range of pH with citric acid and extracted with ethyl acetate. The ethyl acetate layer was dried over anhydrous sodium sulfate and concentrated to give trans,trans-2,4-tetradecadienoic acid (4.4 g). Hereafter, the title compound can be synthesized by the two methods described below.

In the first method, trans,trans-b 2,4-tetradecadienoic acid (4.3 g) is first dissolved in N,N-dimethylformamide (DMF, 50 ml). Para-nitrophenol (2.67 g) and N,N'-dicyclohexylcarbodiimide (3.9 g) were added to trans,trans-2,4-tetradecadienoic acid solution, and the mixture was stirred for 12 hours. After precipitates produced were removed by filtration and the solvent (DMF) was removed by distillation, the residue was subjected to chromatography on a silica gel column with eluent systems of n-hexane-ethyl acetate (from 200:1 to 50:1) to give the active ester of trans,trans-2,4-tetradecadienoic acid (5.1 g). To the active ester (500 mg) dissolved in DMF (30 ml) were added 6-(4'-N-glycyl-spicaminyl-amino)purine hydrochloride (556 mg) and triethylamine (1.2 ml). The mixture was stirred for 12 hours. After the solvent was removed by distillation, the residue was subjected to chromatography on a silica gel column with eluent systems of chloroform-methanol (from 7:1 to 5:1) to give SPK241 in the yield of 398 mg.

In the second method, trans,trans-2,4-tetradecadienoic acid (99.6 g) was dissolved in thionyl chloride (87 ml), and the mixture was stirred at room temperature. The excessive thionyl chloride was removed by distillation to give trans,trans-2,4-tetradecadienoic acid chloride (102.0 g). To glycine (66.8 g) dissolved in an aqueous 2N sodium hydroxide solution (540 ml) were added at the same time trans,trans-2,4-tetradecadienoic acid chloride (102.0 g) and 2N sodium hydroxide (270 ml) with 1/10 portions at a 3 minute interval. After the addition was completed, the mixture was warmed to room temperature, stirred for 15 minutes and acidified with concentrated hydrochloric acid (140 ml) under ice-cooling. Precipitates thus produced were collected by filtration and desiccated to give trans,trans-2,4-tetradecadienoyl glycine (75.0 g). To the solution of trans,trans-2,4-tetradecadienoyl glycine (4.7 g) and 6-6-(spicaminyl-amino)purine (5.1 g) in N,N-dimethylformamide (DMF, 60 ml) was added N-hydroxysuccinimide (2.1 g), and the mixture was ice-cooled. 1-Ethyl-3-(3-dimethylaminopropyl)carbodiimide hydrochloride (3.4 g) dissolved in DMF (100 ml) was added dropwise to the mixture. After the addition was completed, the mixture was heated to room temperature and stirred for 12 hours. Water (500 ml) was added to the reaction mixture, and precipitates produced were collected by filtration and desiccated. Sodium methoxide (3.1 g) was added to a suspension of the precipitates in methanol (100 ml), and the mixture was stirred at room temperature, then ice-cooled and acidified by adding dropwise thereto a 10% methanolic hydrochloric acid solution. Precipitates produced were filtered, dried and subjected to chromatography on a silica gel column with eluent systems of chloroform-methanol (from 7:1 to 5:1) to give SPK241 in the yield of 5.00 g.

Physicochemical properties of SPK241

(1) Melting point: 182°–183° C.,
(2) Specific rotation $[\alpha]_D^{25}=0°$ (c=0.1, in methanol),
(3) Elementary analysis:

|  | C | H | O | N |
|---|---|---|---|---|
| Calculated (%) | 57.03, | 7.35, | 18.99, | 16.63, |
| Found (%) | 56.78, | 7.59, | 19.21, | 16.42, |

(4) FD mass spectrum (m/z): 590 (M+H)$^+$, $C_{28}H_{43}N_7O_7$
(5) Infrared spectrum (KBr disc): 3250 cm$^{-1}$, 1650 cm$^{-1}$, 1620 cm$^{-1}$,
(6) Proton nuclear magnetic resonance spectrum (500 MHz, in CD$_3$OD) $\delta_H$: 0.89 (3H, t, J=7.3 Hz), 1.20–1.50 (14H, m), 2.18 (2H, dt, J=7.3, 7.3 Hz), 3.6–3.8 (5H, m), 3.95 (1H, d, J=16.3 Hz), 3.98 (1H, d, J=16.3 Hz), 4.00 (1H, dd, J=<1, 2.9 Hz), 4.15 (1H, dd, J=10.8, 10.8 Hz), 5.66 (1H, brs), 5.98 (1H, d, J=15.7 Hz), 6.12 (1H, dt, J=7.3, 15.7 Hz), 6.22 (1H, dd, J=10.0, 15.7 Hz), 7.17 (1H, dd, J=10.0, 15.7 Hz), 8.15 (1H, s), 8.30 (1H, s).

EXAMPLE 53

Preparation of SPK285

To undecyl aldehyde (5.0 g) dissolved in methylene chloride was added (carbomethoxymethylene)-triphenylphosphorane (14.7 g), and the mixture was stirred for 2 hours. The reaction mixture was concentrated and subjected to chromatography on a silica gel column with eluent systems of n-hexane-ethyl acetate (from 100:1 to 20:1) to give the methyl ester of trans-2-tridecenoic acid (55.2 g). To the methyl ester dissolved in tetrahydrofuran was added lithium aluminium hydride (0.9 g) under ice-cooling, and the mixture was stirred for 1 hour. The reaction mixture was distributed into ethyl acetate and water, and the ethyl acetate layer was dried, concentrated and subjected to chromatography on a silica gel column with an eluent system of n-hexane-ethyl acetate (50:1) to give trans-2-tridecenol (3.2 g). To the solution of the trans-2-tridecenol in methylene chloride were added pyridinium chlorochromate (3.2 g) and Celite (5.0 g), and the mixture was stirred. The reaction mixture was filtered and concentrated to give trans-2-tridecenal (1.7 g).

To the trans-2-tridecenal (1.7 g) dissolved in methylene chloride (80 ml) was added (carbomethoxymethylene)triphenyl phosphorane (4.0 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-pentadecadienoic acid (2.1 g). Potassium hydroxide (2.0 g) was dissolved in a mixed solvent of ethanol-water (1:1), and the methyl ester of trans,trans-2,4-pentadecadienoic acid (2.1 g). After the mixture was stirred at 60° C. for 40 minutes, it was cooled, adjusted to a weak acidic range of pH with citric acid and extracted with ethyl acetate. The ethyl acetate layer was dried over anhydrous sodium sulfate and concentrated to give trans,trans-2,4-pentadecadienoic acid (1.9 g). The product was dissolved in N,N-dimethylformamide (DMF, 50 ml), and para-nitrophenol (1.2 g) and N,N'-dicyclohexylcarbodiimide (1.7 g) were added. The mixture was stirred for 12 hours. After the reaction, precipitates produced were removed by filtration, DMF was removed by distillation, and the residue was subjected to chromatography on a silica gel column with eluent systems of n-hexane-ethyl acetate (from 200:1 to 50:1) to give the active ester of trans,trans-2,4-pentadecadienoic acid (1.3 g). To the active ester (600 mg) dissolved in DMF (30 ml) were added 6-(4'-N-glycyl-spicaminyl-amino)purine hydrochloride (750 mg) and triethylamine (1.2 ml). The mixture was stirred for 12 hours. After the solvent was removed by distillation, the residue was subjected to chromatography on a silica gel column with eluent systems of chloroform-methanol (from 7:1 to 5:1) to give SPK285 in the yield of 530 mg.

Physicochemical properties of SPK285

(1) Melting point: 188°–189° C.,
(2) Specific rotation $[\alpha]_D^{25}$=+2.1° (c=0.1, in methanol),
(3) Elementary analysis:

|  | C | H | O | N |
|---|---|---|---|---|
| Calculated (%) | 57.70, | 7.51, | 18.55, | 16.24, |
| Found (%) | 57.94, | 7.70, | 18.38, | 15.98, |

(4) FD mass spectrum (m/z): 604 (M+H)$^+$, $C_{29}H_{45}N_7O_7$
(5) Infrared spectrum (KBr disc): 3300 cm$^{-1}$, 1655 cm$^{-1}$, 1620 cm$^{-1}$,
(6) Proton nuclear magnetic resonance spectrum (500 MHz, in CD$_3$OD) $\delta_H$: 0.90 (3H, t, J=7.3 Hz), 1.20–1.50 (16H, m), 2.18 (2H, dt, J=7.3, 7.3 Hz), 3.60–3.80 (5H, m), 3.95 (1H, d, J=16.1 Hz), 3.98 (1H, d, J=16.1 Hz), 4.02 (1H, dd, J=<1, 2.9 Hz), 4.16 (1H, dd, J=10.8, 10.8 Hz), 5.68 (1H, brs), 6.00 (1H, d, J=15.7 Hz), 6.13 (1H, d, J=7.3, 15.7 Hz), 6.22 (1H, dd, J=10.3, 15.7 Hz), 7.17 (1H, dd, J=10.3, 15.7 Hz), 8.15 (1H, s), 8.30 (1H, s).

EXAMPLE 54

Preparation of SPK283

To dodecyl aldehyde (5.0 g) dissolved in methylene chloride was added (carbomethoxymethylene)-triphenylphosphorane (9.1 g), and the mixture was stirred for 2 hours. The reaction mixture was concentrated and subjected to chromatography on a silica gel column with eluent systems of n-hexane-ethyl acetate (from 100:1 to 20:1) to give the methyl ester of trans-2-tetradecenoic acid (5.2 g). To the methyl ester dissolved in tetrahydrofuran was added lithium aluminium hydride (0.9 g) under ice-cooling, and the mixture was stirred for 1 hour. The reaction mixture was distributed into ethyl acetate and water, and the ethyl acetate layer was dried, concentrated and subjected to chromatography on a silica gel column with an eluent system of n-hexane-ethyl acetate (50:1) to give trans-2-tetradecenol (3.2 g). To the solution of the trans-2-tridecenol in methylene chloride were added pyridinium chlorochromate (3.5 g) and Celite (5.0 g), and the mixture was stirred. The reaction mixture was filtered and concentrated to give trans-2-tetradecenal (2.3 g).

To the trans-2-tetradecenal (2.3 g) dissolved in methylene chloride (80 ml) was added (carbomethoxymethylene)triphenylphosphorane (4.4 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-hexadecadienoic acid (2.2 g). Potassium hydroxide (2.8 g) was dissolved in a mixed solvent of ethanol-water (1:1), and the methyl ester of trans,trans-2,4-hexadecadienoic acid (2.2 g). After the mixture was stirred at 60° C. for 40 minutes, it was cooled, adjusted to a weak acidic range of pH with citric acid and extracted with ethyl acetate. The ethyl acetate layer was dried over anhydrous sodium sulfate and concentrated to give trans,trans-2,4-hexadecadienoic acid (2.0 g). The product was dissolved in N,N-dimethylformamide (DMF, 50 ml), and para-nitrophenol (1.1 g) and N,N'-dicyclohexylcarbodiimide (1.6 g) were added. The mixture was stirred for 12 hours. After the reaction, precipitates produced were removed by filtration, DMF was removed by distillation, and the residue was subjected to chromatography on a silica gel column with eluent systems of n-hexane-ethyl acetate (from 200:1 to 50:1) to give the active ester of trans,trans-2,4-hexadecadienoic acid (0.8 g). To the active ester (340 mg) dissolved in DMF (30 ml) were added 6-(4'-N-glycyl-spicaminyl-amino)purine hydrochloride (500 mg) and triethylamine (1.2 ml). The mixture was stirred for 12 hours. After the solvent was removed by distillation, the residue was subjected to chromatography on a silica gel column with eluent systems of chloroform-methanol (from 7:1 to 5:1) to give SPK283 in the yield of 270 mg.

Physicochemical properties of SPK283
(1) Melting point: 188°–189° C.,
(2) Specific rotation $[\alpha]_D^{25}=+4°$ (c=0.1, in methanol),
(3) Elementary analysis:

|  | C | H | O | N |
|---|---|---|---|---|
| Calculated (%) | 58.33, | 7.67, | 18.13, | 15.87, |
| Found (%) | 58.06, | 7.89, | 17.98, | 16.07, |

(4) FD mass spectrum (m/z): 618 (M+H)$^+$, $C_{30}H_{47}N_7O_7$
(5) infrared spectrum (KBr disc): 3300 cm$^{-1}$, 1655 cm$^{-1}$, 1620 cm$^{-1}$,
(6) proton nuclear magnetic resonance spectrum (500 MHz, in CD$_3$OD) $\delta_H$: 0.90 (3H, t, J=7.3 Hz), 1.20–1.50 (18H, m), 2.18 (2H, dt, J=7.3, 7.3 Hz), 3.60–3.80 (5H, m), 3.95 (1H, d, J=16.3 Hz), 3.98 (1H, d, J=16.3 Hz), 4.00 (1H, dd, J=<1, 2.9 Hz), 4.15 (1H, dd, J=10.8, 10.8 Hz), 5.68 (1H, brs), 6.00 (1H, d, J=15.7 Hz), 6.13 (1H, d, J=7.3, 15.7 Hz), 6.22 (1H, dd, J=10.0, 15.7 Hz), 7.17 (1H, dd, J=10.0, 15.7 Hz), 8.15 (1H, s), 8.30 (1H, s).

EXAMPLE 55

Preparation of SPM10

To N,N-dimethylformamide (DMF, 30 ml) were dissolved tetradecanoic acid (1 g) and para-nitrophenol (0.60 g). N,N'-Dicyclohexylcarbodiimide (0.90 g) was added to the solution, and the mixture was stirred for 12 hours. The reaction mixture was filtered and concentrated to give an active ester of tetradecanoic acid. To the active ester (500 mg) dissolved in DMF were added 6-(4'-N-glycyl-spicaminyl-amino)purine hydrochloride (549 mg) and triethylamine (2.0 ml), and the mixture was stirred for 12 hours. The solvent was removed by distillation, and the residue was purified by chromatography on a silica gel column with eluent systems of chloroform-methanol (from 7:1 to 5:1) to give SPM10 in the yield of 290 mg.

Physicochemical properties of SPM10
(1) Melting point: 210°–212° C.,
(2) Specific rotation $[\alpha]_D^{25}=+4.8°$ (c=0.1, in methanol),
(3) Elementary analysis:

|  | C | H | O | N |
|---|---|---|---|---|
| Calculated (%) | 56.64, | 7.98, | 18.86, | 16.51, |
| Found (%) | 56.91, | 8.21, | 18.64, | 16.24, |

(4) FD mass spectrum (m/z): 594 (M+H)$^+$, $C_{28}H_{47}O_7N_7$
(5) Infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 0.90 (3H, t, J=7.1 Hz), 1.20–1.40 (20H, m), 1.60–1.70 (2H, m), 2.28 (2H, t, J=7.0 Hz), 3.60–3.80 (5H, m), 3.87 (1H, d, J=16.4 Hz), 3.89 (1H, d, J=16.4 Hz), 4.05 (1H, dd, J=2.1 Hz, <1 Hz), 4.14 (1H, dd, J=10.1, 10.1 Hz), 5.58 (1H, brs), 8.10 (1H, brs), 8.31 (1H, s).

EXAMPLE 56

Preparation of SPK148

To palmitoleic acid [CH$_3$(CH$_2$)$_5$CH=CH(CH$_2$)$_7$COOH]

(Z)

(500 mg) dissolved in DMF were added N-hydroxysuccinimide (226 mg) and N,N'-dicyclohexylcarbodiimide (406 mg) was added, and the mixture was stirred for 12 hours. The reaction mixture was filtered, and triethylamine (10 ml) and 6-(4'-N-glycyl-spicaminyl-amino)purine hydrochloride (250 mg) were added to the filtrate. The mixture was stirred for 12 hours. The reaction mixture was concentrated and the residue was purified by chromatography on a silica gel column with eluent systems of chloroform-methanol (from 7:1 to 5:1) to give SPK148 in the yield of 133 mg.

Physicochemical properties of SPK148
(1) Melting point: 174°–175° C.,
(2) Specific rotation $[\alpha]_D^{25}=+18°$ (c=0.1, in methanol),
(3) Elementary analysis:

|  | C | H | O | N |
|---|---|---|---|---|
| Calculated (%) | 58.14, | 7.97, | 18.07, | 15.82, |
| Found (%) | 57.88, | 8.20, | 17.86, | 16.06, |

(4) FD mass spectrum (m/z): 621 (M+H)$^+$, $C_{30}H_{49}O_7N_7$
(5) Infrared spectrum (KBr disc): 3000 cm$^{-1}$, 1630 cm$^{-1}$,
(6) Proton nuclear magnetic resonance spectrum (500 MHz, in CD$_3$OD) $\delta_H$: 0.90 (3H, t, J=7.0 Hz), 1.25–1.70 (20H, m), 2.05 (4H, m), 2.28 (2H, t, J=7.1 Hz), 3.60–3.80 (5H, m), 3.86 (1H, d, J=16.1 Hz), 3.89 (1H, d, J=16.1 Hz), 4.01 (1H, dd, J=2.1 Hz, <1 Hz), 4.14 (1H, dd, J=10.1, 10.1 Hz), 5.34 (2H, m), 5.68 (1H, brs), 8.15 (1H, brs), 8.30 (1H, s).

EXAMPLE 57

Preparation of SPK176

To N,N-dimethylformamide (DMF, 30 ml) were dissolved 10-undecenoic acid (1.0 g) and para-nitrophenol (0.83 g). N,N'-Dicyclohexylcarbodiimide (1.23 g) was added to the solution, and the mixture was stirred for 12 hours. The reaction mixture was filtered and concentrated to give an active ester of 10-undecenoic acid. To the active ester (500 mg) dissolved in DMF were added 6-(4'-N-glycyl-spicaminyl-amino)purine hydrochloride (663 mg) and triethylamine (1.6 ml), and the mixture was stirred for 12 hours. The solvent was removed by distillation, and the residue was purified by chromatography on a silica gel column with eluent systems of chloroform-methanol (from 7:1 to 5:1) to give SPK176 in the yield of 289 mg.

Physicochemical properties of SPK176
(1) Melting point: 177°–179° C.,
(2) Specific rotation $[\alpha]_D^{25}=+4.3°$ (c=0.1, in methanol),
(3) Elementary analysis:

|  | C | H | O | N |
|---|---|---|---|---|
| Calculated (%) | 54.63, | 7.15, | 20.38, | 17.84, |
| Found (%) | 55.01, | 7.12, | 20.14, | 17.73, |

(4) FD mass spectrum (m/z): 551 (M+H)$^+$, $C_{25}H_{39}O_7N_7$
(5) Infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 1.30–1.70 (12H, m), 2.06 (2H, dt, J=7.1, 7.1 Hz), 2.28 (2H, t, J=7.1 Hz), 3.60–3.80 (5H, m), 3.87 (1H, d, J=16.1 Hz), 3.89 (1H, d, J=16.1 Hz), 4.02 (1H, dd, J=2.1, <1 Hz), 4.14 (1H, dd, J=10.4, 10.4 Hz), 4.8–5.0 (2H, m), 5.65 (1H, brs), 5.80 (1H, m), 8.18 (1H, s), 8.31 (1H, s).

EXAMPLE 58

Preparation of SPK276

To 11-bromo-1-undecanol (5 g) dissolved in methylene chloride (70 ml) were added pyridinium chlorochromate (10.7 g) and Celite (11.0 g), and the mixture was stirred at room temperature for 12 hours. Then, the reaction mixture was filtered, concentrated and subjected to chromatography on a silica gel column with an eluent system of n-hexane-ethyl acetate (20:1) to give 11-bromo-1-undecanal (3.57 g). To the product dissolved in methylene chloride (50 ml) was added (carbomethoxymethylene)triphenylphosphorane (5.76 g), and the mixture was stirred. The reaction mixture was concentrated, and the residue thus obtained was subjected to chromatography on a silica gel column with an eluent system of n-hexane-ethyl acetate (20:1) to give the methyl ester of 13-bromo-2-tridecenoic acid (4.16 g). The product was dissolved in methanol and stirred under hydrogen atmosphere in the presence of palladium/carbon (1.5 g) for 18 hours. The reaction mixture was filtered and concentrated to give the methyl ester of 13-bromotridecanoic acid (3.22 g). 50% Aqueous ethanol (100 ml), in which potassium hydroxide (2.95 g) had been dissolved, was added to the methyl ester, and the mixture was stirred at 60° C. for 1 hour. Ethanol in the reaction mixture was removed by distillation, and the residue was acidified to a weak acidic range of pH by adding citric acid and extracted with ethyl acetate. The organic layer was dried and concentrated to give 13-bromotridecanoic acid (2.61 g). After the product was dissolved in N,N-dimethylformamide (DMF, 50 ml), para-nitrophenol (1.24 g) and N,N'-dicyclohexylcarbodiimide (1.84 g) were added, and the mixture was stirred for 12 hours. Then, precipitates produced was removed by filtration and the DMF was removed by distillation. The residue was subjected to chromatography on a silica gel column with eluent systems of n-hexane-ethyl acetate (from 200:1 to 50:1) to give the active ester of 13-bromotridecanoic acid (1.73 g). The active ester (540 mg) was dissolved in DMF (30 ml), and 6-(4'-N-glycyl-spicaminyl-amino)purine hydrochloride (500 mg) and triethylamine (2.0 ml) were added to the solution. The mixture was stirred for 12 hours. After the solvent was removed by distillation, the residue was subjected to chromatography on a silica gel column with eluent systems of chloroform-methanol (from 7:1 to 5:1) to give SPK276 in the yield of 227 mg.

Physicochemical properties of SPK276

(1) Melting point: 152°–153° C., (2) Specific rotation $[\alpha]_D^{25}=+5.5°$ (c=0.1, in methanol), (3) Elementary analysis:

|  | C | H | O | N |
|---|---|---|---|---|
| Calculated (%) | 49.24, | 6.73, | 17.01, | 14.89, |
| Found (%) | 49.04, | 6.81, | 16.74, | 15.26, |

(4) FD mass spectrum (m/z): 658, 660 $(M)^+$, $C_{27}H_{44}N_7O_7Br$ (5) Infrared spectrum (KBr disc): 3300 $cm^{-1}$, 1630 $cm^{-1}$, (6) Proton nuclear magnetic resonance spectrum (500 MHz, in $CD_3OD$) $\delta_H$: 1.20–1.70 (18H, m), 1.82 (2H, m), 2.28 (2H, t, J=7.2 Hz), 3.42 (2H, t, J=7.3 Hz), 3.60–3.80 (5H, m), 3.87 (1H, d, J=16.1 Hz), 3.89 (1H, d, J=16.1 Hz), 4.01 (1H, dd, J=2.1, <1 Hz), 4.14 (1H, dd, J=10.4, 10.4 Hz), 5.68 (1H, brs), 8.12 (1H, brs), 8.30 (1H, s).

EXAMPLE 59

Preparation of SPK273

To 12-bromo-1-dodecanol (5 g) dissolved in methylene chloride (70 ml) were added pyridinium chlorochromate (10.1 g) and Celite (11.0 g), and the mixture was stirred at room temperature for 12 hours. Then, the reaction mixture was filtered, concentrated and subjected to chromatography on a silica gel column with an eluent system of n-hexane-ethyl acetate (20:1) to give 12-bromo-1-dodecanal (3.72 g). To the product dissolved in methylene chloride (50 ml) was added (carbomethoxymethylene)triphenylphosphorane (8.80 g), and the mixture was stirred. The reaction mixture was concentrated, and the residue thus obtained was subjected to chromatography on a silica gel column with an eluent system of n-hexane-ethyl acetate (20:1) to give the methyl ester of 14-bromo-2-tetradecenoic acid (4.14 g). The product was dissolved in methanol and stirred under hydrogen atmosphere in the presence of palladium/carbon (1.5 g) for 18 hours. The reaction mixture was filtered and concentrated to give the methyl ester of 14-bromotetradecanoic acid (3.35 g). 50% Aqueous ethanol (100 ml), in which potassium hydroxide (2.90 g) had been dissolved, was added to the methyl ester, and the mixture was stirred at 60° C. for 1 hour. Ethanol in the reaction mixture was removed by distillation, and the residue was acidified to a weak acidic range of pH by adding citric acid and extracted with ethyl acetate. The organic layer was dried and concentrated to give 14-bromotetradecanoic acid (3.55 g). After the product was dissolved in N,N-dimethylformamide (DMF, 50 ml), para-nitrophenol (1.61 g) and N,N'-dicyclohexylcarbodiimide (2.39 g) were added, and the mixture was stirred for 12 hours. Then, precipitates produced was removed by filtration and the DMF was removed by distillation. The residue was subjected to chromatography on a silica gel column with eluent systems of n-hexane-ethyl acetate (from 200:1 to 50:1) to give the active ester of 14-bromotetradecanoic acid (2.57 g). The active ester (655 mg) was dissolved in DMF (30 ml), and 6-(4'-N-glycyl-spicaminyl-amino)purine hydrochloride (500 mg) and triethylamine (2.0 ml) were added to the solution. The mixture was stirred for 12 hours. After the solvent was removed by distillation, the residue was subjected to chromatography on a silica gel column with eluent systems of chloroform-methanol (from 7:1 to 5:1) to give SPK273 in the yield of 219 mg.

Physicochemical properties of SPK273

(1) Melting point: 161°–163° C., (2) Specific rotation $[\alpha]_D^{25}=-4.4°$ (c=0.1, in methanol), (3) Elementary analysis:

|  | C | H | O | N |
|---|---|---|---|---|
| Calculated (%) | 50.00, | 6.89, | 16.65, | 14.58, |
| Found (%) | 49.78, | 7.03, | 16.89, | 14.92, |

(4) FD mass spectrum (m/z): 672, 674 $(M)^+$, $C_{28}H_{46}N_7O_7Br$ (5) Infrared spectrum (KBr disc): 3300 $cm^{-1}$, 1630 $cm^{-1}$, (6) Proton nuclear magnetic resonance spectrum (500 MHz, in $CD_3OD$) $\delta_H$: 1.30–1.70 (20H, m), 1.84 (2H, m), 2.28 (2H, t, J=7.1 Hz), 3.43 (2H, t, J=7.1 Hz), 3.60–3.80 (5H, m), 3.87 (1H, d, J=16.1 Hz), 3.89 (1H, d, J=16.1 Hz), 4.01 (1H, dd, J=2.1, <1 Hz), 4.14 (1H, dd, J=10.4, 10.4 Hz), 5.68 (1H, brs), 8.15 (1H, brs), 8.31 (1H, s).

EXAMPLE 60

Preparation of SPK275

15-Hydroxypentadecanoic acid (3.0 g) dissolved in a 10% methanolic hydrochloric acid solution was stirred for 1 hour. The mixture was then concentrated and distributed into ethyl acetate and water, and the ethyl acetate layer was dried over anhydrous sodium sulfate and concentrated to give the methyl ester of 15-hydroxypentadecanoic acid (3.0 g). To the methyl ester dissolved in methylene chloride were added pyridine (2.6 ml) and para-toluenesulfonyl chloride (2.5 g) at 0° C. and the mixture was stirred at room temperature for 18 hours. Then, the reaction mixture was concentrated and distributed into chloroform and water. The chloroform layer is dried and concentrated, and the residue thus obtained is subjected to chromatography on a silica gel column with an eluent system of n-hexane-ethyl acetate (20:1) to give the methyl ester of 15-para-toluenesulfonyloxypentadecanoic acid (3.40 g). To the product dissolved in acetonitrile (70 ml) were added sodium bromide (8.3 g), tetraethylammonium bromide (2.8 g) and triethylamine (2.3 ml), and the mixture was heated at 80° C. for 3.5 hours. Precipitates produced by cooling the reaction mixture was removed by filtration and the filtrate was concentrated. The residue thus obtained was distributed into ethyl acetate and water. The methyl ester of 15-bromopentadecanoic acid (2.40 g) was obtained. 50% Aqueous ethanol (100 ml), in which potassium hydroxide (2.1 g) was dissolved, was added to the product, and the mixture was stirred at 60° C. for 1 hour. Ethanol in the reaction mixture was evaporated, and the residue was acidified to a weak acidic range of pH and extracted with ethyl acetate. The organic layer was dried and concentrated to give 15-bromopentadecanoic acid (2.2 g). After the product was dissolved in N,N-dimethylformamide (DMF, 50 ml), para-nitrophenol (0.96 g) and N,N'-dicyclohexylcarbodiimide (1.42 g) were added, and the mixture was stirred for 12 hours. After precipitates produced were removed by filtration, DMF was evaporated and the residue was subjected to chromatography on a silica gel column with eluent systems of n-hexane-ethyl acetate (from 200:1 to 50:1) to give the active ester of 15-bromopentadecanoic acid (15 g). The active ester (591 mg) was dissolved in DMF (30 ml), 6-(4'-N-glycyl-spicaminyl-amino)purine hydrochloride (500 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK275 in the yield of 232 mg.

Physicochemical properties of SPK275
(1) Melting point: 179°–180° C.,
(2) Specific rotation $[\alpha]_D^{25} = -6.2°$ (c=0.1, in methanol),
(3) Elementary analysis:

|  | C | H | O | N |
|---|---|---|---|---|
| Calculated (%) | 50.73, | 7.05, | 16.31, | 14.28, |
| Found (%) | 51.14, | 7.13, | 16.49, | 14.63, |

(4) FD mass spectrum (m/z): 686, 688 $(M)^+$, $C_{29}H_{48}N_7O_7Br$ (5) Infrared spectrum (KBr disc): 3300 $cm^{-1}$, 1640 $cm^{-1}$, (6) Proton nuclear magnetic resonance spectrum (500 MHz, in $CD_3OD$) $\delta_H$: 1.25–1.70 (22H, m), 1.84 (2H, m), 2.28 (2H, t, J=7.1 Hz), 3.42 (2H, t, J=7.1 Hz), 3.60–3.80 (5H, m), 3.87 (1H, d, J=16.1 Hz), 3.89 (1H, d, J=16.1 Hz), 4.02 (1H, d, J=2.1, <1 Hz), 4.14 (1H, dd, J=10.4, 10.4 Hz), 5.65 (1H, brs), 8.12 (1H, brs), 8.31 (1H, s).

EXAMPLE 61

Preparation of SPK272

16-Hydroxyhexadecanoic acid (3.0 g) dissolved in a 10% methanolic hydrochloric acid solution was stirred for 1 hour. The mixture was then concentrated and distributed into ethyl acetate and water, and the ethyl acetate layer was dried over anhydrous sodium sulfate and concentrated to give the methyl ester of 16-hydroxyhexadecanoic acid (3.07 g). To the methyl ester dissolved in methylene chloride were added pyridine (2.6 ml) and para-toluenesulfonyl chloride (2.26 g) at 0° C., and the mixture was stirred at room temperature for 18 hours. Then, the reaction mixture was concentrated and distributed into chloroform and water. The chloroform layer is dried and concentrated, and the residue thus obtained is subjected to chromatography on a silica gel column with an eluent system of n-hexane-ethyl acetate (20:1) to give the methyl ester of 16-para-toluenesulfonyloxyhexadecanoic acid (3.47 g). To the product dissolved in acetonitrile (70 ml) were added sodium bromide (28 g), triethylammonium bromide (2.8 g) and triethylamine (5.6 ml), and the mixture was heated at 80° C. for 3.5 hours. Precipitates produced by cooling the reaction mixture was removed by filtration and the filtrate was concentrated. The residue thus obtained was distributed into ethyl acetate and water. The methyl ester of 16-bromohexadecanoic acid (2.60 g) was obtained. 50% Aqueous ethanol (100 ml), in which potassium hydroxide (2.12 g) was dissolved, was added to the product, and the mixture was stirred at 60° C. for 1 hour. Ethanol in the reaction mixture was evaporated, and the residue was acidified to a weak acidic range of pH and extracted with ethyl acetate. The organic layer was dried and concentrated to give 16-bromohexadecanoic acid (2.24 g). After the product was dissolved in N,N-dimethylformamide (DMF, 50 ml), para-nitrophenol (0.93 g) and N,N'-dicyclohexylcarbodiimide (1.38 g) were added, and the mixture was stirred for 12 hours. After precipitates produced were removed by filtration, DMF was evaporated and the residue was subjected to chromatography on a silica gel column with eluent systems of n-hexane-ethyl acetate (from 200:1 to 50:1) to give the active ester of 16-bromohexadecanoic acid (1.5 g). The active ester (591 mg) was dissolved in DMF (30 ml), 6-(4'-N-glycyl-spicaminyl-amino)purine hydrochloride (500 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK272 in the yield of 260 mg.

Physicochemical properties of SPK272
(1) Melting point: 182°–183° C.,
(2) Specific rotation $[\alpha]_D^{25} = -5.2°$ (c=0.1, in methanol),
(3) Elementary analysis:

|  | C | H | O | N |
|---|---|---|---|---|
| Calculated (%) | 51.43, | 7.19, | 15.98, | 13.40, |
| Found (%) | 51.83, | 6.79, | 15.76, | 14.30, |

(4) FD mass spectrum (m/z): 700, 702 $(M)^+$, $C_{30}H_{50}N_7O_7Br$ (5) Infrared spectrum (KBr disc): 3300 $cm^{-1}$, 1630 $cm^{-1}$, (6) Proton nuclear magnetic resonance spectrum (500 MHz, in $CD_3OD$) $\delta_H$: 1.25–1.70 (24H, m), 1.84 (2H, m), 2.28 (2H, t, J=7.1 Hz), 3.42 (2H, t, J=7.1 Hz), 3.60–3.80 (5H, m), 3.87 (1H, d, J=16.1 Hz), 3.89 (1H, d, J=16.1 Hz), 4.02 (1H, d, J=2.1, <1 Hz), 4.14 (1H, dd, J=10.4, 10.4 Hz), 5.65 (1H, brs), 8.12 (1H, brs), 8.32 (1H, s).

EXAMPLE 62

Preparation of SPK278

To 11-bromo-1-undecanol (5 g) dissolved in methylene chloride (70 ml) were added pyridinium chlorochromate (10.7 g) and Celite (11.0 g), and the mixture was stirred at room temperature for 12 hours. Then, the reaction mixture was filtered, concentrated and subjected to chromatography on a silica gel column with an eluent system of n-hexane-ethyl acetate (20:1) to give 11-bromo-1-undecanal (3.57 g). To the product dissolved in methylene chloride (50 ml) was added (carbomethoxymethylene)triphenylphosphorane (4.66 g), and the mixture was stirred. The reaction mixture was concentrated, and the residue thus obtained was subjected to chromatography on a silica gel column with an eluent system of n-hexane-ethyl acetate (20:1) to give the methyl ester of 13-bromo-2-tridecenoic acid (4.16 g). The product was dissolved in methanol and stirred under hydrogen atmosphere in the presence of palladium/carbon (1.5 g) for 18 hours. The reaction mixture was filtered and concentrated to give the methyl ester of 13-bromotetradecanoic acid (3.22 g). To the methyl ester dissolved in acetonitrile were added calcium chloride (9.4 g) and tetraethylammonium chloride (2.8 g), and the mixture was stirred at 80° C. for 3 hours, and then cooled and concentrated. The residue was distributed into ethyl acetate and water, and the ethyl acetate layer was dried and concentrated to give the methyl ester of 13-chlorotridecanoic acid (2.08 g). 50% Aqueous ethanol (100 ml), in which potassium hydroxide (2.27 g) had been dissolved, was added to the methyl ester, and the mixture was stirred at 60° C. for 1 hour. Ethanol in the reaction mixture was evaporated, and the residue was acidified to a weak acidic range of pH by adding citric acid and extracted with ethyl acetate. The organic layer was dried and concentrated to give 13-chlorotridecanoic acid (1.69 g). After the product was dissolved in N,N-dimethylformamide (DMF, 50 ml), para-nitrophenol (0.94 g) and N,N'-dicyclohexylcarbodiimide (1.39 g) were added, and the mixture was stirred for 12 hours. Then, precipitates produced was removed by filtration and the DMF was removed by distillation. The residue was subjected to chromatography on a silica gel column with eluent systems of n-hexane-ethyl acetate (from 200:1 to 50:1) to give the active ester of 13-chlorotetradecanoic acid (1.01 g). The active ester (600 mg) was dissolved in DMF (30 ml), and 6-(4'-N-glycyl-spicaminyl-amino)purine hydrochloride (500 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK278 in the yield of 222 mg.

Physicochemical properties of SPK278

(1) Melting point: 175°–176° C.,
(2) Specific rotation $[\alpha]_D^{25}=+6.4°$ (c=0.1, in methanol),
(3) Elementary analysis:

|  | C | H | O | N |
|---|---|---|---|---|
| Calculated (%) | 52.81, | 7.22, | 18.24, | 15.97, |
| Found (%) | 53.18, | 6.95, | 17.90, | 16.21, |

(4) FD mass spectrum (m/z): 614, 616 (M)$^+$, $C_{27}H_{44}N_7O_7Cl$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.25–1.50 (16H, m), 1.64 (2H, m), 1.75 (2H, m), 2.28 (2H, t, J=7.1 Hz), 3.53 (2H, t, J=7.1 Hz), 3.60–3.80 (5H, m), 3.87 (1H, d, J=16.1 Hz), 3.89 (1H, d, J=16.1 Hz), 4.02 (1H, dd, J=2.0, <1 Hz), 4.15 (1H, dd, J=10.4, 10.4 Hz), 5.69 (1H, brs), 8.13 (1H, brs), 8.30 (1H, s).

EXAMPLE 63

Preparation of SPK280

To 12-bromo-1-dodecanol (5 g) dissolved in methylene chloride (70 ml) were added pyridinium chlorochromate (10.1 g) and Celite (11.0 g), and the mixture was stirred at room temperature for 12 hours. Then, the reaction mixture was filtered, concentrated and subjected to chromatography on a silica gel column with an eluent system of n-hexane-ethyl acetate (20:1) to give 12-bromo-1-dodecanal (3.72 g). To the product dissolved in methylene chloride (50 ml) was added (carbomethoxymethylene)triphenylphosphorane (8.80 g), and the mixture was stirred. The reaction mixture was concentrated, and the residue thus obtained was subjected to chromatography on a silica gel column with an eluent system of n-hexane-ethyl acetate (20:1) to give the methyl ester of 14-bromo-2-tetradecenoic acid (4.14 g). The product was dissolved in methanol and stirred under hydrogen atmosphere in the presence of palladium/carbon (1.5 g) for 18 hours. The reaction mixture was filtered and concentrated to give the methyl ester of 14-bromotetradecanoic acid (3.25 g). To the methyl ester dissolved in acetonitrile were added calcium chloride (12.3 g) and tetraethylammonium chloride (3.7 g), and the mixture was stirred at 80° C. for 3 hours, and then cooled and concentrated. The residue was distributed into ethyl acetate and water, and the ethyl acetate layer was dried and concentrated to give the methyl ester of 14-chlorotetradecanoic acid (2.37 g). 50% Aqueous ethanol (100 ml), in which potassium hydroxide (2.90 g) had been dissolved, was added to the methyl ester, and the mixture was stirred at 60° C. for 1 hour. Ethanol in the reaction mixture was evaporated, and the residue was acidified to a weak acidic range of pH by adding citric acid and extracted with ethyl acetate. The organic layer was dried and concentrated to give 14-chlorotetradecanoic acid (2.02 g). After the product was dissolved in N,N-dimethylformamide (DMF, 50 ml), para-nitrophenol (1.07 g) and N,N'-dicyclohexylcarbodiimide (1.59 g) were added, and the mixture was stirred for 12 hours. Then, precipitates produced was removed by filtration and the DMF was removed by distillation. The residue was subjected to chromatography on a silica gel column with eluent systems of n-hexane-ethyl acetate (from 200:1 to 50:1) to give the active ester of 14-chlorotetradecanoic acid (1.86 g). The active ester (500 mg) was dissolved in DMF (30 ml), and 6-(4'-N-glycyl-spicaminyl-amino)purine hydrochloride (500 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK280 in the yield of 247 mg.

Physicochemical properties of SPK280

(1) Melting point: 166°–168° C.,
(2) Specific rotation $[\alpha]_D^{25}=-3.6°$ (c=0.1, in methanol),
(3) Elementary analysis:

|  | C | H | O | N |
|---|---|---|---|---|
| Calculated (%) | 53.54, | 7.38, | 17.83, | 15.61, |
| Found (%) | 53.89, | 6.96, | 18.15, | 15.22, |

(4) FD mass spectrum (m/z): 628, 630 (M)$^+$, $C_{28}H_{46}N_7O_7Cl$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.25–1.50 (18H, m), 1.63 (2H, m), 1.75 (2H, m), 2.28 (2H, t, J=7.1 Hz), 3.54 (2H, t, J=7.1 Hz), 3.60–3.80 (5H, m), 3.87 (1H, d, J=16.1 Hz), 3.89 (1H, d, J=16.1 Hz), 4.02 (1H, dd, J=2.1, <1 Hz), 4.14 (1H, dd, J=10.4, 10.4 Hz), 5.68 (1H, brs), 8.12 (1H, brs), 8.30 (1H, s).

EXAMPLE 64

Preparation of SPK277

15-Hydroxypentadecanoic acid (3.0 g) dissolved in a 10% methanolic hydrochloric acid solution was stirred for 1 hour. The mixture was then concentrated and distributed into ethyl acetate and water, and the ethyl acetate layer was dried over anhydrous sodium sulfate and concentrated to give the methyl ester of 15-hydroxypentadecanoic acid (3.0 g). To the methyl ester dissolved in methylene chloride were added pyridine (2.6 ml) and para-toluenesulfonyl chloride (2.5 g) at 0° C., and the mixture was stirred at room temperature for 18 hours. Then, the reaction mixture was concentrated and distributed into chloroform and water. The chloroform layer is dried and concentrated, and the residue thus obtained is subjected to chromatography on a silica gel column with an eluent system of n-hexane-ethyl acetate (20:1) to give the methyl ester of 15-para-toluenesulfonyloxypentadecanoic acid (3.47 g). To the product (3 g) dissolved in acetonitrile (70 ml) were added calcium chloride (7.7 g), tetraethylammonium bromide (2.4 g) and triethylamine (2.0 ml), and the mixture was heated at 80° C. for 3.5 hours. Precipitates produced by cooling the reaction mixture was removed by filtration and the filtrate was concentrated. The residue thus obtained was distributed into ethyl acetate and water. The methyl ester of 15-chloropentadecanoic acid (1.49 g) was obtained. 50% Aqueous ethanol (100 ml), in which potassium hydroxide (1.5 g) was dissolved, was added to the product, and the mixture was stirred at 60° C. for 1 hour. Ethanol in the reaction mixture was evaporated, and the residue was acidified to a weak acidic range of pH and extracted with ethyl acetate. The organic layer was dried and concentrated to give 15-chloropentadecanoic acid (1.23 g). After the product was dissolved in N,N-dimethylformamide (DMF, 50 ml), para-nitrophenol (0.62 g) and N,N'-dicyclohexylcarbodiimide (0.92 g) were added, and the mixture was stirred for 12 hours. After precipitates produced were removed by filtration, DMF was evaporated and the residue was subjected to chromatography on a silica gel column with eluent systems of n-hexane-ethyl acetate (from 200:1 to 50:1) to give the active ester of 15-chloropentadecanoic acid (1.5 g). The active ester (515 mg) was dissolved in DMF (30 ml), 6-(4'-N-glycyl-spicaminyl-amino)purine hydrochloride (500 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK277 in the yield of 219 mg.

Physicochemical properties of SPK277

(1) Melting point: 177°–179° C.,
(2) Specific rotation $[\alpha]_D^{25}$=−8.4° (c=0.1, in methanol),
(3) Elementary analysis:

|  | C | H | O | N |
|---|---|---|---|---|
| Calculated (%) | 54.24, | 7.53, | 17.44, | 15.27, |
| Found (%) | 53.98, | 7.70, | 17.59, | 14.96, |

(4) FD mass spectrum (m/z): 642, 644 (M)$^+$, $C_{29}H_{48}N_7O_7Cl$ (5) Infrared spectrum (KBr disc): 3400 cm$^{-1}$, 1620 cm$^{-1}$, (6) Proton nuclear magnetic resonance spectrum (500 MHz, in CD$_3$OD) $\delta_H$: 1.20–1.50 (20H, m), 1.63 (2H, m), 1.76 (2H, m), 2.29 (2H, t, J=7.1 Hz), 3.54 (2H, t, J=7.1 Hz), 3.60–3.80 (5H, m), 3.87 (1H, d, J=16.1 Hz), 3.89 (1H, d, J=16.1 Hz), 4.02 (1H, dd, J=2.1, <1 Hz), 4.14 (1H, dd, J=10.4, 10.4 Hz), 5.68 (1H, brs), 8.12 (1H, brs), 8.30 (1H, s).

EXAMPLE 65

Preparation of SPK279

To 12-bromododecanol (5 g) dissolved in methylene chloride (30 ml) were added Celite (5.0 g) and pyridinium chlorochromate (5.2 g), and the mixture was stirred at room temperature for 12 hours. Then, the reaction mixture was filtered and subjected to chromatography on a silica gel column with an eluent system of n-hexane-ethyl acetate (30:1) to give 12-bromododecanal (4.4 g). To 12-bromododecanal (4.4 g) dissolved in methylene chloride (50 ml) was added (carbomethoxymethylene)-triphenylphosphorane (6.75 g), and the mixture was stirred for 4 hours. Then, the reaction mixture was concentrated, and the residue thus obtained was subjected to chromatography on a silica gel column with an eluent system of n-hexane-ethyl acetate (30:1) to give the methyl ester of 14-bromo-2-tetradecenoic acid (4.91 g). The product was dissolved in acetonitrile (30 ml), and 1M tetra-n-butylammonium chloride in THF (27 ml) and potassium fluoride (7.6 g) were added. The mixture was heated under reflux for 12 hours. The reaction mixture was concentrated and subjected to chromatography on a silica gel column with an eluent system of n-hexane-ethylacetate 100:1 to give the methyl ester of 14-fluoro-3-tetradecenoic acid (3.3 g).

The methyl ester of 14-fluoro-2-tetradecenoic acid (3.3 g) was dissolved in methanol (20 ml), in which 10% palladium/carbon (0.9 g) was suspended, and a 10% methanolic hydrochloric acid solution (2 ml) was added. The mixture was stirred under hydrogen atmosphere for 12 hours. The reaction mixture was filtered, and a large amount of chloroform was added to the filtrate. The chloroform layer was washed with a saturated aqueous sodium hydrogen carbonate solution and water. The organic layer was dried and concentrated to give the methyl ester of 14-fluorotetradecanoic acid (2.5 g). The methyl ester (2.5 g) was dissolved in a solution of potassium hydroxide in ethanol-water (1:1), and the mixture was stirred at 80° C. for 30 minutes. The reaction mixture was acidified by adding citric acid and extracted with ethyl acetate. The ethyl acetate layer was dried over anhydrous sodium sulfate and concentrated to give 14-fluorotetradecanoic acid (2.3 g).

After the product (2.3 g) and para-nitrophenol (1.3 g) were dissolved in N,N-dimethylformamide (DMF, 30 ml), N,N'-dicyclohexylcarbodiimide (1.9 g) was added, and the mixture was stirred for 12 hours. The reaction mixture was filtered and concentrated to give the active ester of 14-fluorotetradecanoic acid. The active ester (500 mg) was dissolved in DMF, and 6-(4'-N-glycyl-spicaminyl-amino)purine trifluoroacetate (0.52 g) and triethylamine (1.6 ml) were added to the solution. The mixture was stirred for 12 hours. After the solvent was evaporated, the residue was subjected to chromatography on a silica gel column with eluent systems of chloroform-methanol (from 7:1 to 5:1) to give SPK279 in the yield of 227 mg.

Physicochemical properties of SPK279

(1) Melting point: 193°–194° C., (2) Specific rotation $[\alpha]_D^{25}=+6.5°$ (c=0.1, in methanol), (3) Elementary analysis:

|  | C | H | O | N |
|---|---|---|---|---|
| Calculated (%) | 54.98, | 7.58, | 18.31, | 16.03, |
| Found (%) | 54.82, | 7.71, | 18.55, | 15.84, |

(4) FD mass spectrum (m/z): 613 (M+H)$^+$, $C_{28}H_{46}N_7O_7F$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.25–1.75 (22H, m), 2.28 (3H, t, J=7.1 Hz), 3.60–3.80 (5H, m), 3.87 (1H, d, J=16.1 Hz), 3.89 (1H, d, J=16.1 Hz), 4.01 (1H, dd, J=2.1, <1 Hz), 4.13 (1H, dd, J=10.4, 10.4 Hz), 4.40 (2H, dt, J=6.4, 47.1 Hz), 5.65 (1H, brs), 8.12 (1H, brs), 8.30 (1H, s).

EXAMPLE 66

Preparation of SPK247

15-Hydroxypentadecanoic acid (1 g) dissolved in a 10% methanolic hydrochloric acid solution (20 ml) was stirred for 1 hour. The reaction mixture was then concentrated and distributed into chloroform and water and further washed with a 1% aqueous sodium hydrogen carbonate solution and water, dried with anhydrous sodium sulfate and concentrated to give the methyl ester of 15-hydroxypentadecanoic acid (1.01 g). To the methyl ester dissolved in pyridine (20 ml) was added para-toluenesulfonyl chloride (0.70 g), and the mixture was stirred for 8 hours. Then, the pyridine was evaporated and distributed into chloroform and water, and the chloroform layer was dried with anhydrous sodium sulfate, concentrated and subjected to chromatography on a silica gel column with an eluent system of n-hexane-ethyl acetate (50:1) to give the methyl ester of 15-para-toluenesulfonyloxypentadecanoic acid (1.46 g). To the product (3 g) dissolved in acetonitrile (30 ml) was added 1M tetra-n-butylammonium bromide in tetrahydrofuran (6 ml), and the mixture was stirred for 48 hours. Then, the reaction mixture was concentrated, and the residue was subjected to chromatography on a silica gel column with an eluent system of n-hexane-ethyl acetate (100:1) to give the methyl ester of 15-fluoropentadecanoic acid (0.63 g). The methyl ester was dissolved in a mixture of ethanol-water (1:1) and potassium hydroxide (0.8 g) was added to the solution. The resulting mixture was stirred at 80° C. for 30 minutes. The reaction mixture was concentrated, acidified to a weak acidic range of pH by adding citric acid and extracted with ethyl acetate. The ethyl acetate layer was dried over anhydrous sodium sulfate to give 15-fluoropentadecanoic acid (0.53 g).

After 15-fluoropentadecanoic acid (500 mg) and para-nitrophenol (268 mg) were dissolved in N,N-dimethylformamide (DMF, 30 ml), N,N'-dicyclohexylcarbodiimide (396 mg) was added, and the mixture was stirred for 12 hours. After the reaction mixture was filtered and concentrated to give the active ester of 15-fluoropentadecanoic acid. The active ester was dissolved in DMF, and 6-(4'-N-glycyl-spicaminyl-amino)purine trifluoroacetate (735 mg) and triethylamine (2.0 ml) were added to the solution. The mixture was stirred for 12 hours. After the solvent was evaporated, the residue was subjected to chromatography on a silica gel column with eluent systems of chloroform-methanol (from 7:1 to 5:1) to give SPK247 in the yield of 230 mg.

Physicochemical properties of SPK247

(1) Melting point: 185°–186° C., (2) Specific rotation $[\alpha]_D^{25}=-1.2°$ (c=0.1, in methanol), (3) Elementary analysis:

|  | C | H | O | N |
|---|---|---|---|---|
| Calculated (%) | 55.67, | 7.73, | 17.90, | 15.67, |
| Found (%) | 56.02, | 7.21, | 18.04, | 15.39, |

(4) FD mass spectrum (m/z): 627 (M+H)$^+$, $C_{29}H_{48}N_7O_7F$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.25–1.70 (24H, m), 2.28 (2H, t, J=7.2 Hz), 3.60–3.80 (5H, m), 3.86 (1H, d, J=16.1 Hz), 3.89 (1H, d, J=16.1 Hz), 4.01 (1H, dd, J=2.1, <1 Hz), 4.14 (1H, dd, J=10.4, 10.4 Hz), 4.40 (2H, dr, J=6.4, 47.1 Hz), 5.68 (1H, brs), 8.14 (1H, brs), 8.30 (1H, s).

EXAMPLE 67

Preparation of SPK258

To 2-bromotetradecanoic acid (2 g) dissolved in N,N-dimethylformamide (DMF, 50 ml) were added para-nitrophenol (0.90 g) and N,N'-dicyclohexylcarbodiimide (1.34 g), and the mixture was stirred for 12 hours. After precipitates produced was removed by filtration, the solvent (DMF) was evaporated and the residue was subjected to chromatography on a silica gel column with eluent systems of n-hexane-ethyl acetate (from 200:1 to 50:1) to give the active ester of 2-bromotetradecanoic acid (1.59 g). To the active ester dissolved in DMF (30 ml) were added 6-(4'-N-glycyl-spicaminyl-amino)purine hydrobromide (500 mg) and triethylamine (2.0 ml). The mixture was stirred for 12 hours. After the solvent was evaporated, the residue was subjected to chromatography on a silica gel column with eluent systems of chloroform-methanol (from 7:1 to 5:1) to give SPK258 in the yield of 202 mg.

Physicochemical properties of SPK258

(1) Melting point: 175°–177° C., (2) Specific rotation $[\alpha]_D^{25}=-8.4°$ (c=0.1, in methanol), (3) Elementary analysis:

|  | C | H | O | N |
|---|---|---|---|---|
| Calculated (%) | 50.00, | 6.89, | 16.65, | 14.58, |
| Found (%) | 50.39, | 6.44, | 16.59, | 14.32, |

(4) FD mass spectrum (m/z): 672, 674 (M)$^+$, $C_{28}H_{46}N_7O_7Br$ (5) Infrared spectrum (KBr disc): 3300 cm$^{-1}$, 1650 cm$^{-1}$, (6) Proton nuclear magnetic resonance spectrum (500 MHz, in CD$_3$OD) $\delta_H$H: 0.90 (3H, t, J=7.2 Hz), 1.20–1.60 (20H, m), 1.90–2.10 (2H, m), 3.60–3.80 (5H, m), 3.80–4.00 (2H, m), 4.02 (1H, dd, J=2.1, <1 Hz), 4.14 (1H, dd, J=10.4, 10.4 Hz), 4.38 (1H, dd, J=6.4, 6.4 Hz), 5.67 (1H, brs), 8.12 (1H, brs), 8.32 (1H, s).

EXAMPLE 68

Preparation of SPK259

To 2-bromotetradecanoic acid (2 g) dissolved in acetonitrile (100 ml) were added calcium chloride (7.2 g), tetraethylammonium chloride (2.2 g) and triethylamine (0.84 ml), and the mixture was stirred at 80° C. for 3 hours. After precipitates produced by cooling the reaction mixture was removed by filtration, the filtrate was concentrated and the residue was distributed into ethyl acetate and an aqueous citric solution. The ethyl acetate layer was dried and concentrated to give 2-chloro-tetradecanoic acid (1.29 g). To 2-chlorotetradecanoic acid (1.29 g) dissolved in N,N-dimethylformamide (DMF, 50 ml) were added para-nitrophenol (0.68 g) and N,N'-dicyclohexylcarbodiimide (1.1 g), and the mixture was stirred for 12 hours. After precipitates were removed by filtration, the solvent (DMF) was evaporated and the residue was subjected to chromatography on a silica gel column with eluent systems of n-hexane-ethyl acetate (from 200:1 to 50:1) to give the active ester of 2-chlorotetradecanoic acid (11.12 g). To the active ester (500 mg) dissolved in DMF (30 ml) were added 6-(4'-N-glycyl-spicaminyl-amino)purine hydrochloride (500 mg) and triethylamine (2.0 ml). The mixture was stirred for 12 hours. After the solvent was evaporated, the residue was subjected to chromatography on a silica gel column with eluent systems of chloroform-methanol (from 7:1 to 5:1) to give SPK259 in the yield of 202 mg.

Physicochemical properties of SPK259

(1) Melting point: 188°–189° C.,
(2) Specific rotation $[\alpha]_D^{25}$=+12.8° (c=0.1, in methanol),
(3) Elementary analysis:

|  | C | H | O | N |
|---|---|---|---|---|
| Calculated (%) | 53.54, | 7.38, | 17.83, | 15.61, |
| Found (%) | 53.98, | 6.98, | 18.09, | 15.30, |

(4) FD mass spectrum (m/z): 628, 630 (M)$^+$, $C_{28}H_{46}N_7O_7Cl$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 0.89 (3H, J=7.1 Hz), 1.20–1.60 (20H, m), 1.80–2.10 (2H, m), 3.60–3.80 (5H, m), 3.85–4.00 (2H, m), 4.02 (1H, dd, J=2.1, <1 Hz), 4.14 (1H, dd, J=10.4, 10.4 Hz), 4.40 (1H, m), 5.68 (1H, brs), 8.12 (1H, s), 8.29 (1H, s).

EXAMPLE 69

Preparation of SPK182

Ethyl bromodifluoroacetate (6.0 g) and dodecyl aldehyde (1.84 g) were mixed with anhydrous tetrahydrofuran (40 ml) under argon atmosphere, and the solution was added dropwise to a suspension of zinc powder (2.2 g) and copper bromide (I) (0.22 g) in anhydrous tetrahydrofuran (40 ml) which was heated to a refluxing temperature. The mixture, after heating under reflux for 5 hours, was cooled and concentrated under reduced pressure. The residue was subjected to chromatography on a silica gel column with eluent systems of n-hexane-ethyl acetate (from 20:1 to 10:1) to give ethyl 2,2-difluoro-3-hydroxytetradecanoate (0.92 g). After the mixture of ethyl 2,2-difluoro-3-hydroxytetradecanoate (0.92 g) and 1,1'-thiocarbonyl imidazole (1.26 g) in 1,2-dichloroethane was heated under reflux for 1 hour, it was cooled and concentrated. The residue was subjected to chromatography on a silica gel column with eluent systems of n-hexane-ethyl acetate (from 30:1 to 10:1) to give ethyl 2,2-difluoro-3-imidazoylthiocarbonyloxytetradecanoate (1.32 g). To a solution of ethyl 2,2-difluoro-3-imidazoylthiocarbonyloxytetradecanoate (1.32 g) dissolved in toluene (40 ml) under argon atmosphere, which was heated under reflux, was added dropwise a solution of tri-n-butyltin hydride (2.93 ml) in toluene (70 ml). The mixture, after heating under reflux for 2 hours, was concentrated under reduced pressure. The residue was subjected to chromatography on a silica gel column with eluent systems of n-hexane-ethyl acetate (from 300:1 to 50:1) to give ethyl 2,2-difluorotetradecanoate (0.67 g). To a solution of ethyl 2,2-difluorotetradecanoate (489 mg) in N,N-dimethylformamide (30 ml) were added 6-(4'-N-glycyl-spicaminyl-amino)purine hydrochloride (300 mg) and triethylamine (1.5 ml). The mixture was stirred for 12 hours. After the solvent was evaporated, the residue was subjected to chromatography on a silica gel column with eluent systems of chloroform-methanol-water (from 8.5:1:0.05 to 7:1:0.05) to give SPK182 in the yield of 95 mg.

Physicochemical properties of SPK182

(1) Melting point: 181°–183° C.,
(2) Specific rotation $[\alpha]_D^{25}$=–6.2° (c=0.1, in methanol),
(3) Elementary analysis:

|  | C | H | O | N |
|---|---|---|---|---|
| Calculated (%) | 53.41, | 7.20, | 17.79, | 15.57, |
| Found (%) | 53.63, | 6.79, | 18.03, | 15.40, |

(4) FD mass spectrum (m/z): 630 (M)$^+$, $C_{28}H_{45}N_7O_7F_2$ (5) Infrared spectrum (KBr disc): 3250 cm$^{-1}$, 1660 cm$^{-1}$, 1630 cm$^{-1}$, (6) Proton nuclear magnetic resonance spectrum (500 MHz, in CDCl$_3$-CD$_3$OD) $\delta_H$: 0.89 (3H, t, J=7.1 Hz), 1.25–1.60 (20H, m), 2.10 (2H, m), 3.60–3.80 (5H, m), 3.96 (1H, d, J=16.7 Hz), 3.98 (1H, d, J=16.7 Hz), 4.02 (1H, dd, J=2.1, <1 Hz), 4.15 (1H, dd, J=10.4, 10.4 Hz), 5.76 (1H, brs), 8.13 (1H, brs), 8.31 (1H, s).

EXAMPLE 70

Preparation of SPK193

Ethyl bromodifluoroacetate (11.2 g) and tetradecyl aldehyde (3.96 g) were mixed with anhydrous tetrahydrofuran (80 ml) under argon atmosphere, and the solution was added dropwise to a suspension of zinc powder (4.1 g) and copper bromide (I) (0.41 g) in anhydrous tetrahydrofuran (80 ml) which was heated to a refluxing temperature. The mixture, after heating under reflux for 5 hours, was cooled and concentrated under reduced pressure. The residue was subjected to chromatography on a silica gel column with eluent systems of n-hexane-ethyl acetate (from 20:1 to 10:1) to give ethyl 2,2-difluoro-3-hydroxyhexadecanoate (1.99 g). After the mixture of ethyl 2,2-difluoro-3-hydroxyhexadecanoate (1.00 g) and 1,1'-thiocarbonyl imidazole (1.18 g) in 1,2-dichloroethane was heated under reflux for 1 hour, it was cooled and concentrated. The residue was subjected to chromatography on a silica gel column with eluent systems of n-hexane-ethyl acetate (from 30:1 to 10:1) to give ethyl 2,2-difluoro-3-imidazoylthiocarbonyloxyhexadecanoate (1.32 g). To a solution of ethyl 2,2-difluoro-3-imidazoylthiocarbonyloxyhexadecanoate (0.86 g) dissolved in toluene (40 ml) under argon atmosphere, which was heated under reflux, was added dropwise a solution of tri-n-butyltin hydride (1.07 ml) in toluene (80 ml). The mixture, after heating under reflux for 2 hours, was concentrated under reduced pressure. The residue was subjected to chromatography on a silica gel column with eluent systems of n-hexane-ethyl acetate (from 300:1 to 50:1) to give ethyl 2,2-difluorohexadecanoate (0.51 g). To a solution of ethyl 2,2-difluorohexadecanoate (300 mg) in N,N-dimethylformamide (30 ml) were added 6-(4'-N-glycyl-spicaminyl-amino)purine hydrochloride (300 mg) and triethylamine (1.1 ml). The mixture was stirred for 12 hours. After the solvent was evaporated, the residue was subjected to chromatography on a silica gel column with eluent systems of chloroform-methanol-water (from 9:1:0.05 to 7:1:0.05) to give SPK193 in the yield of 41 mg.

Physicochemical properties of SPK193
(1) Melting point: 185°–186° C.,
(2) Specific rotation $[\alpha]_D^{25}=-0.8°$ (c=0.1, in methanol),
(3) Elementary analysis:

|  | C | H | O | N |
|---|---|---|---|---|
| Calculated (%) | 54.78, | 7.51, | 17.03, | 14.91, |
| Found (%) | 55.06, | 7.16, | 16.82, | 15.21, |

(4) FD mass spectrum (m/z): 659 (M+H)$^+$, $C_{30}H_{49}N_7O_7F_2$
(5) Infrared spectrum (KBr disc):
3250 cm$^{-1}$, 1660 cm$^{-1}$, 1620 cm$^{-1}$,
(6) Proton nuclear magnetic resonance spectrum (500 MHz, in CD$_3$OD) $\delta_H$: 0.89 (3H, t, J=7.1 Hz), 1.25–1.60 (20H, m), 2.09 (2H, m), 3.60–3.80 (5H, m), 3.96 (1H, d, J=16.7 Hz), 3.98 (1H, d, J=16.7 Hz), 4.02 (1H, dd, J=2.1, <1 Hz), 4.15 (1H, dd, J=10.4, 10.4 Hz), 5.76 (1H, brs), 8.15 (1H, brs), 8.31 (1H, s).

EXAMPLE 71

Preparation of SPK256

To a solution of (R)-(–)-2-hydroxyhexadecanoic acid (0.5 g; prepared by the method described in Agric. Biol. Chem., 54(12), 3337–3338, 1990) in DMF (20 ml) were added N-hydroxysuccinimide (0.22 g) and N,N'-dicyclohexylcarbodiimide (0.38 g), and the mixture was stirred at room temperature for 12 hours and then filtered. 6-(4'-N-Glycyl-spicaminyl-amino)purine hydrochloride (0.71 g) and triethylamine (1.3 ml) were added to the filtrate, and the mixture was stirred for 12 hours, concentrated and subjected to chromatography on a silica gel column with eluent systems of chloroform-methanol (from 7:1 to 5:1) to give SPK256 in the yield of 108 mg.

Physicochemical properties of SPK256
(1) Melting point: 182°–186° C.,
(2) Specific rotation $[\alpha]_D^{25}=-6°$ (c=0.1, in methanol),
(3) Elementary analysis:

|  | C | H | O | N |
|---|---|---|---|---|
| Calculated (%) | 56.50, | 8.06, | 20.07, | 15.37, |
| Found (%) | 56.83, | 8.12, | 19.91, | 15.14, |

(4) FD mass spectrum (m/z): 638 (M)$^+$, $C_{30}H_{51}N_7O_8$
(5) Infrared spectrum (KBr disc): 3300 cm$^{-1}$, 1630 cm$^{-1}$,
(6) Proton nuclear magnetic resonance spectrum (500 MHz, in CDCl$_3$-CD$_3$OD) $\delta_H$: 0.89 (3H, t, J=7.1 Hz), 1.25–1.55 (24H, m), 1.60–1.90 (2H, m), 3.60–3.82 (5H, m), 3.87 (1H, d, J=16.6 Hz), 4.05 (1H, d, J=16.6 Hz), 4.07 (1H), 4.10 (1H, dd, J=8.6, 3.7 Hz), 4.18 (1H, dd, J=10.6, 10.6 Hz), 5.62 (1H, brs), 8.06 (1H, brs), 8.30 (1H, s).

EXAMPLE 72

Preparation of SPK271

(S)-(+)-2-Acetoxyhexadecanoic acid (0.5 g; prepared by the method described in Agric. Biol. Chem., 54(12), 3337–3338, 1990) was dissolved in a solution of potassium hydroxide (1.0 g) in 50% aqueous ethanol was stirred at 70° C. for 2 hours. After the ethanol was evaporated, the reaction mixture was acidified with citric acid and extracted with ethyl acetate. The ethyl acetate layer was dried and concentrated to give (S)-(–)-2-hydroxyhexadecanoic acid (407 mg). The product was dissolved in DMF (20 ml), and N-hydroxysuccinimide (173 mg) and N,N'-dicyclohexylcarbodiimide (310 mg) were added to the solution. The mixture was stirred at room temperature for 12 hours and then filtered. 6-(4'-N-Glycyl-spicaminyl-amino)purine hydrochloride (0.60 g) and triethylamine (1.0 ml) were added to the filtrate, and the mixture was stirred for 12 hours, concentrated and subjected to chromatography on a silica gel column with eluent systems of chloroform-methanol (from 7:1 to 5:1) to give SPK271 in the yield of 97 mg. Substantially no contamination of the diastereomer was observed.

Physicochemical properties of SPK271
(1) Melting point: 173°–174° C.,
(2) Specific rotation $[\alpha]_D^{25}=-14.4°$ (c=0., in methanol),
(3) Elementary analysis:

|  | C | H | O | N |
|---|---|---|---|---|
| Calculated (%) | 56.50, | 8.06, | 20.07, | 15.37, |
| Found (%) | 56.91, | 7.60, | 19.71, | 15.78, |

(4) FD mass spectrum (m/z): 639 (M+H)$^+$, $C_{30}H_{51}N_7O_8$
(5) Infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 0.89 (3H, t, J=7.1 Hz), 1.22–1.55 (24H, m), 1.55–1.90 (2H, m), 3.60–3.80 (5H, m), 3.90 (1H, d, J=16.6 Hz), 3.97 (1H, d, J=16.6 Hz), 4.01 (1H, d, J=2.1, <1 Hz), 4.06 (1H, dd, J=7.1, 4.0 Hz), 4.14 (1H, dd, J=10.4 Hz), 8.10 (1H, s), 8.30 (1H, s).

EXAMPLE 73

Preparation of SPK270

(R)-(–)-3-Hydroxytetradecanoic acid (0.5 g) was dissolved in DMF (20 ml). N-hydroxysuccinimide (0.26 g) and N,N'-dicyclohexylcarbodiimide (0.46 g) were added to the solution at 0° C., and the mixture, after stirring at room temperature for 12 hours, was filtered. 6-(4'-N-Glycyl-spicaminyl-amino)purine hydrochloride (0.86 g) and triethylamine (1.6 ml) were added to the filtrate, and the mixture was stirred for 12 hours, concentrated and subjected to chromatography on a silica gel column with eluent systems of chloroform-methanol (from 7:1 to 5:1) to give SPK270 in the yield of 121 mg. Physicochemical properties of SPK270
(1) Melting point: 167°–168° C.,
(2) Specific rotation $[\alpha]_D^{25}=-1.2°$ (c=0.1, in methanol),
(3) Elementary analysis:

|  | C | H | O | N |
|---|---|---|---|---|
| Calculated (%) | 55.16, | 7.77, | 20.99, | 16.08, |
| Found (%) | 54.98, | 7.99, | 20.86, | 16.17, |

(4) FD mass spectrum (m/z): 610 (M)$^+$, $C_{28}H_{47}N_7O_8$
(5) Infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 0.89 (3H, t, J=7.1 Hz), 1.20–1.65 (20H, m), 2.33 (1H, dd, J=14.5, 13.0 Hz), 2.44 (1H, dd, J=4.3, 14.5 Hz), 3.60–3.80 (5H, m), 3.82 (1H, d, J=17.0 Hz), 3.97 (1H, d, J=17.0 Hz), 3.99 (1H), 4.02 (1H, m), 4.14 (1H, dd, J=10.4, 10.4 Hz), 5.67 (1H, brs), 8.12 (1H, brs), 8.30 (1H, s).

EXAMPLE 74

Preparation of SPK274

(R)-(+)-3-Hydroxytetradecanoic acid (0.5 g) was dissolved in DMF (20 ml). N-hydroxysuccinimide (0.26 g) and N,N'-dicyclohexylcarbodiimide (0.46 g) were added to the solution at 0° C. and the mixture, after stirring at room temperature for 12 hours, was filtered. 6-(4'-N-Glycyl-spicaminyl-amino)purine hydrochloride (0.86 g) and triethylamine (1.6 ml) were added to the filtrate, and the mixture was stirred for 12 hours, concentrated and subjected to chromatography on a silica gel column with eluent systems of chloroform-methanol (from 7:1 to 5:1) to give SPK274 in the yield of 136 mg.

Physicochemical properties of SPK274

(1) Melting point: 178°–180° C.,
(2) Specific rotation $[\alpha]_D^{25}=-4.4°$ (c=0.1, in methanol),
(3) Elementary analysis:

|  | C | H | O | N |
|---|---|---|---|---|
| Calculated (%) | 55.16, | 7.77, | 20.99, | 16.08, |
| Found (%) | 55.01, | 8.01, | 21.32, | 15.66, |

(4) FD mass spectrum (m/z): 610 (M)$^+$, $C_{28}H_{47}N_7O_8$
(5) Infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 0.89 (3H, t, J=7.1 Hz), 1.20–1.65 (20H, m), 2.33 (1H, dd, J=8.9, 13.9 Hz), 2.45 (1H, dd, J=4.3, 13.9 Hz), 3.60–3.80 (5H, m), 3.85 (1H, d, J=16.1 Hz), 3.87 (1H, d, J=16.1 Hz), 4.02 (1H, dd, J=2.1, <1 Hz), 4.03 (1H, m), 4.14 (1H, dd, J=10.4, 10.4 Hz), 5.67 (1H, brs), 8.14 (1H, brs), 8.30 (1H, s).

EXAMPLE 75

Preparation of SPK252

15-Hydroxypentadecanoic acid (3.0 g) dissolved in a 10% methanolic hydrochloric acid solution was stirred for 1 hour. The reaction mixture was then concentrated, and the residue was distributed into chloroform and water. The ethyl acetate layer was further dried over anhydrous sodium sulfate and concentrated to give the methyl ester of 15-hydroxypentadecanoic acid (3.0 g). To the methyl ester dissolved in pyridine (2.6 ml) was added para-toluenesulfonyl chloride (2.5 g) at 0° C., and the mixture was stirred at room temperature for 18 hours. Then, the reaction mixture was concentrated and distributed into chloroform and water. The chloroform layer was dried and concentrated, and the residue thus obtained was subjected to chromatography on a silica gel column with an eluent system of n-hexane-ethyl acetate (20:1) to give the methyl ester of 15-para-toluenesulfonyloxypentadecanoic acid (3.47 g). To the product (1 g) dissolved in N,N-dimethylformamide (50 ml) was added sodium azide (1.52 g), and the mixture was stirred at 80° C. for 5 hours. The reaction mixture was concentrated and distributed into ethyl acetate and water to give the methyl ester of 15-azidopentadecanoic acid (0.66 g). To the methyl ester was added a solution of potassium hydroxide (0.6 g) in 50% aqueous ethanol (100 ml), and the mixture was stirred at 60° C. for 1 hour. Ethanol was evaporated from the reaction mixture, which is acidified to a weak acidic range of pH and extracted with ethyl acetate. The organic layer was dried and concentrated to give 15-chloropentadecanoic acid ( 0.57 g ). The product was dissolved in N,N-dimethylformamide (DMF, 50 ml), and para-nitrophenol (0.28 g) and N,N'-dicyclohexylcarbodiimide (0.42 g) were added to the solution. The mixture was stirred for 12 hours. Then, precipitates produced were removed by filtration, and 6-(4'-N-glycyl-spicaminyl-amino)purine hydrochloride (700 mg) and triethylamine (2.5 ml) were added to the filtrate. The mixture was stirred for 12 hours. After the solvent was evaporated, the residue was subjected to chromatography on a silica gel column with eluent systems of chloroform-methanol (from 7:1 to 5:1) to give SPK252 in the yield of 193 mg.

Physicochemical properties of SPK252

(1) Melting point: 182°–183° C.,
(2) Specific rotation $[\alpha]_D^{25}=-6°$ (c=0.1, in methanol),
(3) Elementary analysis:

|  | C | H | O | N |
|---|---|---|---|---|
| Calculated (%) | 53.69, | 7.46, | 17.26, | 21.59, |
| Found (%) | 53.41, | 7.52, | 17.15, | 21.92, |

(4) FD mass spectrum (m/z): 650 (M+H)$^+$, $C_{29}H_{48}N_{10}O_7$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.25–1.70 (24H, m), 2.28 (2H, t, J=7.1 Hz), 3.28 (2H, t, J=7.1 Hz), 3.60–3.80 (5H, m), 3.87 (1H, d, J=16.7 Hz), 3.89 (1H, d, J=16.7 Hz), 4.01 (1H, dd, J=2.1, <1 Hz), 4.15 (1H, dd, J=10.4, 10.4 Hz), 5.68 (1H, brs), 8.15 (1H, brs), 8.30 (1H, s).

EXAMPLE 76

Preparation of SPK249

12-Bromododecanoic acid (5 g) dissolved in a 10% methanolic hydrochloric acid solution (30 ml) was stirred at room temperature for 1 hour. The reaction mixture was then concentrated and distributed into chloroform and water, and the chloroform layer was further washed with a 1% aqueous sodium hydrogen carbonate solution and water, dried with anhydrous sodium sulfate and concentrated to give the methyl ester of 12-bromododecanoic acid (5.0 g). To the methyl ester (2.24 g) dissolved in N,N-dimethylformamide (DMF, 30 ml) were added 60% sodium hydride (917 mg) and phenol (720 mg), and the mixture was stirred for 17 hours. Then, the DMF was evaporated and the residue was distributed into chloroform and water. The chloroform layer was dried with anhydrous sodium sulfate, concentrated and subjected to chromatography on a silica gel column with an eluent system of n-hexane-ethyl acetate (10:1) to give the methyl ester of 12-phenoxydodecanoic acid (1.05 g). The product (1.05 g) was dissolved in a 50% aqueous ethanol solution in which potassium hydroxide (920 mg) was dissolved, and the mixture was stirred under heating at 60° C. for 2 hours. Then, the ethanol was evaporated from the reaction mixture, which was acidified to a weak acidic range of pH and extracted with ethyl acetate. The ethyl acetate layer was dried and concentrated to give 12-phenoxydodecanoic acid (850 mg). To this product dissolved in DMF were added para-nitrophenol (404 mg) and N,N'-dicyclohexylcarbodiimide (600 mg), and the mixture was stirred for 15 hours. After precipitates were removed by filtration, 6-(4'-N-glycyl-spicaminyl-amino)purine hydrochloride (250 mg) and triethylamine (1.0 ml) were added to the solution. The mixture was stirred for further 15 hours. After the solvent was evaporated, the residue was subjected to chromatography on a silica gel column with eluent systems of chloroform-methanol (from 7:1 to 5:1) to give SPK249 in the yield of 96 mg.

Physicochemical properties of SPK249
(1) Melting point: 175°–177° C.,
(2) Specific rotation $[\alpha]_D^{24}$=−8.4° (c=0.1, in methanol),
(3) Elementary analysis:

|  | C | H | O | N |
|---|---|---|---|---|
| Calculated (%) | 58.52, | 7.06, | 19.49, | 14.93, |
| Found (%) | 58.88, | 6.82, | 19.18, | 15.12, |

(4) FD mass spectrum (m/z): 658 (M+H)$^+$, $C_{32}H_{46}N_7O_8$
(5) infrared spectrum (KBr disc): 3300 cm$^{-1}$, 1630 cm$^{-1}$,
(6) Proton nuclear magnetic resonance spectrum (500 MHz, in CD$_3$OD) $\delta_H$: 1.30–1.45 (12H, m), 1.48 (2H, m), 1.63 (2H, m), 1.76 (2H, m), 2.28 (2H, t, J=7.1 Hz), 3.60–3.80 (5H, m), 3.87 (1H, d, J=16.7 Hz), 3.89 (1H, d, J=16.7 Hz), 3.95 (2H, t, J=7.1 Hz), 4.01 (1H, dd, J=2.1, <1 Hz), 4.14 (1H, t, J=10.4, 10.4 Hz), 5.68 (1H, brs), 6.87 (3H, m), 7.24 (2H, t, J=7.6 Hz), 8.15 (1H, brs), 8.32 (1H, s).

EXAMPLE 77

Preparation of SPK242

To 2-bromododecanoic acid (500 mg) dissolved in N,N-dimethylformamide (DMF, 10 ml) at 0° C. were added 60% sodium hydride (163 mg) followed by phenol (154 mg), and the mixture was stirred for 17 hours. Then, the solvent (DMF) was evaporated, and the residue was distributed into water and ethyl acetate. The ethyl acetate layer was dried and concentrated to give 2-phenoxydodecanoic acid (440 mg). To 2-phenoxydodecanoic acid (440 mg) dissolved in DMF were added para-nitrophenol (190 mg) and N,N'-dicyclohexylcarbodiimide (283 mg), and the mixture was stirred for 15 hours. Then, precipitates produced were removed by filtration, and 6-(4'-N-glycyl-spicaminyl-amino)purine hydrochloride (529 mg) and triethylamine (2.0 ml) were added to the filtrate. The mixture was further stirred for 15 hours. The DMF was evaporated from the reaction mixture, and the residue was subjected to chromatography on a silica gel column with eluent systems of chloroform-methanol (from 7:1 to 5:1) to give SPK242 in the yield of 118 mg.

Physicochemical properties of SPK242
(1) Melting point: 172°–174° C.,
(2) Elementary analysis:

|  | C | H | O | N |
|---|---|---|---|---|
| Calculated (%) | 59.55, | 7.50, | 18.66, | 14.30, |
| Found (%) | 59.30, | 7.78, | 18.91, | 14.01, |

(3) FD mass spectrum (m/z): 686 (M)$^+$, $C_{34}H_{51}N_7O_8$
(4) Infrared spectrum (KBr disc): 3300 cm$^{-1}$, 1660 cm$^{-1}$, 1620 cm$^{-1}$,
(5) Proton nuclear magnetic resonance spectrum (500 MHz, in CD$_3$OD) $\delta_H$: 0.89 (3H, t, J=7.1 Hz), 1.20–1.60 (20H, m), 1.92 (2H, m), 3.67–3.82 (5H, m), 3.85–4.04 (2H), 4.05 (1H, dd, J=2.1, <1 Hz), 4.15 (1H, dd, J=10.0, 10.0 Hz), 4.62 (1H, m), 5.67 (1H, brs), 6.95–7.05 (3H, m), 7.32 (2H), 8.01 (1H, brs), 8.22 (1H, s).

EXAMPLE 78

Preparation of SPK197

To (S)-(+)-2-acetoxyhexadecanoic acid (0.5 g; prepared according to the method described in Agric. Biol. Chem., 54(12), 3337–3338, 1990) dissolved in DMF were (20 ml) were added N-hydroxysuccinimide (183 mg) and N,N'-dicyclohexylcarbodiimide (328 mg) at 0° C., and the mixture was stirred at room temperature for 12 hours. The reaction mixture was then filtered, and 6-(4'-N-glycyl-spicaminyl-amino)purine hydrochloride (0.62 g) and triethylamine (1.1 ml) were added to the filtrate. The mixture was stirred for 12 hours. After the reaction mixture was concentrated, the residue was subjected to chromatography on a silica gel column with eluent systems of chloroform-methanol (from 7:1 to 5:1) to give SPK197 in the yield of 107 mg. Substantially no contamination of the diastereomer was observed.

Physicochemical properties of SPK197
(1) Melting point: 181°–183° C.,
(2) Specific rotation $[\alpha]_D^{25}$=+13.2° (c=0.1, in methanol),
(3) Elementary analysis:

|  | C | H | O | N |
|---|---|---|---|---|
| Calculated (%) | 56.54, | 7.86, | 21.18, | 14.42, |
| Found (%) | 56.30, | 8.09, | 21.33, | 14.28, |

(4) FD mass spectrum (m/z): 680 (M)$^+$, $C_{32}H_{53}N_7O_9$
(5) Infrared spectrum (KBr disc): 3350 cm$^{-1}$, 1720 cm$^{-1}$, 1660 cm$^{-1}$, 1620 cm$^{-1}$,
(6) Proton nuclear magnetic resonance spectrum (500 MHz, in CD$_3$OD) $\delta_H$: 0.89 (3H, t, J=7.1 Hz), 1.20–1.50 (24H, m), 1.82 (2H, m), 2.20 (3H, s), 3.60–3.80 (5H, m), 3.86 (1H, d, 16.8 Hz), 3.95 (1H, d, 16.8 Hz), 4.01 (1H, dd, J=2.1, <1 Hz), 4.15 (1H, dd, J=10.4, 10.4 Hz), 4.96 (1H, t, J=6.4 Hz), 5.68 (1H, brs), 8.15 (1H, s), 8.30 (1H, s).

EXAMPLE 79

Preparation of SPK198

To (R)-(+)-2-hydroxyhexadecanoic acid (0.5 g; prepared according to the method described in Agric. Biol. Chem., 54(12), 3337–3338, 1990) dissolved in pyridine (15 ml) was added acetic anhydride (0.23 ml) at 0° C., and the mixture was stirred 12 hours. The reaction mixture was distributed into ethyl acetate and water, and the ethyl acetate layer was dried and concentrated to give (R)-(−)-2-acetoxyhexadecanoic acid (0.52 g). The acetoxy derivative was dissolved in DMF (20 ml), and N-hydroxysuccinimide (191 mg) and N,N'-dicyclohexylcarbodiimide (342 mg) were added to the solution at 0° C. The mixture was stirred at room temperature for 12 hours. The reaction mixture was then filtered, and 6-(4'-N-glycyl-spicaminyl-amino)purine hydrochloride (0.65 g) and triethylamine (1.1 ml) were added to the filtrate. The mixture was stirred for 12 hours. After the reaction mixture was concentrated, the residue was subjected to chromatography on a silica gel column with eluent systems of chloroform-methanol (from 7:1 to 5:1) to give SPK198 in the yield of 119 mg.

Physicochemical properties of SPK198
(1) Melting point: 184°–185° C.,
(2) Specific rotation $[\alpha]_D^{25}$=−26.0° (c=0.1, in methanol),
(3) Elementary analysis:

|  | C | H | O | N |
|---|---|---|---|---|
| Calculated (%) | 56.54, | 7.86, | 21.18, | 14.42, |
| Found (%) | 56.21, | 8.13, | 21.26, | 14.40, |

(4) FD mass spectrum (m/z): 680 (M)$^+$, $C_{32}H_{53}N_7O_9$ (5) Infrared spectrum (KBr disc): 3300 cm$^{-1}$, 1720 cm$^{-1}$, 1660 cm$^{-1}$, 1620 cm$^{-1}$, (6) Proton nuclear magnetic resonance spectrum (500 MHz, in CDCl$_3$-CD$_3$OD) $\delta_H$: 0.90 (3H, t, J=7.1 Hz), 1.25–1.60 (24H, m), 1.84 (2H, m), 2.18 (3H, s), 3.60–3.80 (5H, m), 3.89 (1H, d, J=17.3 Hz), 3.92 (1H, d, J=17.3 Hz), 4.02 (1H, dd, J=2.1, <1 Hz), 4.15 (1H, dd, J=10.4, 10.4 Hz), 4.98 (1H, t, J=6.9 Hz), 5.66 (1H, brs), 8.12 (1H, brs), 8.30 (1H, s).

EXAMPLE 80

Preparation of SPK262

2-Bromothiophene (0.82 g) and bis(triphenylphosphine)palladium (II) chloride (35 mg) were mixed with stirring in triethylamine (35 ml). Copper (I) iodide (5 mg) was added to this mixture. After the mixture was stirred for 15 minutes, 10-undecynoic acid (0.91 g) was further added thereto, and resulting mixture, after stirring for 12 hours, was filtered and concentrated. The residue was subjected to chromatography on a silica gel column with an eluent system of chloroform-methanol (100:1) to give 11-(2'-thienyl)-10-undecynoic acid (0.30 g).

To 11-(2'-thienyl)-10-undecynoic acid (234 mg) dissolved in N,N-dimethylformamide (DMF, 12 ml) were added N-hydroxysuccinimide (102 mg) and N,N'-dicyclohexylcarbodiimide (183 mg), and the mixture was stirred for 12 hours. After precipitates produced were removed by filtration, the filtrate was added to a solution of 6-(4'-N-glycyl-spicaminyl-amino)purine hydrochloride (450 mg) and triethylamine (1.6 ml) in DMF (45 ml), and the mixture was stirred for 12 hours. The solvent was evaporated, and the residue was subjected to chromatography on a silica gel column with eluent systems of chloroform-methanol-water (from 7:1:0.05 to 5:1:0.1) to give SPK262 in the yield of 151 mg.

Physicochemical properties of SPK262

(1) Melting point: 184°–186° C., (2) Specific rotation $[\alpha]_D^{25}$=–4.8° (c=0.1, in methanol), (3) Elementary analysis:

|  | C | H | O | N |
|---|---|---|---|---|
| Calculated (%) | 55.31, | 6.24, | 17.79, | 15.57, |
| Found (%) | 55.25, | 5.95, | 17.58, | 15.82, |

(4) FD mass spectrum (m/z): 630 (M)$^+$, $C_{29}H_{39}N_7O_7S$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.30–1.70 (12H, m), 2.28 (2H, t, J=7.6 Hz), 2.43 (2H, t, J=7.6 Hz), 3.60–3.80 (5H, m), 3.87 (1H, d, J=16.1 Hz), 3.89 (1H, d, J=16.1 Hz), 4.01 (1H, dd, J=2.1, <1 Hz), 4.14 (1H, dd, J=10.4, 10.4 Hz), 5.67 (1H, brs), 6.93 (1H, dd, J=3.6, 3.6 Hz), 7.07 (1H, dd, J=3.6, <1 Hz), 7.27 (1H, dd, J=3.6, <1 Hz), 8.15 (1H, s), 8.31 (1H, s).

EXAMPLE 81

Preparation of SPK263

3-Bromothiophene (0.82 g) and bis(triphenylphosphine)palladium (II) chloride (35 mg) were mixed with stirring in triethylamine (35 ml). Copper (I) iodide (5 mg) was added to this mixture. After the mixture was stirred for 15 minutes, 10-undecynoic acid (0.91 g) was further added thereto, and resulting mixture, after stirring for 12 hours, was filtered and concentrated. The residue was subjected to chromatography on a silica gel column with eluent systems of chloroform-methanol (100:1) to give 11-(3'-thienyl)-10-undecynoic acid (0.17 g).

To 11-(3'-thienyl)-10-undecynoic acid (0.17 g) dissolved in N,N-dimethylformamide (DMF, 8.5 ml) were added N-hydroxysuccinimide (74 mg) and N,N'-dicyclohexylcarbodiimide (133 mg), and the mixture was stirred for 12 hours. After precipitates produced were removed by filtration, the filtrate was added to a solution of 6-(4'-N-glycyl-spicaminyl-amino)purine hydrochloride (300 mg) and triethylamine (1.1 ml) in DMF (30 ml), and the mixture was stirred for 12 hours. The solvent was evaporated, and the residue was subjected to chromatography on a silica gel column with eluent systems of chloroform-methanol-water (from 7:1:0.05 to 5:1:0.1) to give SPK263 in the yield of 160 mg.

Physicochemical properties of SPK263

(1) Melting point: 180°–181° C., (2) Specific rotation $[\alpha]_D^{25}$=+2.4° (c=0.1, in methanol), (3) Elementary analysis:

|  | C | H | O | N |
|---|---|---|---|---|
| Calculated (%) | 55.31, | 6.24, | 17.79, | 15.57, |
| Found (%) | 55.62, | 5.88, | 17.62, | 15.78, |

(4) FD mass spectrum (m/z): 652 (M+Na)$^+$, $C_{29}H_{39}N_7O_7S$ (5) Infrared spectrum (KBr disc): 3300 cm$^{-1}$, 1630 cm$^{-1}$, (6) Proton nuclear magnetic resonance spectrum (500 MHz, in CD$_3$OD) $\delta_H$: 1.30–1.70 (12H, m), 2.28 (2H, t, J=7.1 Hz), 2.38 (2H, t, J=7.1 Hz), 3.60–3.80 (5H, m), 3.87 (1H, d, J=16.1 Hz), 3.89 (1H, d, J=16.1 Hz), 4.02 (1H, dd, J=2.1, <1 Hz), 4.15 (1H, t, J=10.4 Hz), 5.69 (1H, brs), 7.02 (1H, dd, J=1.3, 4.7 Hz), 7.32 (1H, dd, J=3.3, 4.7 Hz), 7.37 (1H, dd, J=1.3, 3.3 Hz), 8.13 (1H, s), 8.29 (1H, s).

EXAMPLE 82

Preparation of SPK266

3-Bromofuran (0.82 g) and bis(triphenylphosphine)-palladium (II) chloride (35 mg) were mixed with stirring in triethylamine (35 ml). Copper (I) iodide (5 mg) was added to this mixture. After the mixture was stirred for 15 minutes, 10-undecynoic acid (0.91 g) was further added thereto, and resulting mixture, after stirring for 12 hours, was filtered and concentrated. The residue was subjected to chromatography on a silica gel column with eluent system of chloroform to chloroform-methanol (100:1) to give 11-(3'-furyl)-10-undecynoic acid (0.16 g).

To 11-(3'-furyl)-10-undecynoic acid (0.17 g) dissolved in N,N-dimethylformamide (DMF, 8 ml) were added N-hydroxysuccinimide (74 mg) and N,N'-dicyclohexylcarbodiimide (133 mg), and the mixture was stirred for 12 hours. After precipitates produced were removed by filtration, the filtrate was added to a solution of 6-(4'-N-glycyl-spicaminyl-amino)purine hydrochloride (300 mg) and triethylamine (1.1 ml) in DMF (30 ml), and the mixture was stirred for 12 hours. The solvent was evaporated, and the residue was subjected to chromatography on a silica gel column with eluent systems of chloroform-methanol-water (from 7:1:0.05 to 5:1:0.1) to give SPK266 in the yield of 93 mg.

Physicochemical properties of SPK266
(1) Melting point: 161°–162° C.,
(2) Specific rotation $[\alpha]_D^{25}$=+1.2° (c=0.1, in methanol),
(3) Elementary analysis:

|  | C | H | O | N |
|---|---|---|---|---|
| Calculated (%) | 56.76, | 6.41, | 20.86, | 15.98, |
| Found (%) | 57.05, | 6.42, | 20.80, | 15.83, |

(4) FD mass spectrum (m/z): 614 (M)$^+$, $C_{29}H_{39}N_7O_8$
(5) Infrared spectrum (KBr disc): 3300 cm$^{-1}$, 1620 cm$^{-1}$,
(6) Proton nuclear magnetic resonance spectrum (500 MHz, in CD$_3$OD) $\delta_H$: 1.30–1.70 (12H, m), 2.28 (2H, t, J=7.1 Hz), 2.37 (2H, t, J=7.1 Hz), 3.60–3.80 (5H, m), 3.87 (1H, d, J=16.1 Hz), 3.89 (1H, d, J=16.1 Hz), 4.01 (1H, dd, J=2.1, <1 Hz), 4.15 (1H, dd, J=10.4, 10.4 Hz), 5.67 (1H, brs), 6.38 (1H, d, J=1.4 Hz), 7.42 (1H, dd, J=1.4, <1 Hz), 7.58 (1H, dd, J=<1 Hz), 8.12 (1H, brs), 8.28 (1H, s).

EXAMPLE 83

Preparation of SPT152

To a solution of 12-bromododecanoic acid (1 g) and para-nitrophenol (490 mg) in N,N-dimethylformamide (DMF, 30 ml) was added N,N'-dicyclohexylcarbodiimide (740 mg), and the mixture was stirred for 12 hours. The reaction mixture was filtered and concentrated to give the active ester of 12-bromododecanoic acid. To this active ester (836 mg) dissolved in DMF were added 6-(4'-N-glycyl-septaminyl-amino)purine hydrobromide (800 mg) and triethylamine (2.5 ml), and the mixture was stirred for hours. The solvent was evaporated, and the residue was subjected to chromatography on a silica gel column with eluent systems of chloroform-methanol (from 7:1 to 5:1) to give SPK152 in the yield of 462 mg.
Physicochemical properties of SPK152
(1) Melting point: 155°–157° C.,
(2) Specific rotation $[\alpha]_D^{25}$=+9.2° (c=0.1, in methanol),
(3) Elementary analysis:

|  | C | H | O | N |
|---|---|---|---|---|
| Calculated (%) | 52.04, | 7.05, | 18.66, | 16.34, |
| Found (%) | 52.30, | 6.79, | 18.45, | 16.49, |

(4) FD mass spectrum (m/z): 644, 646 (M+H)$^+$, $C_{26}H_{42}N_7O_7Br$
(5) Infrared spectrum (KBr disc): 3400 cm$^{-1}$, 1630 cm$^{-1}$,
(6) Proton nuclear magnetic resonance spectrum (500 MHz, in CD$_3$OD) $\delta_H$: 1.20–1.70 (18H, m), 1.84 (2H, m), 2.28 (2H, t, J=7.0 Hz), 3.43 (2H, t, J=7.1 Hz), 3.50–3.80 (6H, m), 3.86 (1H, d, J=15.1 Hz), 3.89 (1H, d, J=15.1 Hz), 3.90 (1H, dd, J=10.1, 10.1 Hz), 5.43 (1H, brs), 8.12 (1H, s), 8.31 (1H, s).

EXAMPLE 84

Preparation of SPT241

To a solution of trans-2-dodecenal (4.5 g) dissolved in methylene chloride (80 ml) was added (carbomethoxymethylene)triphenylphosphorane (8.3 g), and the mixture was stirred for 2 hours. The reaction mixture was subjected to chromatography on a silica gel column with eluent systems of n-hexane-ethyl acetate (from 100:1 to 20:1) to give the methyl ester of trans,trans-2,4-tetradecadienoic acid (5.4 g). To a solution of potassium hydroxide (6.5 g) in a mixed solvent of ethanol-water (1:1) (100 ml) was added the methyl ester of trans,trans-2,4-tetradecadienoic acid (5.4 g), and the mixture was stirred at 60° C. for 40 minutes. The reaction mixture was cooled, and acidified to a weak acidic range of pH with citric acid and extracted with ethyl acetate. The ethyl acetate layer was dried over anhydrous sodium sulfate and concentrated to give trans,trans-2,4-tetradecadienoic acid (4.3 g). To the tetradecadienoic acid dissolved in N,N-dimethylformamide (DMF, 50 ml) was added para-nitrophenol (2.67 g) and N,N'-dicyclohexylcarbodiimide (3.9 g), and the mixture was stirred for 12 hours. After precipitates produced were removed by filtration and DMF was evaporated, the residue was subjected to chromatography on a silica gel column with eluent systems of n-hexane-ethyl acetate (from 200:1 to 50:1) to give the active ester of trans,trans-2,4-tetradecadienoic acid (5.1 g). To the active ester (500 mg) dissolved in DMF (30 ml) were added 6-(4'-N-glycyl-septaminyl-amino)purine hydrochloride (560 mg) and triethylamine (1.5 ml), and the mixture was stirred for 18 hours. The solvent was evaporated, and the residue was subjected to chromatography on a silica gel column with eluent systems of chloroform-methanol (from 7:1 to 5:1) to give SPT241 in the yield of 271 mg.
Physicochemical properties of SPT241
(1) Melting point: 154°–156° C.,
(2) Specific rotation $[\alpha]_D^{25}$=−16.0° (c=0.1, in methanol),
(3) Elementary analysis:

|  | C | H | O | N |
|---|---|---|---|---|
| Calculated (%) | 57.03, | 7.35, | 18.99, | 16.63, |
| Found (%) | 56.82, | 7.63, | 19.15, | 16.40, |

(4) FD mass spectrum (m/z): 590 (M+H)$^+$, $C_{28}H_{43}N_7O_7$
(5) Infrared spectrum (KBr disc): 3250 cm$^{-1}$, 1650 cm$^{-1}$, 1620 cm$^{-1}$,
(6) Proton nuclear magnetic resonance spectrum (500 MHz, in CD$_3$OD) $\delta_H$: 0.89 (3H, t, J=7.1 Hz), 1.20–1.50 (14H, m), 2.19 (2H, dt, J=7.1 Hz), 3.53 (1H, dd, J=9.5, 9.5 Hz), 3.60–3.80 (6H, m), 3.95 (1H, dd, J=10.0, 10.0 Hz), 3.97 (2H, s), 5.98 (1H, d, J=15.0 Hz), 6.14 (1H, dt, J=15.0, 7.3 Hz), 6.21 (1H, dd, J=15.0, 10.5 Hz), 7.18 (1H, dd, 10.5, 15.0 Hz), 8.07 (1H, s), 8.32 (1H, s).

EXAMPLE 85

Process for preparing a sodium salt of the compound of the present invention

To a suspension of the compound of the present invention (10 mg) in methanol (10 ml) are added sodium methoxide (2.3 mg), and the mixture are stirred for 1 hour. Then, the methanol is evaporated to give a sodium salt of the compound of the present invention (10 mg).

EXAMPLE 86

(injection/vial)

| Compound of the present invention | 1–5 mg |
|---|---|
| Ethanol | 1 ml |
| Polysorbate | 0.1 ml |
| Physiological saline | q.s. |
| Total | 10 ml |

The above-specified compounds are mixed together, filtered and filled into a vial as an injection.

EXAMPLE 87

(injection/vial)

| | |
|---|---|
| Compound of the present invention | 5 mg |
| Propylene glycol + Ethanol (1:1 mixture) | 0.5 ml |
| Polysorbate 80 | 0.3 ml |
| Ethanolamine | 40 µl |
| Physiological saline | q.s. |
| Total | 100 ml |

The above-specified compounds are mixed together, filtered and filled into a vial as an injection.

EXAMPLE 88

(injection/vial)

| | |
|---|---|
| Compound of the present invention | 5 mg |
| Dimethylacetamide | 0.25 ml |
| Polysorbate 80 | 0.3 ml |
| 1 N aqueous NaOH | 60 µl |
| Physiological saline | q.s. |
| Total | 100 ml |

The above-specified compounds are mixed together, filtered and filled into a vial as an injection.

EXAMPLE 89

(tablet/1 tablet)

| | |
|---|---|
| Compound of the present invention | 5 mg |
| Crystalline cellulose | 72.5 mg |
| Corn starch | 18 mg |
| Talc | 4 mg |
| Magnesium stearate | 0.5 mg |
| Total | 100 mg |

The above-specified components are mixed and pressed to make a tablet.

What is claimed is:

1. A method of treating cancer comprising administering to a patient in need of such treatment an effective amount of a spicamycin derivative represented by the formula (I) or a salt thereof:

(I)

wherein $R_1$ and $R_2$ are different from each other and each represents H or OH and R represents any one of the substituents (1)–(16):

(1) a linear alkenyl having 11–13 carbon atoms;
(2) a linear alkyl having 12–13 carbon atoms, and a branched alkyl having 11–13 carbon atoms when $R_1$ represents H and $R_2$ represents OH;
(3) a linear haloalkyl having 10–15 carbon atoms;
(4) $CH_3(CH_2)_n CH(OH)-$ of $CH_3(CH_2)_{n-1}CH(OH)-CH_2-$, wherein n denotes an integer of 9–13;
(5) an alkyl having 10–15 carbon atoms with an azide group or a cyano group;
(6) a linear alkyl having 10–13 carbon atoms with a phenoxy group or a halogen-substituted phenoxy group;

(7)

$$CH_3(CH_2)_a \underset{\underset{O}{\|}}{C} O(CH_2)_b-,$$

wherein a denotes an integer of 0–2 and b denotes an integer of 10–15;

(8)

$$CH_3(CH_2)_{b-1}CH- \\ | \\ OC(CH_2)_a CH_3 \\ \| \\ O$$

wherein a denotes an integer of 0–2 and b denotes an integer of 10–15;

(9)

$$CH_3(CH_2)_{b-2}CHCH_2-, \\ | \\ OC(CH_2)_a CH_3 \\ \| \\ O$$

wherein a denotes an integer of 0–2 and b denotes an integer of 10–15;

(10) $CH_3(CH_2)_c SO_2 O(CH_2)_d-$ wherein c denotes an integer of 0–3 and d denotes an integer of 10–15, (11)

$$CH_3(CH_2)_{d-1}CH- \\ | \\ OSO_2(CH_2)_c CH_3$$

wherein c denotes an integer of 0–3 and d denotes an integer of 10–15;

(12) $(CH_3)_3Si(CH_2)_{10}-$ or $(CH_3)_3Si-C\!\!\equiv\!\!C-(CH_2)_8$, (13)

$$CH_3(CH_2)_7 C\ H\ C\ H(CH_2)_7- \\ | \quad | \\ O \quad O \\ \diagdown \diagup \\ H_3C \quad CH_3$$

(14)

$$CH_3(CH_2)_5 \underset{\underset{O}{\|}}{C}(CH_2)_{10}-$$

(15)

wherein X represents O or S and

(16) a linear alkadienyl having 11–13 carbon atoms.

2. A method of treating cancer according to claim 1, wherein the cancer is colon cancer.

3. A method of treating cancer comprising administering to a patient in need of such treatment an effective amount of a spicamycin derivative which is selected from the group consisting of the following compounds:

6-[4'-N-(N'-tridecanoylglycyl)spicaminyl-amino]purine (SPM 9),

6-[4'-N-(N'-tetradecanoylglycyl)spicaminyl-amino]purine (SPM 10),

6-[4'-N-(N'-10-methylundecanoylglycyl)spicaminyl-amino]purine (SPK 9),

6-[4'-N-(N'-11-methyldodecanoylglycyl)spicaminyl-amino]purine (SPK 251),

6-[4'-N-(N'-12-methyltridecanoylglycyl)spicaminyl-amino]purine (SPK 136),

6-[4'-N-(N'-11-dodecenoylglycyl)spicaminyl-amino]purine (SPK 44),

6-[4'-N-(N'-12-tridecenoylglycyl)spicaminyl-amino]purine (SPK 142),

6-[4'-N-(N'-cis-9-tetradecenoylglycyl)spicaminyl-amino]purine (SPK 231),

6-[4'-N-(N'-cis-9-hexadecenoylglycyl)spicaminyl-amino]purine (SPK 148),

6-[4'-N-(N'-trans-2-dodecenoylglycyl)spicaminyl-amino]purine (SPK 86),

6-[4'-N-(N'-trans-2-tetradecenoylglycyl)spicaminyl-amino]purine (SPK 156),

6-[4'-N-(N'-trans-2-hexadecenoylglycyl)spicaminyl-amino]purine (SPK 188),

6-[4'-N-(N'-trans,trans-2,4-dodecadienoyl-glycyl)spicaminyl-amino]purine (SPK 282), 6-[4'-N-(N'-trans,trans-2,4-tridecadienoyl-glycyl)spicaminyl-amino]purine (SPK 281), 6-[4'-N-(N'-trans,trans-2,4-tetradecadienoyl-glycyl)spicaminyl-amino]purine (SPK 241), 6-[4'-N-(N'-11-bromoundecanoylglycyl)spicaminyl-amino]purine (SPK 64), 6-[4'-N-(N'-12-bromododecanoylglycyl)spicaminyl-amino]purine (SPK 152), 6-[4'-N-(N'-13-bromotridecanoylglycyl)spicaminyl-amino]purine (SPK 276), 6-[4'-N-(N'-14-bromotetradecanoylglycyl)spicaminyl-amino]purine (SPK 273), 6-[4'-N-(N'-12-chlorododecanoylglycyl)spicaminyl-amino]purine (SPK 132), 6-[4'-N-(N'-13-chlorotridecanoylglycyl)spicaminyl-amino)purine (SPK 278), 6-[4'-N-(N'-14-chlorotetradecanoylglycyl)spicaminyl-amino]purine (SPK 280), 6-[4'-N-(N'-14-fluorotetradecanoylglycyl)spicaminyl-amino]purine (SPK 279), 6-[4'-N-(N'-15-fluoropentadecanoylglycyl)spicaminyl-amino]purine (SPK 247), 6-[4'-N-(N'-16-fluorohexadecanoylglycyl)spicaminyl-amino]purine (SPK 157), 6-[4'-N-(N'-11-iodoundecanoylglycyl)spicaminyl-amino]purine (SPK 165), 6-[4'-N-(N'-2-chlorohexadecanoylglycyl)spicaminyl-amino]purine (SPK 135), 6-[4'-N-(N'-2-fluorododecanoylglycyl)spicaminyl-amino]purine (SPK 159), 6-[4'-N-(N'-2-fluorohexadecanoylglycyl)spicaminyl-amino]purine (SPK 233), 6-[4'-N-(N'-2,2-difluorotetradecanoylglycyl)-spicaminyl-amino]purine (SPK 182), 6-[4'-N-(N'-2-hydroxyhexadecanoylglycyl)spicaminyl-amino]purine (SPK 112), 6-[4'-N-(N'-(S)-2-hydroxyhexadecanoylglycyl)-spicaminyl-amino]purine (SPK 271), 6-[4'-N-(N'-(R)-3-hydroxytetradecanoylglycyl)-spicaminyl-amino]purine (SPK 270), 6-[4'-N-(N'-(S)-3-hydroxytetradecanoylglycyl)-spicaminyl-amino]purine (SPK 274), 6-[4'-N-(N'-3-hydroxyhexadecanoylglycyl)-spicaminyl-amino]purine (SPK 115), 6-[4'-N-(N'-16-cyanohexadecanoylglycyl)-spicaminyl-amino]purine (SPK 177), 6-[4'-N-(N'-11-phenoxyundecanoylglycyl)-spicaminyl-amino]purine (SPK 422), 6-[4'-N-(N'-12-phenoxydodecanoylglycyl)-spicaminyl-amino]purine (SPK 249), 6-[4'-N-(N'-(R)-2-acetoxyhexadecanoylglycyl)-spicaminyl-amino]purine (SPK 198), 6-[4'-N-(N'-3-acetoxyhexadecanoylglycyl)-spicaminyl-amino]purine (SPK 189), 6-[4'-N-(N'-12-butanesulfonyloxydodecanoylglycyl)-spicaminyl-amino]purine (SPK 232), 6-{4'-N-[N'-11-(2'-thienyl)-10-undecynoylglycyl]-spicaminyl-amino}purine (SPK 262), 6-{4'-N-[N'-11-(3'-thienyl)-10-undecynoylglycyl]-spicaminyl-amino}purine (SPK 263), and 6-{4'-N-[N'-11-(3'-furyl)-10-undecynoylglycyl]-spicaminyl-amino}purine (SPK 266).

4. A method of treating cancer according to claim 3, wherein the cancer is colon cancer.

5. A method of treating cancer according to claim 3 wherein the spicamycin derivative is selected from the group consisting of the following compounds:

6-[4'-N-(N'-tridecanoylglycyl)spicaminyl-amino]purine (SPM 9),

6-[4'-N-(N'-11-methyldodecanoylglycyl)spicaminyl-amino]purine (SPK 251),

6-[4'-N-(N'-cis-9-tetradecenoylglycyl)spicaminyl-amino]purine (SPK 231),

6-[4'-N-(N'-trans,trans-2,4-dodecadienoyl-glycyl)spicaminyl-amino]purine (SPK 282), 6-[4'-N-(N'-trans,trans-2,4-tridecadienoyl-glycyl)spicaminyl-amino]purine (SPK 281), 6-[4'-N-(N'-trans,trans-2,4-tetradecadienoyl-glycyl)spicaminyl-amino]purine (SPK 241), 6-[4'-N-(N'-12-bromododecanoylglycyl)spicaminyl-amino]purine (SPK 152), 6-[4'-N-(N'-13-bromotridecanoylglycyl)spicaminyl-amino]purine (SPK 276), 6-[4'-N-(N'-14-bromotetradecanoylglycyl)spicaminyl-amino]purine (SPK 273), 6-[4'-N-(N'-13-chlorotridecanoylglycyl)spicaminyl-amino]purine (SPK 278), 6-[4'-N-(N'-14-chlorotetradecanoylglycyl)spicaminyl-amino]purine (SPK 280), 6-[4'-N-(N'-14-fluorotetradecanoylglycyl)spicaminyl-amino]purine (SPK 279), 6-[4'-N-(N'15-fluoropentadecanoyl-glycyl)spicaminyl-amino]purine (SPK 247), 6-[4'-N-(N'-2,2-difluorotetradecanoylglycyl)-spicaminyl-amino]purine (SPK 182), 6-[4'-N-(N'-(S)-2-hydroxyhexadecanoylglycyl)-spicaminyl-amino]purine (SPK 271), 6-{4'-N-[N'-11-(3'-thienyl)-10-undecynoylglycyl]-spicaminyl-amino}purine (SPK 263) and 6-{4'-N-[N'-11-(3'-furyl)-10-undecynoylglycyl]-spicaminyl-amino}purine (SPK266).

6. A method of treating cancer according to claim 5 wherein the spicamycin derivative is selected from the group consisting of the following compounds:

6-[4'-N-(N'-tridecanoylglycyl)spicaminyl-amino]purine (SPM 9),

6-[4'-N-(N'-11-methyldodecanoylglycyl)spicaminyl-amino]purine (SPK 251),
6-[4'-N-(N'-cis-9-tetradecenoylglycyl)spicaminyl-amino]purine (SPK 231),
6-[4'-N-(N'-trans,trans-2,4-dodecadienoyl-glycyl)spicaminyl-amino]purine (SPK 282),
6-[4'-N-(N'-trans,trans-2,4-tridecadienoyl-glycyl)spicaminyl-amino]purine (SPK 281),
6-[4'-N-(N'-trans,trans-2,4-tetradecadienoyl-glycyl)spicaminyl-amino]purine (SPK 241),
6-[4'-N-(N'-12-bromododecanoylglycyl)spicaminyl-amino]purine (SPK 152),
6-[4'-N-(N'-13-bromotridecanoylglycyl)spicaminyl-amino]purine (SPK 276),
6-[4'-N-(N'-14-bromotetradecanoylglycyl)spicaminyl-amino]purine (SPK 273),
6-[4'-N-(N'-13-chlorotridecanoylglycyl)spicaminyl-amino]purine (SPK 278),
6-[4'-N-(N'-14-chlorotetradecanoylglycyl)spicaminyl-amino]purine (SPK 280),
6-[4'-N-(N'-14-fluorotetradecanoylglycyl)spicaminyl-amino]purine (SPK 279),
6-[4'-N-(N'-15-fluoropentadecanoylglycyl)spicaminyl-amino]purine (SPK 247),
6-[4'-N-(N'-2,2-difluorotetradecanoylglycyl)-spicaminyl-amino]purine (SPK 182),
6-[4'-N-(N'-(S)-2-hydroxyhexadecanoylglycyl)-spicaminyl-amino]purine (SPK 271),
6-{4'-N-[N'-11-(3'-thienyl)-10-undecynoylglycyl]-spicaminyl-amino}purine (SPK 263) and
6-{4'-N-[N'-11-(3'-furyl)-10-undecynoylglycyl]-spicaminyl-amino}purine (SPK 266).

7. A method of treating cancer according to claim 5 wherein the spicamycin derivative is selected from the group consisting of the following compounds:
6-[4'-N-(N'-11-methyldodecanoylglycyl)spicaminyl-amino]purine (SPK 251),
6-[4'-N-(N'-trans,trans-2,4-dodecadienoylglycyl)-spicaminyl-amino]purine (SPK 282),
6-[4'-N-(N'-trans,trans-2,4-tridecadienoylglycyl)-spicaminyl-amino]purine (SPK 281),
6-[4'-N-(N'-trans,trans-2,4-tetradecadienoylglycyl)-spicaminyl-amino]purine (SPK 241),
6-[4'-N-(N'-12-bromododecanoylglycyl)spicaminyl-amino]purine (SPK 152),
6-[4'-N-(N'-13-bromotridecanoylglycyl)spicaminyl-amino]purine (SPK 276),
6-[4'-N-(N'-14-bromotetradecanoylglycyl)spicaminyl-amino]purine (SPK 273),
6-[4'-N-(N'-13-chlorotridecanoylglycyl)spicaminyl-amino]purine (SPK 278),
6-[4'-N-(N'-14-chlorotetradecanoylglycyl)spicaminyl-amino]purine (SPK 280),
6-[4'-N-(N'-14-fluorotetradecanoylglycyl)spicaminyl-amino]purine (SPK 279),
6-[4'-N-(N'-15-fluoropentadecanoylglycyl)spicaminyl-amino]purine (SPK 247),
6-[4'-N-(N'-2,2-difluorotetradecanoylglycyl) spicaminyl-amino]purine (SPK 182),
6-[4'-N-(N'-(S)-2-hydroxyhexadecanoylglycyl) spicaminyl-amino]purine (SPK 271),
6-{4'-N-[N'-11-(3'-thienyl)-10-undecynoylglycyl)-spicaminyl-amino}purine (SPK 263), and
6-{4'-N-[N'-11-(3'-furyl)-10-undecynoylglycyl)-spicaminyl-amino}purine (SPK 266).

8. A method of treating cancer according to claim 6 wherein the spicamycin derivative is selected from the group consisting of the following compounds:
6-[4'-N-(N'-11-methyldodecanoylglycyl)spicaminyl-amino]purine (SPK 251),
6-[4'-N-(N'-trans,trans-2,4-dodecadienoylglycyl)-spicaminyl-amino]purine (SPK 282),
6-[4'-N-(N'-trans,trans-2,4-tridecadienoylglycyl)-spicaminyl-amino]purine (SPK 281),
6-[4'-N-(N'-trans,trans-2,4-tetradecadienoylglycyl)-spicaminyl-amino]purine (SPK 241),
6-[4'-N-(N'-12-bromododedanoylglycyl)spicaminyl-amino]purine (SPK 152),
6-[4'-N-(N'-13-bromotridecanoylglycyl)spicaminyl-amino]purine (SPK 276),
6-[4'-N-(N'-14-bromotetradecanoylglycyl)spicaminyl-amino]purine (SPK 273),
6-[4'-N-(N'-13-chlorotridecanoylglycyl)spicaminyl-amino]purine (SPK 278),
6-[4'-N-(N'-14-chlorotetradecanoylglycyl)spicaminyl-amino]purine (SPK 280),
6-[4'-N-(N'-14-fluorotetradechnoylglycyl)spicaminyl-amino]purine (SPK 279),
6-[4'-N-(N'-15-fluoropentadecanoylglycyl)spicaminyl-amino]purine (SPK 247),
6-[4'-N-(N'-2,2-difluorotetradecanoylglycyl) spicaminyl-amino]purine (SPK 182),
6-[4'-N-(N'-(S)-2-hydroxyhexadecanoylglycyl) spicaminyl-amino]purine (SPK 271),
6-{4'-N-[N'-11-(3'-thienyl)-10-undecynoylglycyl)-spicaminyl-amino}purine (SPK 263), and
6-{4'-N-[N'-11-(3'-furyl)-10-undecynoylglycyl)-spicaminyl-amino}purine (SPK 266).

9. A method for treating cancer according to claim 5 wherein the spicamycin derivative is selected from the group consisting of 6-[4'-N-(N'-trans,trans-2,4-dodecadienoyl-glycyl-spicaminyl-amino]purine (SPK 282) and 6-[4'-N-(N'-trans,trans,2,4-tetradecadienoylglycyl)spicaminyl-amino]purine (SPK 241).

10. A method for treating cancer according to claim 6 wherein the spicamycin derivative is selected from the group consisting of 6-[4'-N-(N'-trans,trans-2,4-dodecadienoyl-glycyl-spicaminyl-amino]purine (SPK 282 ) and 6-[4'-N-(N'-trans,trans,2,4-tetradecadienoylglycyl)spicaminyl-amino]purine (SPK 241).

11. A method for treating cancer according to claim 5 wherein the spicamycin derivative is 6-[4'-N-(N'trans,trans-2,4-tetradecadienoylglycyl)spicaminyl-amino]purine (SPK 241).

12. A method for treating cancer according to claim 6 wherein the spicamycin derivative is 6-[4'-N-(N'trans,trans-2,4-tetradecadienoylglycyl)spicaminyl-amino]purine (SPK 241).

13. A process for producing a spicamycin derivative, which comprises condensing 6-(4'-N-glycyl-spicaminyl-amino) purine of formula (IIIa) or a salt thereof

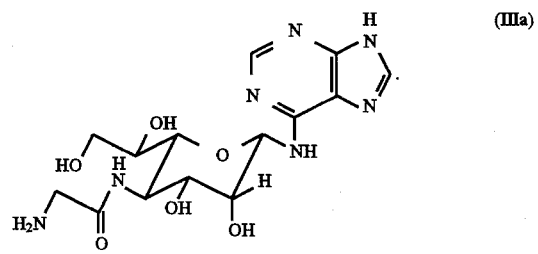

(IIIa)

with a carboxylic acid of the formula RCOOH or an active ester thereof to give a spicamycin derivative of formula (I) or a salt thereof

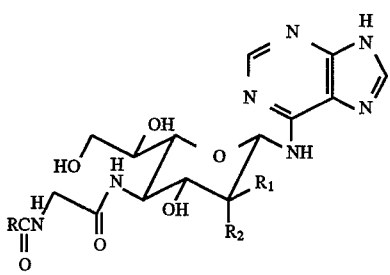

where $R_1$ is H and $R_2$ is OH; wherein R represents any one of substituents (1)–(16);
(1) a linear alkenyl having 11–13 carbon atoms;
(2) a linear alkyl having 12–13 carbon atoms, and a branched alkyl having 11–13 carbon atoms when $R_1$ represents H and $R_2$ represents OH;
(3) a linear haloalkyl having 10–15 carbon atoms;
(4) $CH_3(CH_2)_n CH(OH)$— or $CH_3(CH_2)_{n-1}CH(OH)$—$CH_2$—, wherein n denotes an integer of 9–13;
(5) an alkyl having 10–15 carbon atoms with an azide group or a cyano group;
(6) a linear alkyl having 10–13 carbon atoms with a phenoxy group or a halogen-substituted phenoxy group;

(7) 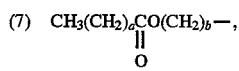

wherein a denotes an integer of 0–2 and b denotes an integer of 10–15;

(8) 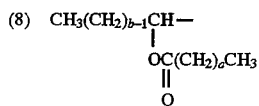

wherein a denotes an integer of 0–2 and b denotes an integer of 10–15;

(9) 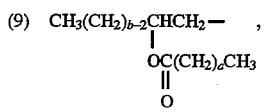

wherein a denotes an integer of 0–2 and b denotes an integer of 10–15;
(10) $CH_3(CH_2)_c SO_2 O(CH_2)_d$— wherein c denotes an integer of 0–3 and d denotes an integer of 10–15,

(11) 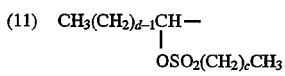

wherein c denotes an integer of 0–3 and d denotes an integer of 10–15;
(12) $(CH_3)_3 Si(CH_2)_{10}$— or $(CH_3)_3 Si$—$C\equiv C$—$(CH_2)_8$—

(13) 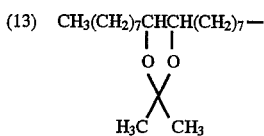

(14) 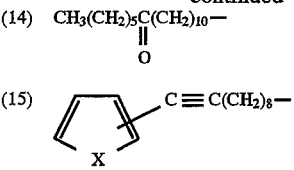

(15) 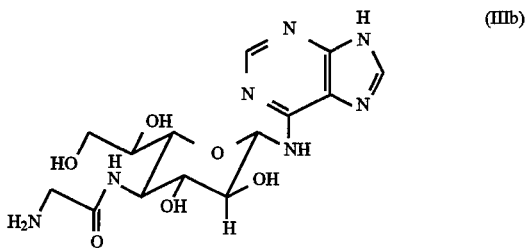

wherein X represents O or S and
(16) a linear alkadienyl having 11–13 carbon atoms.

14. A process for producing a spicamycin derivative, which comprises condensing 6-(4"-N-glycyl-septaminyl-amino) purine of formula (IIIb) or a salt thereof

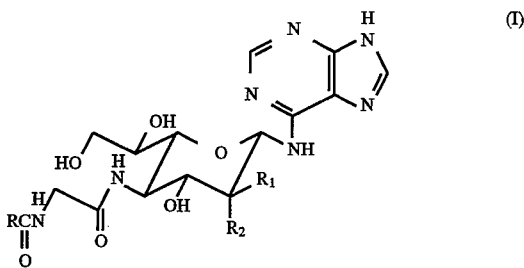

with a carboxylic acid of the formula RCOOH or an active ester thereof to give a spicamycin derivative of formula (I) or a salt thereof

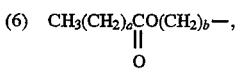

where $R_1$ is OH and $R_2$ is H;
and R represents any one of the substituents (1)–(15):
(1) a linear alkenyl having 11–13 carbon atoms;
(2) a linear haloalkyl having 10–15 carbon atoms;
(3) $CH_3(CH_2)_n CH(OH)$— or $CH_3(CH_2)_{n-1}CH(OH)$—$CH_2$—, wherein n denotes an integer of 9–13;
(4) an alkyl having 10–15 carbon atoms with an azide group or a cyano group;
(5) a linear alkyl having 10–13 carbon atoms with a phenoxy group or a halogen-substituted phenoxy group;

(6) 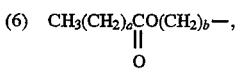

wherein a denotes an integer of 0–2 and b denotes an integer of 10–15;

(7) 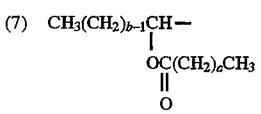

wherein a denotes an integer of 0–2 and b denotes an integer of 10–15;

(8) 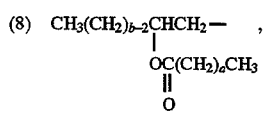

wherein a denotes an integer of 0–2 and b denotes an integer of 10–15;

(9) $CH_3(CH_2)_cSO_2O(CH_2)_d-$ wherein c denotes an integer of 0–3 and d denotes an integer of 10–15,

(10) 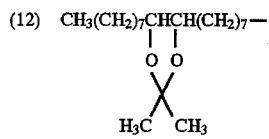

wherein c denotes an integer of 0–3 and d denotes an integer of 10–15;

(11) $(CH_3)_3Si(CH_2)_{10}-$ or $(CH_3)_3Si-C\equiv C-(CH_2)_8-$

(12) 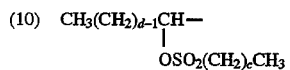

(13) 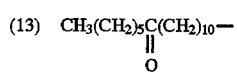

(14) 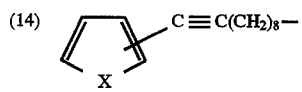

wherein X represents O or S and

(15) a linear alkadienyl having 11–13 carbon atoms.

15. A spicamycin derivative 6-(4'-N-glycyl-spicaminyl-amino) purine represented by the following formula (IIIa) or a salt thereof:

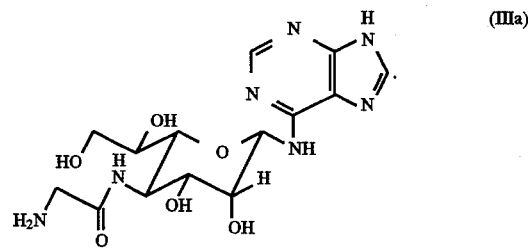

(IIIa)

16. A spicamycin derivative 6-(4'-N-glycyl-septaminyl-amino) purine represented by the following formula (IIIb) or a salt thereof:

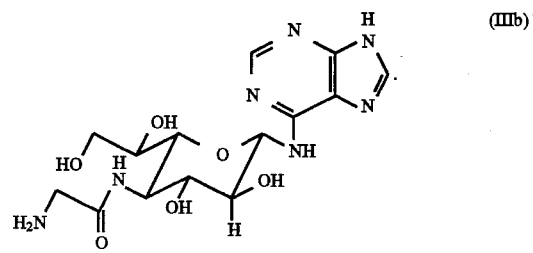

(IIIb)

* * * * *